United States Patent
Luo et al.

(10) Patent No.: US 7,132,240 B2
(45) Date of Patent: Nov. 7, 2006

(54) USE OF METHYLATED NUCLEIC ACID SEGMENTS FOR ISOLATING CENTROMERE DNA

(75) Inventors: Song Luo, Chicago, IL (US); Gregory Copenhaver, Oak Park, IL (US); Kevin Keith, Chicago, IL (US); Daphne Preuss, Chicago, IL (US)

(73) Assignee: The University of Chicago, Chicago, IL (US)

( * ) Notice: Subject to any disclaimer, the term of this patent is extended or adjusted under 35 U.S.C. 154(b) by 489 days.

(21) Appl. No.: 10/620,924

(22) Filed: Jul. 16, 2003

(65) Prior Publication Data

US 2004/0023282 A1 Feb. 5, 2004

Related U.S. Application Data

(62) Division of application No. 09/888,220, filed on Jun. 22, 2001, now Pat. No. 6,649,347.

(60) Provisional application No. 60/228,793, filed on Jun. 23, 2000.

(51) Int. Cl.
 *C12Q 1/68* (2006.01)
 *C12P 19/34* (2006.01)
(52) U.S. Cl. .......................... 435/6; 435/91.1
(58) Field of Classification Search .............. 435/6, 435/91.1
See application file for complete search history.

(56) References Cited

U.S. PATENT DOCUMENTS

| | | | |
|---|---|---|---|
| 4,282,287 | A | 8/1981 | Giese |
| 4,542,102 | A | 9/1985 | Dattagupta et al. |
| 5,252,743 | A | 10/1993 | Barrett et al. |
| 5,279,721 | A | 1/1994 | Schmid |
| 5,849,486 | A | 12/1998 | Heller et al. |
| 5,912,147 | A | 6/1999 | Stoler et al. |
| 5,919,626 | A | 7/1999 | Shi et al. |
| 6,011,200 | A | 1/2000 | Dellaporta et al. |

FOREIGN PATENT DOCUMENTS

| | | |
|---|---|---|
| WO | WO 98/55637 | 12/1998 |
| WO | WO 02/38811 A2 | 5/2002 |

OTHER PUBLICATIONS

De La Torre et al., Genome 35, 890-894 (1992).*
Alfenito and Birchler, "Molecular characterization of a maize B chromosome centric sequence," *Genetics*, 135:589-597, 1993.
Avides and Sunkel, "Isolation of chromosomes-associated proteins from Drosphila melanogaster that bind a human centrometric DNA sequence," *J. Cell Biol.*, 127(5):1159-1171, 1994.
Bellus, "How do specialty polymers modify the chemical and pharmaceutical industries?" *J Macromol. Sci. Pure Appl. Chem*, A31(10):1355-1376, 1994.

Bender, "Cytosine methylation of repeated sequences in eukaryotes: the role of DNA pairing," *Trends Biochem. Sci.*, 23:252-256, 1998.
Bianchi et al., "Direct visualization of the sites of DNA methylation in human, and mosquito chromosomes," *Chromosoma*, 94:362-366, 1986.
Blat and Kleckner, "Cohesins Bind to Preferential Sites along Yeast Chromosome III, with Differential Regulation along Arms versus the Centric Region," *Cell*, 98:249-259, 1999.
Bloom, "The centromere frontier: Kinetochore components, microtubule-based motility, and the CEN-value paradox," *Cell*, 73:621-624, 1993.
Butkus et al., "Cleavage of methylated CCCGGG sequences containing either N4-methylcytosine or 5-methylcytosine with *Msp*I, *Hpa*II, *Sma*I and *Crf*91 restriction endonucleases," *Nucl. Acids Res.*, 15(17):7091-7102, 1987.
Cao et al., "Conserved plant genes with similarity to mammalian de novo DNA methyltransferases," *Proc. Natl. Acad. Sci USA*, 97(9):4979-4984, 2000.
Choo, "Centromerization," *Trends Cell Biol.*, 10:182-188, 2000.
Copenhaver and Pikaard, "RFLP and physical mapping with an rDNA-specific endonuclease reveals that nucleolus organizer regions of Arabidopsis thaliana adjoin the telomeres on chromosomes 2 and 4," Plant J., 9(2):259-272, 1996.
Copenhaver and Pikaard, "Two-dimensional RFLP analyses reveal megabase sized clusters of rRNA gene variants in *Arabidopsis thaliana*, suggesting local spreading of variants as the mode for gene homogenization during concerted evolution," *Plant J.*, 9:273-282, 1996.
Copenhaver and Preuss, "Centromeres in the genomic era: unraveling paradoxes," *Current Opinion in Plant Biology*, 2:104-108, 1999.
Copenhaver et al., "Genetic Definition and Sequence Analysis of *Arabidopsis* Centromers," *Science*, 286:2468-2474, 1999.
Copenhaver et al., "Use of RFLPs larger than 100kbp to map the position and internal organization of the nucleolus organizer region on chromosome 2 in *Arabidopsis thaliana,"* Plant J., 7(2):273-286, 1995.
Copenhaver, et al., Genetic Definition and Sequence Analysis of Arabidopsis Centromeres, *Science* www.sciencemag.org, vol. 286, Dec. 24, 1999.
Dedon et al., "A simplified formaldehyde fixation and immunoprecipitation technique for studying protein-DNA interactions," *Anal. Biochem.*, 197(1):83-90, 1991.
Finnegan et al., "DNA methylation, a key regulator of plant development and other processes," *Current Opinion in Genetics & Development*, 10:217-223, 2000.
Fransz et al., "Integrated cytogenetic map of chromosome arm 4S of A. thaliana: structural organization of heterochromatic knob and centromere region," *Cell*, 100:367-376, 2000.

(Continued)

*Primary Examiner*—Kenneth R. Horlick
(74) *Attorney, Agent, or Firm*—Marshall, Gerstein & Borun LLP

(57) ABSTRACT

The invention provides efficient methods for the isolation of centromeres from potentially any organism. Using the methods of the invention, methylated centromere DNA may be isolated from potentially any centromere in an organism. The technique is amenable to mass screenings employing use of arrays comprising libraries of DNA from a target species.

43 Claims, 40 Drawing Sheets

OTHER PUBLICATIONS

Frommer et al., "A genomic sequencing protocol that yields a positive display of 5-methylcytosine residues in individual DNA strands," *Proc. Nat'l. Acad. Sci.* USA, 89:1827-1831, 1992.

Gruenbaum et al., "Methylation of CpG sequences in eukaryotic DNA," *FEBS Lett.*, 124(1):67-71, 1981.

Harrington et al., "Formation of *de novo* centromeres and construction of first-generation human artificial microchromosomes," *Nature Genetics*, 15:345-355, 1997.

Henikoff et al., "Heterochromatic deposition of centromeric histone H3-like proteins," *Proc. Natl. Acad. Sci. USA*, 97(2):716-721, 2000.

Hsiao and Carbon, "Direct selection procedure for the isolation of functional centromeric DNA," *Proc. Nat'l. Acad. Sci. USA*, 78(6):3760-3764, 1981.

Jacobsen and Meyerowitz, "Hypermethylated SUPERMAN Epigenetic Alleles in *Arabidopsis*," *Science*, 277:1100-1103, 1997.

Jasinkas and Hamkalo, "Purification and initial characterization of primate satellite chromatin," *Chromosome Res.*, 7(5):341-354, 1999.

Jeddeloh and Richards,".sup.m CCG Methylation in Angiosperms", *The Plant Journal*, 9(5):579-586, 1996.

Jeddeloh et al., "The DNA mehtylation locus DDM1 is required for maintenance of gene silencing in *Arabidopsis*," *Genes and Development*, 12:1714-1725, 1998.

Jones and Wolffe, "Relationship between chromatin organization and DNA methylation in determining gene expression," *Semin. Cancer Biol.*, 339-347, 1999.

Kondo et al., "Whole-genome methylation scan in ICF syndrome: hypomethylation of non-satellite DNA repeats D4Z4 and NBL2," *Hum. Mol. Genet.*, 9(4):597-604, 2000.

Kuo and Allis, "Roles of histone acetyltransferases and deacetylases in gene regulation," *Bioessays*, 20:615-626, 1998.

Lechner and Carbon, "A 240 kd multisubunit protein complex, CBF3, is a major component of the budding yeast centromere," *Cell*, 64:717-725, 1991.

Lindroth et al., "Requirement of Chromomethylase3 for maintenance of CpXpG methylation," *Science*, 292:2077-2080, 2001.

Liu et al., "Complementation of plant mutants with large genomic DNA fragments by a transformation-competent artificial chromosome vector accelerates positional cloning," *Proc. Nat'l. Acad. Sci. USA*, 96:6535-6540, 1999.

Lo et al., "A novel chromatin immunoprecipitation and array (CIA) analysis identifies a 460-kb CENP-A-Binding Neocentromere DNA," *Genome Res.*, 11:448-457, 2001.

Maluszynska and Heslop-Harrison, "Localization of tandemly repeated DNA sequences in *Arabidopsis thaliana*," *Plant J.*, 1(2):159-166, 1991.

Marra et al., "zA map for sequence analysis of the *Arabidopsis thaliana* genome," *Nature Genet.*, 22:265-270, 1999.

Martienssen and Colot, "DNA Methylation and Epigenetic Inheritance in Plants and Filamentous Fungi," *Science*, 293:1070-1074, 2001.

Martienssen and Richards, "DNA methylation in eukaryotes," *Current Opinion in Genetics & Development*, 5:234-242, 1995.

Martinez-Zapater et al., "A highly repeated DNA sequence in *Arabidopsis thaliana*," *Mol. Gen. Genet.*, 204:417-423, 1986.

McClelland et al., "Effect of site-specific modification on restriction endonuclease and DNA modification methyltransferases," *Nucl. Acids Res.*, 22(17):3640-3659, 1994.

McCombie et al., "The Complete Sequence of a Heterochromatic Island from a Higher Eukaryote," *Cell*, 100:377-386, 2000.

Melquist et al., "Arabidopsis *PAI* Gene Arrangements, Cytosine Methylation and Expression," *Genetics*, 153:401-413, 1999.

Mitchell et al., *J. Cell Science* 109, 2199-2206 (1996).

Mozo et al., "A complete BAC-based physical map of the *Arabidopsis thaliana* genome," *Nat. Genet.*, 22:271-275, 1999.

Nagane et al., "PCR amplification in bisulfite methylcytosine mapping in the GC-rich promoter region of amyloid precursor protein gene in autopsy human brain," *Brain Res. Protocols*, 5:167-171, 2000.

Ng and Bird, "DNA methylation and chromatin modification," *Current Opinion in Genetics & Development*, 9:158-163, 1999.

Preuss, et al., "Tetrad analysis possible in *Arabidopsis* with mutation of the QUARTET (QRT) genes," *Science*, 264:1458-1460, 1994.

Rattner, "The structure of the mammalian centromere," *Biossays*, 13(2):51:56, 1991.

Richards et al., "The centromere region of *Arabidopsis thaliana* chromosome 1 contains telomere-similar sequences," *Nucleic Acids Research*, 19(12):3351-3357, 1991.

Roberts and Macelis, "REBASE—restriction enzymes and methylases," *Nucleic Acids Research*, 28(1):306-307, 2000.

Robertson and Jones, "DNA methylation: past, present and future directions," *Carcinogenesis*, 21(3):461-467, 2000.

Round et al., "*Arabidopsis thaliana* centromere regions: genetic map positions and repetitive DNA structures," *Genome Res.* 7:1045-1053, 1997.

Singer et al., "Robertson's *Mutator* transposons in A. thaliana are regulated by the chromatin-remodeling gene Decrease in DNA Methylation (DDM1)," *Genes Dev.*, 15:591-602, 2001.

Streeck, "Single-strand and double-strand cleavage at half-modified recognition sites for the restriction nucleases Sau3A and Taq1," *Gene*, 12:267-275, 1980.

Sugimoto et al., "Functional cloning of centromere protein B (CENP-B) box-enriched alphoid DNA repeats utilizing the sequence-specific DNA binding activity of human CENP-B in vitro," *Chromosome Res.*, 2(6):453-459, 1994.

The Arabidopsis Genome Initiative, "Analysis of the genome sequence of the flowering plant *Arabidopsis thaliana*," *Nature*, 408:796-815, 2000.

Vafa et al., "CENP-A associated complex satellite DNA in the kinetochore of the Indian muntjac," *Chromosoma*, 108:367-374, 1999.

van Steensel and Henikoff, "Identification of in vivo DNA targets of chromatin proteins using tethered Dam methyltransferase," *Nature Biotechnology*, 18:424-428, 2000.

Vongs et al., "*Arabidopsis thaliana* DNA Methylation Mutants," *Science*, 260:1926-1928, 1993.

Waalwijk and Flavell, "MspI, and isoschizomer of HpaII which cleaves both unmethylated-HpaII sites," *Nucleic Acids Res.*, 5:3231-3236, 1978.

Willard, "Centromeres of mammalian chromosomes," *Trends Genet.*, 6(12):410-416, 1990.

Willard, "Centromeres: the missing link in the development of human artificial chromosomes," *Current Opinion in Genetics & Development*, 8:219-225, 1998.

Wolffe and Hayes, "Chromatin disruption and modification," *Nucleic Acids Research*, 27(3):711-720, 1999.

Woodcock, et al., Asymmetric Methylation in the Hypermethylated CpG Promoter Region of the Human L1 Retrotransposon, *The Journal of Biological Chemistry*, vol. 272, No. 12, Mar. 21, pp. 7810-7816, 1997.

Yoder et al., "Cytosine methylation and the ecology of intragenomic parasites," *Trends Genet.*, 13:335-340, 1997.

Zwick et al., "A rapid procedure for the isolation of C.sub.o t-1 DNA from plants," *Genome*, 40(1):138-142, 1997.

* cited by examiner

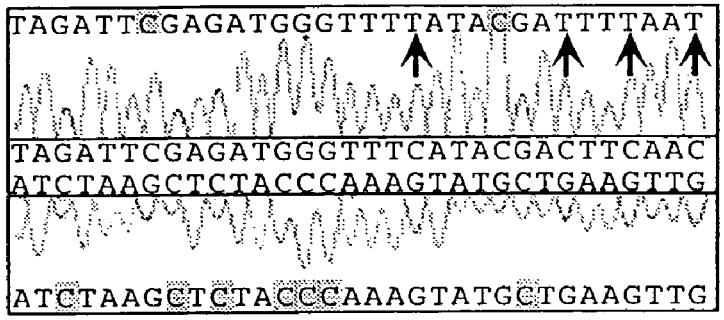
FIG. 1A
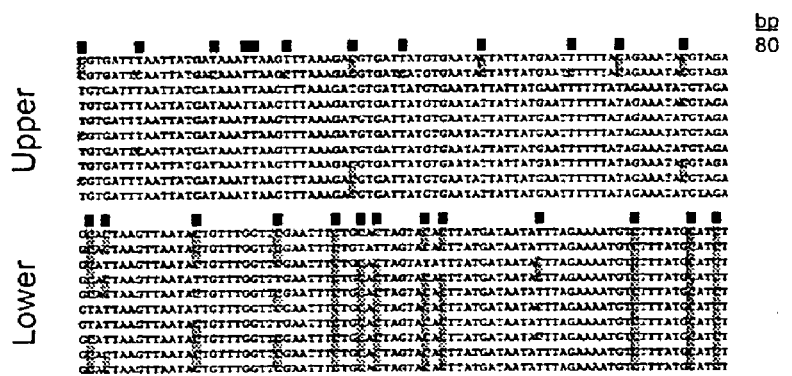
FIG. 1B
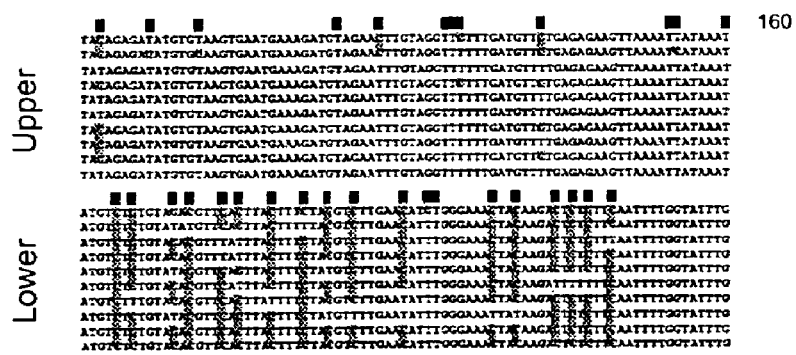

1)
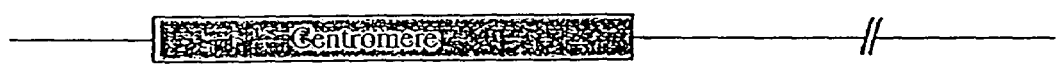
2)
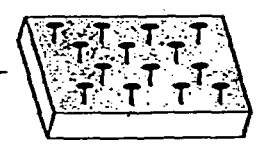
3)
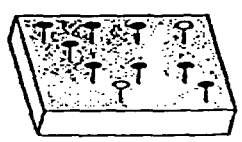 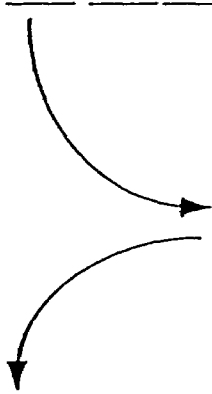 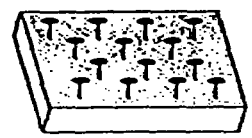
FIG. 7

< 5 Kb Fragments as the Probe    >10 Kb Fragments as the Probe

| CONTIGS | BAC NAME | METHYLATED | UNMETHYLATED | 180 BACS |
|---|---|---|---|---|
| ctg102 | M011E12 | D | | X |
| ctg102 | M023H06 | D | | X |
| ctg102 | M018G23 | L | | X |
| ctg102 | M025A16 | L | | X |
| ctg102 | I022B03 | M | | |
| ctg102 | M001N07 | M | | X |
| ctg102 | M012J02 | M | | X |
| ctg102 | M013M04 | M | | X |
| ctg102 | M017F23 | M | | X |
| ctg102 | M019B16 | M | | X |
| ctg102 | M024P24 | M | | X |
| ctg102 | M025B08 | M | | X |
| ctg102 | M025O05 | M | | X |
| ctg1077 | M007G01 | L | | |
| ctg1077 | M021I02 | L | | X |
| ctg1077 | I002K24 | M | | X |
| ctg1077 | I004A07 | M | | |
| ctg1077 | I004I21 | M | | X |
| ctg1077 | I006H08 | M | | X |
| ctg1077 | I007A08 | M | | |
| ctg1077 | I008A16 | M | | X |
| ctg1077 | I008K14 | M | | X |
| ctg1077 | I008K23 | M | | X |
| ctg1077 | I009C03 | M | | X |
| ctg1077 | I009G02 | M | | X |
| ctg1077 | I009K03 | M | | X |
| ctg1077 | I009M01 | M | | X |
| ctg1077 | I009M06 | M | | X |
| ctg1077 | I009P05 | M | | X |
| ctg1077 | I012J06 | M | | X |
| ctg1077 | I013E19 | M | | X |
| ctg1077 | I013I02 | M | | X |
| ctg1077 | I014E20 | M | | X |
| ctg1077 | I015P23 | M | | X |
| ctg1077 | I016H22 | M | | X |
| ctg1077 | I017M13 | M | | X |
| ctg1077 | I017O19 | M | | X |
| ctg1077 | I017P22 | M | | X |
| ctg1077 | I018N13 | M | | X |
| ctg1077 | I020B12 | M | | |
| ctg1077 | I020F20 | M | | X |
| ctg1077 | I020J15 | M | | X |

FIG. 9

| ctg1077 | I020N11 | M | | X |
|---|---|---|---|---|
| ctg1077 | I021C09 | M | | X |
| ctg1077 | I022O19 | M | | X |
| ctg1077 | I024F04 | M | | X |
| ctg1077 | I024F24 | M | | X |
| ctg1077 | I024N24 | M | | X |
| ctg1077 | I025C05 | M | | X |
| ctg1077 | I027A17 | M | | X |
| ctg1077 | I028B20 | M | | X |
| ctg1077 | I028P13 | M | | X |
| ctg1077 | M010B09 | M | | X |
| ctg1077 | M010N24 | M | | X |
| ctg1077 | M013D03 | M | | |
| ctg1077 | M022M19 | M | | X |
| ctg11 | M004H13 | L | | |
| ctg11 | M016E16 | L | | |
| ctg11 | M022A08 | L | | |
| ctg11 | M010G14 | M | L | |
| ctg11 | M016L05 | M | L | |
| ctg11 | I003I14 | M | | |
| ctg11 | I012H09 | M | | X |
| ctg11 | I022A03 | M | | X |
| ctg11 | I028F15 | M | | X |
| ctg11 | M013G04 | M | | |
| ctg11 | M015F10 | M | | |
| ctg11 | M020L24 | M | | |
| ctg11 | M021P20 | M | | |
| ctg11 | M022M13 | M | | |
| ctg1125 | M002F08 | D | L | X |
| ctg1125 | I024P12 | D | M | X |
| ctg1125 | I009K06 | D | | X |
| ctg1125 | I010J11 | D | | X |
| ctg1125 | I011B06 | D | | X |
| ctg1125 | I011F09 | D | | X |
| ctg1125 | I017M12 | D | | X |
| ctg1125 | I018F08 | D | | X |
| ctg1125 | I021M19 | D | | X |
| ctg1125 | I021O22 | D | | X |
| ctg1125 | I022M20 | D | | X |
| ctg1125 | I025M11 | D | | X |
| ctg1125 | I026O21 | D | | X |
| ctg1125 | M003N11 | D | | X |
| ctg1125 | M004G05 | D | | X |
| ctg1125 | M008O23 | D | | X |
| ctg1125 | I003A08 | M | | X |
| ctg1125 | I003N07 | M | | X |
| ctg1125 | I012E24 | M | | X |

FIG. 9 (cont'd)

| | | | | |
|---|---|---|---|---|
| ctg1125 | I012L05 | M | | X |
| ctg1125 | I013J20 | M | | X |
| ctg1125 | I016L03 | M | | X |
| ctg1125 | I026K06 | M | | X |
| ctg1125 | M009J13 | M | | X |
| ctg131 | M001B02 | D | | X |
| ctg131 | M004G17 | D | | X |
| ctg131 | M006C20 | D | | X |
| ctg131 | M007J20 | D | | X |
| ctg131 | M009P14 | D | | X |
| ctg131 | M011F07 | D | | X |
| ctg131 | M011G09 | D | | X |
| ctg131 | M016M20 | D | | X |
| ctg131 | M018J15 | D | | X |
| ctg131 | M020P21 | D | | X |
| ctg131 | M029O17 | D | | X |
| ctg131 | M003D17 | L | | X |
| ctg131 | M006A13 | L | | X |
| ctg131 | M008F07 | L | | X |
| ctg131 | M008P02 | L | | X |
| ctg131 | M009D23 | L | | |
| ctg131 | M010B04 | L | | X |
| ctg131 | M011D05 | L | | |
| ctg131 | M013A02 | L | | |
| ctg131 | M013A20 | L | | X |
| ctg131 | M023J09 | L | | X |
| ctg131 | M023O05 | L | | X |
| ctg131 | M027E10 | L | | X |
| ctg131 | I023C19 | M | M | |
| ctg131 | I001H15 | M | | X |
| ctg131 | I006O14 | M | | |
| ctg131 | I026B03 | M | | X |
| ctg131 | I028I04 | M | | X |
| ctg131 | M002O06 | M | | |
| ctg131 | M005D06 | M | | X |
| ctg131 | M005N10 | M | | X |
| ctg131 | M008H15 | M | | X |
| ctg131 | M014C08 | M | | X |
| ctg131 | M027C08 | M | | X |
| ctg131 | M030H12 | M | | X |
| ctg714 | M001K11 | D | | X |
| ctg714 | M014E03 | D | | X |
| ctg714 | M015D02 | L | | X |
| ctg714 | M022A09 | L | | |
| ctg714 | M008B13 | M | L | X |
| ctg714 | I014O12 | M | | X |
| ctg714 | M002D21 | M | | X |

FIG. 9 (cont'd)

| | | | | |
|---|---|---|---|---|
| ctg714 | M005O02 | M | | X |
| ctg716 | M007E17 | L | | |
| ctg716 | M009M02 | L | | |
| ctg716 | M012L11 | L | | X |
| ctg716 | M013P06 | L | | |
| ctg716 | M016C04 | L | | |
| ctg716 | M017E23 | L | | |
| ctg716 | M017F07 | L | | |
| ctg716 | M017H13 | L | | — |
| ctg716 | M019C15 | L | | |
| ctg716 | M019I03 | L | | |
| ctg716 | M021N19 | L | | |
| ctg716 | M026D12 | L | | |
| ctg716 | M026N02 | L | | |
| ctg716 | M027L02 | L | | |
| ctg716 | M028M23 | L | | |
| ctg716 | M029D04 | L | | X |
| ctg716 | I016J19 | M | L | X |
| ctg716 | I019I24 | M | L | X |
| ctg716 | I001G16 | M | | X |
| ctg716 | I001M08 | M | | X |
| ctg716 | I002A14 | M | | X |
| ctg716 | I002D20 | M | | X |
| ctg716 | I003B13 | M | | X |
| ctg716 | I010K18 | M | | X |
| ctg716 | I010M21 | M | | X |
| ctg716 | I013M20 | M | | X |
| ctg716 | I014C23 | M | | X |
| ctg716 | I016J23 | M | | X |
| ctg716 | I018L03 | M | | X |
| ctg716 | I018O09 | M | | X |
| ctg716 | I019J06 | M | | X |
| ctg716 | I022N06 | M | | X |
| ctg716 | I025L07 | M | | X |
| ctg716 | I026D01 | M | | X |
| ctg716 | I026L23 | M | | X |
| ctg716 | I026M13 | M | | X |
| ctg716 | I027K03 | M | | X |
| ctg716 | I027K06 | M | | X |
| ctg716 | M008B19 | M | | X |
| ctg716 | M008C21 | M | | X |
| ctg716 | M009P18 | M | | X |
| ctg716 | M015F17 | M | | X |
| ctg718 | M001P24 | L | | |
| ctg718 | M003K08 | L | | |
| ctg718 | M004K13 | L | | |
| ctg718 | M005A16 | L | | |

FIG. 9 (cont'd)

| | | | | |
|---|---|---|---|---|
| ctg718 | M005C11 | L | | |
| ctg718 | M010H16 | L | | |
| ctg718 | M011F08 | L | | |
| ctg718 | M017D14 | L | | |
| ctg718 | M021D01 | L | | |
| ctg718 | M025C01 | L | | |
| ctg718 | M030A22 | L | | |
| ctg718 | M003L04 | M | | X |
| ctg718 | M029O11 | M | | — |
| ctg719 | M009D11 | L | | |
| ctg719 | I028F20 | M | L | X |
| ctg719 | M018B03 | M | L | |
| ctg719 | M018I19 | M | L | |
| ctg719 | M022B09 | M | L | |
| ctg719 | M022C13 | M | L | |
| ctg719 | M022F21 | M | L | |
| ctg719 | M024F23 | M | L | |
| ctg719 | M026G23 | M | L | |
| ctg719 | I021A14 | M | | |
| ctg719 | M003D23 | M | | |
| ctg719 | M004H03 | M | | |
| ctg719 | M012F24 | M | | |
| ctg719 | M012P19 | M | | |
| ctg719 | M015N15 | M | | |
| ctg719 | M019I19 | M | | |
| ctg719 | M020G07 | M | | |
| ctg719 | M027I20 | M | | |
| ctg731 | M006D10 | D | L | X |
| ctg731 | M001I15 | D | | X |
| ctg731 | M009K02 | D | | X |
| ctg731 | M025C15 | D | | |
| ctg731 | M025F15 | D | | X |
| ctg731 | M026J06 | D | | X |
| ctg731 | I023D07 | L | | X |
| ctg731 | M002G13 | M | L | |
| ctg731 | M010F10 | M | L | |
| ctg731 | M015N04 | M | L | |
| ctg731 | M016C01 | M | L | |
| ctg731 | M016F22 | M | L | |
| ctg731 | M018P07 | M | L | |
| ctg731 | M022E07 | M | L | |
| ctg731 | M028G19 | M | L | |
| ctg731 | I002D01 | M | | |
| ctg731 | I002O08 | M | | |
| ctg731 | I009A07 | M | | |
| ctg731 | I012M11 | M | | X |
| ctg731 | I024N16 | M | | X |

FIG. 9 (cont'd)

| | | | | |
|---|---|---|---|---|
| ctg731 | M001J06 | M | | X |
| ctg731 | M007K14 | M | | X |
| ctg731 | M008O12 | M | | |
| ctg731 | M009J24 | M | | |
| ctg731 | M016M09 | M | | |
| ctg731 | M021I24 | M | | |
| ctg731 | M024I09 | M | | |
| ctg731 | M024O05 | M | | |
| ctg735 | M001E12 | L | | X |
| ctg735 | M007D03 | L | | X |
| ctg735 | M008A02 | L | | |
| ctg735 | M008D07 | L | | X |
| ctg735 | M008I22 | L | | |
| ctg735 | M009B19 | L | | X |
| ctg735 | M010F09 | L | | |
| ctg735 | M019C10 | L | | |
| ctg735 | M020F11 | L | | X |
| ctg735 | M021D19 | L | | X |
| ctg735 | M023H20 | L | | X |
| ctg735 | M024D20 | L | | |
| ctg735 | M026O08 | L | | X |
| ctg735 | I022E20 | M | M | |
| ctg735 | I008O19 | M | | |
| ctg735 | I015N16 | M | | X |
| ctg735 | I026A24 | M | | X |
| ctg735 | I027P20 | M | | |
| ctg735 | M006B01 | M | | X |
| ctg735 | M010H12 | M | | X |
| ctg735 | M011M16 | M | | X |
| ctg735 | M011P23 | M | | X |
| ctg735 | M013A18 | M | | |
| ctg735 | M015D18 | M | | X |
| ctg735 | M019J16 | M | | X |
| ctg735 | M022G04 | M | | X |
| ctg735 | M027I17 | M | | X |
| ctg735 | M028P17 | M | | X |
| ctg735 | M029A14 | M | | X |
| ctg735 | M029J04 | M | | X |
| ctg735 | M029K18 | M | | X |
| ctg735 | M032K16 | M | | X |
| ctg736 | I012P01 | D | | X |
| ctg736 | M003P12 | D | | X |
| ctg736 | M007H11 | D | | X |
| ctg736 | M003P01 | L | | |
| ctg736 | M021I16 | L | | X |
| ctg736 | M025M16 | L | | |
| ctg736 | M027H04 | L | | |

FIG. 9 (cont'd)

| | | | | |
|---|---|---|---|---|
| ctg736 | M029A06 | L | | |
| ctg736 | I002C13 | M | | X |
| ctg736 | I004B15 | M | | X |
| ctg736 | I004C11 | M | | X |
| ctg736 | I007C04 | M | | X |
| ctg736 | I009K02 | M | | X |
| ctg736 | I013D07 | M | | X |
| ctg736 | I023F23 | M | | X |
| ctg736 | I028G24 | M | | X |
| ctg736 | M001P15 | M | | X |
| ctg736 | M021M13 | M | | X |
| ctg830 | M003A09 | L | | |
| ctg830 | M006E22 | L | | |
| ctg830 | M006M12 | L | | |
| ctg830 | M007B18 | L | | |
| ctg830 | M012L15 | L | | |
| ctg830 | M013E20 | L | | |
| ctg830 | M013H16 | L | | |
| ctg830 | M013J14 | L | | |
| ctg830 | M015E08 | L | | |
| ctg830 | M016E01 | L | | |
| ctg830 | M016N03 | L | | |
| ctg830 | M017C13 | L | | |
| ctg830 | M017D02 | L | | |
| ctg830 | M019M10 | L | | |
| ctg830 | M020H14 | L | | |
| ctg830 | M020I24 | L | | |
| ctg830 | M020J16 | L | | |
| ctg830 | M021B02 | L | | |
| ctg830 | M024O13 | L | | |
| ctg830 | M025B04 | L | | |
| ctg830 | M026G05 | L | | |
| ctg830 | M026H12 | L | | |
| ctg830 | M027L15 | L | | |
| ctg830 | M027N03 | L | | |
| ctg830 | M028N05 | L | | |
| ctg830 | M009E16 | M | | |
| ctg830 | M026B13 | M | | |
| ctg920 | M001B22 | L | | |
| ctg920 | M005C15 | L | | |
| ctg920 | M008A04 | L | | X |
| ctg920 | M008G13 | L | | X |
| ctg920 | M010I15 | L | | |
| ctg920 | M019K14 | L | | X |
| ctg920 | M019L15 | L | | X |
| ctg920 | I027O22 | M | L | X |
| ctg920 | I020O07 | M | | |

FIG. 9 (cont'd)

| | | | | |
|---|---|---|---|---|
| ctg920 | M002B21 | M | | X |
| ctg920 | M009B06 | M | | X |
| ctg920 | M010I01 | M | | X |
| ctg920 | M022G20 | M | | X |
| ctg975 | M024F19 | D | | X |
| ctg975 | M007D21 | L | | |
| ctg975 | M026C24 | L | | |
| ctg975 | M008B22 | M | | X |
| ctg975 | M013M01 | M | | — |
| ctg975 | M019J02 | M | | X |
| ctg975 | M024K14 | M | | X |
| ctg975 | M030D03 | M | | X |
| ctg975 | M003C09 | | | X |
| | I007O17 | D | L | X |
| | I012D05 | D | L | X |
| | I013O09 | D | L | X |
| | I014L09 | D | L | X |
| | I016A19 | D | L | X |
| | I016P22 | D | L | X |
| | I018I01 | D | L | X |
| | I019B14 | D | L | X |
| | I019M02 | D | L | X |
| | I020J17 | D | L | X |
| | I022C06 | D | L | X |
| | I022O01 | D | L | X |
| | I023N22 | D | L | X |
| | I024H11 | D | L | X |
| | I025E03 | D | L | X |
| | I027B23 | D | L | X |
| | I027H06 | D | L | X |
| | M002J17 | D | L | X |
| | M006G07 | D | L | X |
| | M008H11 | D | L | X |
| | M008P11 | D | L | X |
| | M010H23 | D | L | X |
| | M010J15 | D | L | X |
| | M026C07 | D | L | X |
| | M032D01 | D | L | |
| | M001K03 | D | M | X |
| | I001D22 | D | | X |
| | I002B10 | D | | X |
| | I008D12 | D | | X |
| | I010C20 | D | | X |
| | I010D10 | D | | X |
| | I010G18 | D | | X |
| | I011G22 | D | | X |
| | I013B16 | D | | X |

FIG. 9 (cont'd)

| | | | | |
|---|---|---|---|---|
| | I013C23 | D | | X |
| | I013G06 | D | | X |
| | I013J05 | D | | X |
| | I013L02 | D | | X |
| | I013O07 | D | | X |
| | I013O15 | D | | X |
| | I014B11 | D | | X |
| | I014B12 | D | | X |
| | I014C24 | D | | X |
| | I014E09 | D | | X |
| | I014M09 | D | | X |
| | I014N24 | D | | X |
| | I015C11 | D | | X |
| | I015G11 | D | | X |
| | I015K18 | D | | X |
| | I015M20 | D | | X |
| | I016H14 | D | | X |
| | I017A03 | D | | X |
| | I017C07 | D | | X |
| | I017C18 | D | | X |
| | I017D16 | D | | X |
| | I017H23 | D | | X |
| | I017M11 | D | | X |
| | I018A13 | D | | X |
| | I018D05 | D | | X |
| | I018E13 | D | | X |
| | I018H10 | D | | X |
| | I018I18 | D | | X |
| | I018K08 | D | | X |
| | I018M19 | D | | X |
| | I019C12 | D | | X |
| | I019H12 | D | | X |
| | I021A24 | D | | X |
| | I021C12 | D | | X |
| | I021F21 | D | | X |
| | I021M22 | D | | X |
| | I021P14 | D | | X |
| | I022A19 | D | | X |
| | I022B12 | D | | X |
| | I022B17 | D | | X |
| | I022D24 | D | | X |
| | I022J10 | D | | X |
| | I022K16 | D | | X |
| | I023A09 | D | | X |
| | I023C12 | D | | X |
| | I024I11 | D | | X |
| | I025C16 | D | | X |

FIG. 9 (cont'd)

| | | | |
|---|---|---|---|
| I025E06 | D | | X |
| I025F23 | D | | X |
| I025G18 | D | | X |
| I025H17 | D | | X |
| I026A23 | D | | X |
| I026C12 | D | | X |
| I026D12 | D | | X |
| I026D14 | D | | X |
| I026G07 | D | | X |
| I026O02 | D | | X |
| I026O14 | D | | X |
| I027A15 | D | | X |
| I027B10 | D | | X |
| I027D12 | D | | X |
| I027E04 | D | | X |
| I027F10 | D | | X |
| I027L14 | D | | X |
| I028B05 | D | | X |
| I028D23 | D | | X |
| M001N01 | D | | X |
| M001N08 | D | | X |
| M001O18 | D | | |
| M002E19 | D | | X |
| M002K23 | D | | X |
| M005H16 | D | | X |
| M005J21 | D | | X |
| M005N16 | D | | X |
| M006F01 | D | | X |
| M007B16 | D | | X |
| M007D23 | D | | X |
| M007J23 | D | | X |
| M009B16 | D | | X |
| M009C09 | D | | X |
| M009F22 | D | | X |
| M009I18 | D | | X |
| M010K03 | D | | X |
| M011G03 | D | | X |
| M011M01 | D | | X |
| M017H09 | D | | X |
| M019I12 | D | | |
| M023G15 | D | | X |
| M025A01 | D | | X |
| M026N03 | D | | X |
| M028A03 | D | | X |
| M028F01 | D | | X |
| M029C10 | D | | |
| M029H17 | D | | |

FIG. 9 (cont'd)

| | | | | |
|---|---|---|---|---|
| | M029K02 | D | | |
| | M029K06 | D | | X |
| | M029M23 | D | | X |
| | I005P18 | L | | |
| | I010H02 | L | | |
| | I013J19 | L | | |
| | I019N07 | L | | |
| | I021J24 | L | | |
| | I025L21 | L | | — |
| | I026G01 | L | | |
| | I027L06 | L | | X |
| | M002L18 | L | | X |
| | M002M24 | L | | |
| | M003O24 | L | | |
| | M005A24 | L | | |
| | M005B19 | L | | X |
| | M006L23 | L | | X |
| | M008I11 | L | | X |
| | M008K13 | L | | X |
| | M010J22 | L | | |
| | M011C22 | L | | |
| | M011E15 | L | | |
| | M011F01 | L | | |
| | M011F13 | L | | |
| | M011M14 | L | | |
| | M013C20 | L | | |
| | M014F06 | L | | |
| | M014I21 | L | | |
| | M015H20 | L | | |
| | M016E04 | L | | |
| | M016L02 | L | | |
| | M017E02 | L | | |
| | M017N06 | L | | |
| | M018B14 | L | | |
| | M019B10 | L | | |
| | M021A21 | L | | |
| | M021B20 | L | | |
| | M023O24 | L | | |
| | M023P23 | L | | |
| | M024C04 | L | | |
| | M025M04 | L | | |
| | M026D01 | L | | |
| | M026H16 | L | | |
| | M026P17 | L | | |
| | M028A24 | L | | |
| | M029A21 | L | | |
| | M029H16 | L | | |

FIG. 9 (cont'd)

| | | | |
|---|---|---|---|
| M029M19 | L | | |
| M029N02 | L | | |
| M030A19 | L | | |
| M030D01 | L | | |
| M030D14 | L | | |
| M030H19 | L | | |
| M030I09 | L | | |
| M030O21 | L | | |
| M031D15 | L | | – |
| M031E05 | L | | |
| M031E12 | L | | |
| M031I08 | L | | |
| M031I12 | L | | |
| M031O05 | L | | |
| M032E22 | L | | |
| M032L02 | L | | |
| M032N16 | L | | |
| I001E03 | M | L | |
| I001F17 | M | L | |
| I002A10 | M | L | |
| I002E22 | M | L | |
| I002F07 | M | L | |
| I004M20 | M | L | |
| I005B09 | M | L | |
| I005C10 | M | L | |
| I005C20 | M | L | |
| I005E17 | M | L | |
| I008B06 | M | L | X |
| I008K19 | M | L | |
| I009B15 | M | L | |
| I009I07 | M | L | |
| I009I11 | M | L | |
| I009I20 | M | L | |
| I009N10 | M | L | |
| I009N20 | M | L | X |
| I009O14 | M | L | |
| I011J02 | M | L | |
| I011J23 | M | L | X |
| I012C11 | M | L | |
| I012I02 | M | L | |
| I012J21 | M | L | X |
| I012L23 | M | L | |
| I012N22 | M | L | |
| I013B09 | M | L | |
| I013C16 | M | L | |
| I013F09 | M | L | |
| I013O01 | M | L | |

FIG. 9 (cont'd)

| | | | | |
|---|---|---|---|---|
| | I014C08 | M | L | |
| | I014D22 | M | L | |
| | I015J09 | M | L | |
| | I015M09 | M | L | |
| | I015P10 | M | L | |
| | I016P21 | M | L | X |
| | I017G12 | M | L | |
| | I018B19 | M | L | |
| | I018C21 | M | L | — |
| | I018D11 | M | L | |
| | I018E15 | M | L | |
| | I018E22 | M | L | |
| | I019I14 | M | L | X |
| | I019L14 | M | L | |
| | I020P08 | M | L | X |
| | I021A10 | M | L | |
| | I021B12 | M | L | |
| | I021H12 | M | L | |
| | I023I15 | M | L | X |
| | I024E17 | M | L | |
| | I024I18 | M | L | X |
| | I024J04 | M | L | X |
| | I024P14 | M | L | X |
| | I024P21 | M | L | |
| | I025B17 | M | L | |
| | I025H03 | M | L | |
| | I025M08 | M | L | |
| | I026F23 | M | L | |
| | I026G19 | M | L | |
| | I027B04 | M | L | |
| | I027E03 | M | L | X |
| | I027I06 | M | L | X |
| | I027I07 | M | L | |
| | I027I11 | M | L | X |
| | I027I24 | M | L | X |
| | I027M21 | M | L | |
| | I028F18 | M | L | X |
| | I028K23 | M | L | |
| | I028M05 | M | L | X |
| | M002I24 | M | L | X |
| | M012E24 | M | L | |
| | M016A13 | M | L | |
| | M016G02 | M | L | |
| | M018H12 | M | L | |
| | M020J13 | M | L | |
| | M022G12 | M | L | |
| | M022I05 | M | L | |

FIG. 9 (cont'd)

| | | | | |
|---|---|---|---|---|
| | M024C15 | M | L | |
| | M024I07 | M | L | |
| | M026F04 | M | L | |
| | M030B01 | M | L | |
| | M031N02 | M | L | |
| | M032B03 | M | L | |
| | I001B14 | M | | |
| | I001C18 | M | | X |
| | I001H07 | M | | X |
| | I001L17 | M | | X |
| | I002D21 | M | | |
| | I002H01 | M | | X |
| | I002K19 | M | | X |
| | I003H18 | M | | X |
| | I003I08 | M | | |
| | I003L07 | M | | |
| | I004I08 | M | | |
| | I004P20 | M | | X |
| | I005D16 | M | | |
| | I005G01 | M | | |
| | I006B23 | M | | X |
| | I006D11 | M | | |
| | I006D18 | M | | |
| | I006E17 | M | | X |
| | I006J03 | M | | X |
| | I007C10 | M | | X |
| | I007C15 | M | | X |
| | I007C19 | M | | X |
| | I007E05 | M | | X |
| | I007K13 | M | | |
| | I007N08 | M | | |
| | I007O08 | M | | |
| | I008D05 | M | | X |
| | I008D08 | M | | X |
| | I008F19 | M | | X |
| | I008O14 | M | | X |
| | I008O23 | M | | X |
| | I009B09 | M | | X |
| | I009F16 | M | | X |
| | I009G13 | M | | X |
| | I009L22 | M | | X |
| | I009N18 | M | | X |
| | I010B14 | M | | X |
| | I010D22 | M | | |
| | I010E16 | M | | X |
| | I010G01 | M | | X |
| | I010I01 | M | | X |

FIG. 9 (cont'd)

|   | I010I09 | M |   |   |
|---|---------|---|---|---|
|   | I010I23 | M |   | X |
|   | I010J09 | M |   |   |
|   | I010J10 | M |   | X |
|   | I010J17 | M |   | X |
|   | I010K03 | M |   | X |
|   | I010L16 | M |   | X |
|   | I010L18 | M |   | X |
|   | I010M07 | M |   | X |
|   | I010M15 | M |   | X |
|   | I010N22 | M |   | X |
|   | I010O06 | M |   | X |
|   | I011C05 | M |   | X |
|   | I011E11 | M |   | X |
|   | I011G08 | M |   |   |
|   | I011J04 | M |   | X |
|   | I011J07 | M |   |   |
|   | I011K16 | M |   |   |
|   | I011L07 | M |   |   |
|   | I011M07 | M |   |   |
|   | I011M11 | M |   | X |
|   | I011P07 | M |   | X |
|   | I011P08 | M |   |   |
|   | I012B04 | M |   |   |
|   | I012B09 | M |   | X |
|   | I012C07 | M |   |   |
|   | I012D11 | M |   | X |
|   | I012E06 | M |   | X |
|   | I012G03 | M |   | X |
|   | I012I07 | M |   | X |
|   | I012J04 | M |   | X |
|   | I012J17 | M |   | X |
|   | I012M07 | M |   | X |
|   | I012N23 | M |   |   |
|   | I012P12 | M |   | X |
|   | I013B13 | M |   |   |
|   | I013C19 | M |   | X |
|   | I013D10 | M |   |   |
|   | I013F15 | M |   | X |
|   | I013G10 | M |   |   |
|   | I013H19 | M |   | X |
|   | I013L09 | M |   | X |
|   | I013O15 | M |   |   |
|   | I013O13 | M |   | X |
|   | I014A02 | M |   | X |
|   | I014A18 | M |   | X |
|   | I014H15 | M |   | X |

FIG. 9 (cont'd)

| | | | | |
|---|---|---|---|---|
| | 1014I07 | M | | X |
| | 1014I10 | M | | |
| | 1014J08 | M | | X |
| | 1014K02 | M | | X |
| | 1014M14 | M | | |
| | 1014M22 | M | | X |
| | 1014P17 | M | | X |
| | 1015B19 | M | | X |
| | 1015B23 | M | | X |
| | 1015D16 | M | | |
| | 1015E15 | M | | X |
| | 1015E24 | M | | X |
| | 1015F22 | M | | X |
| | 1015F24 | M | | X |
| | 1015I05 | M | | X |
| | 1015J08 | M | | |
| | 1015L23 | M | | X |
| | 1015M22 | M | | X |
| | 1016D08 | M | | X |
| | 1016D21 | M | | |
| | 1016G08 | M | | X |
| | 1016G23 | M | | X |
| | 1016H08 | M | | X |
| | 1016I12 | M | | X |
| | 1016J03 | M | | |
| | 1016K12 | M | | X |
| | 1016L05 | M | | X |
| | 1016L11 | M | | X |
| | 1016L13 | M | | X |
| | 1016O13 | M | | X |
| | 1017B03 | M | | X |
| | 1017E12 | M | | X |
| | 1017F19 | M | | X |
| | 1017F20 | M | | |
| | 1017H02 | M | | X |
| | 1017H04 | M | | X |
| | 1017L13 | M | | |
| | 1017L18 | M | | X |
| | 1018B05 | M | | |
| | 1018D09 | M | | |
| | 1018D17 | M | | X |
| | 1018G14 | M | | |
| | 1018L19 | M | | X |
| | 1018L20 | M | | |
| | 1018P11 | M | | X |
| | 1019A21 | M | | X |
| | 1019F08 | M | | X |

FIG. 9 (cont'd)

| | I019F21 | M | | |
|---|---|---|---|---|
| | I019I08 | M | | |
| | I019J08 | M | | |
| | I019M11 | M | | X |
| | I019N13 | M | | X |
| | I019O12 | M | | X |
| | I019O13 | M | | X |
| | I020C08 | M | | X |
| | I020C09 | M | | X |
| | I020C21 | M | | X |
| | I020D07 | M | | |
| | I020D08 | M | | X |
| | I020F02 | M | | X |
| | I020G12 | M | | |
| | I020H10 | M | | X |
| | I020I23 | M | | X |
| | I020K12 | M | | |
| | I020K22 | M | | |
| | I020P02 | M | | X |
| | I021A01 | M | | X |
| | I021A09 | M | | X |
| | I021A18 | M | | X |
| | I021B20 | M | | X |
| | I021F07 | M | | X |
| | I021F13 | M | | |
| | I021F17 | M | | X |
| | I021H11 | M | | |
| | I021K21 | M | | X |
| | I021L06 | M | | X |
| | I022D07 | M | | X |
| | I022D12 | M | | |
| | I022H09 | M | | X |
| | I022I07 | M | | X |
| | I022N13 | M | | |
| | I022O10 | M | | X |
| | I022O24 | M | | |
| | I022P16 | M | | X |
| | I022P18 | M | | X |
| | I023A18 | M | | X |
| | I023B15 | M | | |
| | I023F02 | M | | |
| | I023G09 | M | | X |
| | I023H08 | M | | |
| | I023J10 | M | | X |
| | I023K05 | M | | X |
| | I023L07 | M | | |
| | I023N04 | M | | X |

FIG. 9 (cont'd)

| | | | | |
|---|---|---|---|---|
| | I023P06 | M | | |
| | I024B10 | M | | |
| | I024C14 | M | | |
| | I024E18 | M | | X |
| | I024E19 | M | | |
| | I024F11 | M | | X |
| | I024G08 | M | | X |
| | I024M20 | M | | |
| | I024M23 | M | | |
| | I025A13 | M | | |
| | I025B02 | M | | |
| | I025H15 | M | | |
| | I025K04 | M | | |
| | I025K16 | M | | X |
| | I025M19 | M | | |
| | I026A21 | M | | |
| | I026A22 | M | | X |
| | I026C10 | M | | |
| | I026G04 | M | | X |
| | I026I07 | M | | X |
| | I026I20 | M | | |
| | I026K04 | M | | |
| | I026N05 | M | | X |
| | I026N23 | M | | X |
| | I027A14 | M | | |
| | I027A18 | M | | X |
| | I027B24 | M | | X |
| | I027C09 | M | | |
| | I027C20 | M | | X |
| | I027D08 | M | | |
| | I027F08 | M | | |
| | I027G17 | M | | X |
| | I027I04 | M | | X |
| | I027K08 | M | | |
| | I027M15 | M | | |
| | I027N19 | M | | |
| | I027P14 | M | | X |
| | I028A17 | M | | |
| | I028F04 | M | | |
| | I028F24 | M | | X |
| | I028G15 | M | | |
| | I028H05 | M | | |
| | I028I01 | M | | |
| | I028I02 | M | | |
| | I028I13 | M | | X |
| | I028L02 | M | | |
| | I028N05 | M | | X |

FIG. 9 (cont'd)

| | | | | |
|---|---|---|---|---|
| | I028N14 | M | | X |
| | M001C24 | M | | |
| | M001J16 | M | | |
| | M001M11 | M | | X |
| | M002C22 | M | | X |
| | M002J18 | M | | X |
| | M002N17 | M | | X |
| | M003N18 | M | | |
| | M003N20 | M | | − |
| | M003P22 | M | | |
| | M004G02 | M | | X |
| | M005B07 | M | | X |
| | M007E20 | M | | |
| | M007H06 | M | | X |
| | M007H21 | M | | |
| | M007P19 | M | | |
| | M008H05 | M | | X |
| | M008N22 | M | | X |
| | M008P08 | M | | X |
| | M009B11 | M | | X |
| | M009F04 | M | | X |
| | M009K21 | M | | |
| | M010P04 | M | | X |
| | M011I16 | M | | |
| | M011I19 | M | | |
| | M011J18 | M | | X |
| | M011J19 | M | | |
| | M011M20 | M | | |
| | M011P21 | M | | |
| | M013G20 | M | | |
| | M013H08 | M | | X |
| | M013I24 | M | | |
| | M013J23 | M | | |
| | M013K05 | M | | |
| | M013K09 | M | | |
| | M013N24 | M | | |
| | M015A07 | M | | |
| | M015A20 | M | | |
| | M015E17 | M | | |
| | M015G16 | M | | |
| | M015I20 | M | | |
| | M015I21 | M | | |
| | M015K15 | M | | |
| | M015L10 | M | | X |
| | M015M09 | M | | |
| | M015M14 | M | | |
| | M015M15 | M | | |

FIG. 9 (cont'd)

|   | M015M20 | M |   |   |   |
|---|---------|---|---|---|---|
|   | M016F03 | M |   |   |   |
|   | M017A17 | M |   |   |   |
|   | M017A23 | M |   |   |   |
|   | M017B08 | M |   |   | X |
|   | M017C19 | M |   |   |   |
|   | M017F12 | M |   |   |   |
|   | M017I24 | M |   |   |   |
|   | M017J08 | M |   |   |   |
|   | M017K05 | M |   |   |   |
|   | M017O11 | M |   |   |   |
|   | M017P18 | M |   |   |   |
|   | M019E13 | M |   |   |   |
|   | M019G18 | M |   |   |   |
|   | M019I17 | M |   |   |   |
|   | M019K09 | M |   |   |   |
|   | M019L14 | M |   |   |   |
|   | M019O15 | M |   |   |   |
|   | M019P22 | M |   |   |   |
|   | M020I23 | M |   |   |   |
|   | M020O15 | M |   |   |   |
|   | M021A19 | M |   |   |   |
|   | M021E21 | M |   |   |   |
|   | M021G09 | M |   |   |   |
|   | M021I22 | M |   |   |   |
|   | M021J13 | M |   |   |   |
|   | M021J16 | M |   |   |   |
|   | M021M23 | M |   |   |   |
|   | M021O23 | M |   |   |   |
|   | M022O17 | M |   |   |   |
|   | M023C22 | M |   |   |   |
|   | M023J14 | M |   |   |   |
|   | M023N20 | M |   |   |   |
|   | M023O08 | M |   |   |   |
|   | M023O09 | M |   |   |   |
|   | M023O18 | M |   |   |   |
|   | M023P11 | M |   |   |   |
|   | M025D03 | M |   |   | X |
|   | M025D20 | M |   |   |   |
|   | M025E17 | M |   |   |   |
|   | M025H06 | M |   |   | X |
|   | M025J22 | M |   |   | X |
|   | M025O24 | M |   |   |   |
|   | M026O17 | M |   |   |   |
|   | M027H13 | M |   |   |   |
|   | M027J21 | M |   |   |   |
|   | M027K17 | M |   |   |   |

FIG. 9 (cont'd)

|   | M027M20 | M |   |   |
|---|---|---|---|---|
|   | M027O09 | M |   |   |
|   | M027O14 | M |   |   |
|   | M027O17 | M |   |   |
|   | M028P08 | M |   |   |
|   | M028P14 | M |   | X |
|   | M029A07 | M |   |   |
|   | M029B16 | M |   |   |
|   | M029G12 | M |   | — |
|   | M029I19 | M |   |   |
|   | M029M22 | M |   |   |
|   | M029P10 | M |   |   |
|   | M029P15 | M |   |   |
|   | M030E15 | M |   | X |
|   | M030F14 | M |   |   |
|   | M030G01 | M |   |   |
|   | M030O17 | M |   |   |
|   | M031C19 | M |   |   |
|   | M031H15 | M |   | X |
|   | M031N08 | M |   | X |
|   | M032D14 | M |   | X |
|   | M032J13 | M |   | X |
|   |   |   |   |   |

FIG. 9 (cont'd)

1. Centromere BACs can be labeled by heavily methylated DNA fragments

| CONTIGS | BAC NAME | HEAVILY METHYLATED DNA | LIGHT or NON-METHYLATED DNA | 180 BACS |
|---|---|---|---|---|
| ctg1125 | I009K06 | D | | X |
| ctg1125 | I010J11 | D | | X |
| ctg131 | M004G17 | D | | X |
| ctg131 | M006C20 | D | | X |
| ctg731 | M026J06 | D | | X |
| ctg736 | I012P01 | D | | X |
| ctg735 | M020F11 | L | | X |
| ctg735 | M021D19 | L | | X |
| ctg920 | M019K14 | L | | X |
| ctg920 | M019L15 | L | | X |
| ctg1077 | I017M13 | M | | X |
| ctg1077 | I017O19 | M | | X |
| ctg11 | M015F10 | M | | |
| ctg11 | M020L24 | M | | |
| ctg719 | M004H03 | M | | |
| ctg719 | M012F24 | M | | |
| Ctg0 | I007C19 | M | | X |
| Ctg0 | I007E05 | M | | X |
| Ctg0 | I007K13 | M | | |
| Ctg0 | I007N08 | M | | |
| Ctg0 | I007O08 | M | | |

2. rDNA BACs can be labeled by both way

| CONTIGS | BAC NAME | HEAVILY METHYLATED DNA | LIGHT or NON-METHYLATED DNA | 180 BACS |
|---|---|---|---|---|
| ctg4 | I012D17 | M | M | |
| ctg4 | I013A06 | M | M | |
| ctg4 | I013G04 | M | M | |
| ctg4 | I013M21 | M | M | |
| ctg4 | I014D06 | M | M | |
| Ctg0 | I003E12 | M | M | |
| Ctg0 | I003F05 | M | M | |
| Ctg0 | I003F10 | M | M | |

3. 180 BACs could be not labeled if they are locate out of centromere

| CONTIGS | BAC NAME | HEAVILY METHYLATED DNA | LIGHT or NON-METHYLATED DNA | 180 BACS |
|---|---|---|---|---|
| ctg757 | M009N20 | | | X |
| ctg764 | I028H14 | | | X |
| ctg766 | I024J11 | | | X |
| ctg768 | I028K13 | | | X |
| ctg772 | I028O13 | | | X |
| ctg778 | I014J02 | | | X |

FIG. 10

Measuring centromere functions in plant mini-chromosomes
Qualitative assays
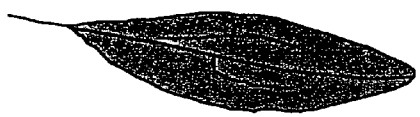
Stable
Unstable
Quantitative assays
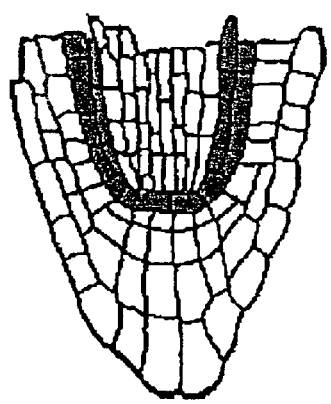
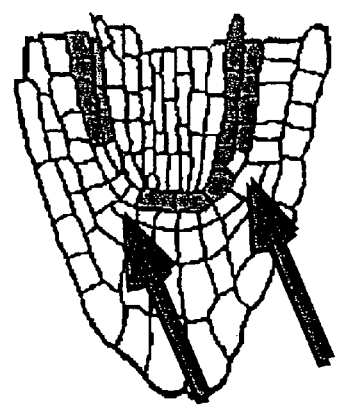
Mitosis
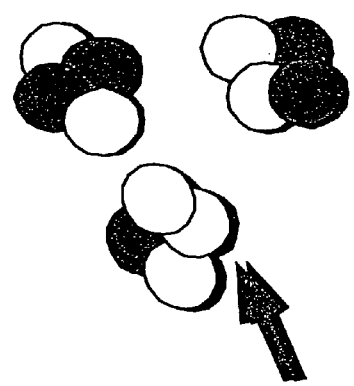
Meiosis
FIG. 13

SEQUENCE LISTING

<160> NUMBER OF SEQ ID NOS: 24

<210> SEQ ID NO 1
<211> LENGTH: 32
<212> TYPE: DNA
<213> ORGANISM: Arabidopsis

<400> SEQUENCE: 1
tagattcgag atgggtttca tacgacttca ac                          32

<210> SEQ ID NO 2
<211> LENGTH: 32
<212> TYPE: DNA
<213> ORGANISM: Arabidopsis

<400> SEQUENCE: 2
gttgaagtcg tatgaaaccc atctcgaatc ta                          32

<210> SEQ ID NO 3
<211> LENGTH: 32
<212> TYPE: DNA
<213> ORGANISM: Arabidopsis

<400> SEQUENCE: 3
tagattcgag atgggtttta tacgatttta at                          32

<210> SEQ ID NO 4
<211> LENGTH: 32
<212> TYPE: DNA
<213> ORGANISM: Arabidopsis

<400> SEQUENCE: 4
gttgaagtcg tatgaaaccc atctcgaatc ta                          32

<210> SEQ ID NO 5
<211> LENGTH: 240
<212> TYPE: DNA
<213> ORGANISM: Arabidopsis

<400> SEQUENCE: 5
cgtgatttaa ttatgataaa ttaagtttaa agacgtgatt atgtgaatac tattatgaat     60
tttttacaga aatacgtaga tacagagata tgtgtaagtg aatgaaagat gtagaacttg    120
taggttcttt gatgttctga gagaagttaa aattataaat ttgaagaaat tttaatagat    180
ttttagtgtc tagattagtt agggaataaa ttgggaatga gaaataaaac taaaacgtct    240

<210> SEQ ID NO 6
<211> LENGTH: 240
<212> TYPE: DNA
<213> ORGANISM: Arabidopsis

<400> SEQUENCE: 6
cgtgattcaa ttatgacaaa ttaagcttaa agacgtgatc atgtgaatac tattatgaat     60
cttttacaga aatacgtaga tacagagaca tgtgcaagtg aatgaaagat gtagaacttg    120
taggtttttt gatgttctga gagaagttaa aatcataaat ttgaagaaat ttcaatagat    180
tcctagtgtc tagattagtt agggaataaa ttgggaatga gaaataaaac taaaatgtct    240

<210> SEQ ID NO 7
<211> LENGTH: 240

```
<212> TYPE: DNA
<213> ORGANISM: Arabidopsis

<400> SEQUENCE: 7
tgtgatttaa ttatgataaa ttaagtttaa agatgtgatt atgtgaatat tattatgaat      60
tttttataga aatatgtaga tatagagata tgtgtaagtg aatgaaagat gtagaatttg     120
taggtttttt gatgttttga gagaagttaa aattataaat ttgaagaaat tttaatagat     180
ttttagtgtt tagattagtt agggaataaa ttgggaatga gaaataaaat taaaatgttt     240

<210> SEQ ID NO 8
<211> LENGTH: 240
<212> TYPE: DNA
<213> ORGANISM: Arabidopsis

<400> SEQUENCE: 8
tgtgatttaa ttatgataaa ttaagtttaa agatgtgatt atgtgaatat tattatgaat      60
tttttataga aatacgtaga tacagagata tgtgtaagtg aatgaaagat gtagaatttg     120
taggttcttt gatgttctga gagaagttaa aattataaat ctgaagaaat tttaatagat     180
tcttagtgtt tagattagtt agggaataaa ttgggaatga gaaataaaat taaaacgtct     240

<210> SEQ ID NO 9
<211> LENGTH: 240
<212> TYPE: DNA
<213> ORGANISM: Arabidopsis

<400> SEQUENCE: 9
tgtgatttaa ttatgataaa ttaagtttaa agatgtgatt atgtgaatat tattatgaat      60
tttttataga aatatgtaga tatagagata tgtgtaagtg aatgaaagat gtagaatttg     120
taggtttttt gatgttttga gagaagttaa aattataaat ttgaagaaat tttaatagat     180
ttttagtgtt tagattagtt agggaataaa ttgggaatga gaaataaaat taaaatgttt     240

<210> SEQ ID NO 10
<211> LENGTH: 240
<212> TYPE: DNA
<213> ORGANISM: Arabidopsis

<400> SEQUENCE: 10
cgtgatttaa ttatgataaa ttaagtttaa agatgtgatt atgtgaatat tattatgaat      60
tttttataga aatatgtaga tatagagata tgtgtaagtg aatgaaagat gtagaatttg     120
taggtttttt gatgttttga gagaagttaa aattataaat ttgaagaaat tttaatagat     180
ttttagtgtt tagattagtt agggaataaa ttgggaatga gaaataaaat taaaatgttt     240

<210> SEQ ID NO 11
<211> LENGTH: 240
<212> TYPE: DNA
<213> ORGANISM: Arabidopsis

<400> SEQUENCE: 11
tgtgattcaa ttatgataaa ttaagtttaa agatgtgatt atgtgaatat tattatgaat      60
tttttataga aatatgtaga tacagagata tgtgtaagtg aatgaaagat gtagaatttg     120
taggtttttt gatgttctga gagaagttaa aattataaat ttgaagaaat tttaatagat     180
ttttagtgtt tagattagtt agggaataaa ttgggaatga gaaataaaat taaaatgttt     240

<210> SEQ ID NO 12
```

```
<211> LENGTH: 240
<212> TYPE: DNA
<213> ORGANISM: Arabidopsis

<400> SEQUENCE: 12
tgtgatttaa ttatgataaa ttaagtttaa agacgtgatt atgtgaatat tattatgaat      60
tttttataga aatacgtaga tacagagata tgtgtaagtg aatgaaagat gtagaatttg     120 taggttttt gatgttttga gagaagttaa aattataaat ttgaagaaat tttaatagat     180
ttttagtgtt tagattagtt agggaataaa ttgggaatga gaaataaaat taaaatgttt     240

<210> SEQ ID NO 13
<211> LENGTH: 240
<212> TYPE: DNA
<213> ORGANISM: Arabidopsis

<400> SEQUENCE: 13
cgtgatttaa ttatgataaa ttaagtttaa agacgtgatt atgtgaatat tattatgaat      60
tttttataga aatacgtaga tacagagata tgtgtaagtg aatgaaagat gtagaatttg     120 taggttttt gatgttctga gagaagttaa aattataaat ttgaagaaat tttaatagat     180
ttttagtgtt tagattagtt agggaataaa ttgggaatga gaaataaaat taaaatgttt     240

<210> SEQ ID NO 14
<211> LENGTH: 240
<212> TYPE: DNA
<213> ORGANISM: Arabidopsis

<400> SEQUENCE: 14
tgtgatttaa ttatgataaa ttaagtttaa agacgtgatt atgtgaatat tattatgaat      60
tttttataga aatatgtaga tatagagata tgtgtaagtg aatgaaagat gtagaatttg     120 taggttttt gatgttttga gagaagttaa aattataaat ttgaagaaat tttaatagat     180
ttttagtgtt tagattagtt agggaataaa ttgggaatga gaaataaaat taaaatgttt     240

<210> SEQ ID NO 15
<211> LENGTH: 240
<212> TYPE: DNA
<213> ORGANISM: Arabidopsis

<400> SEQUENCE: 15 agacgttta gttttatttc tcattcccaa tttatttcct aactaatcta gacactagga      60
atctattgaa atttcttcag gtttatggtt ttaacttctc tcagaacatc aaagggtcta     120
caagttctgc atctttcatt cacttgcaca tgtctctgta tctacgtatt tctgtaaaag     180
atttataata gtattcacat gatcacgtct ttaagcttgg tttgtcataa ttgaatcacg     240

<210> SEQ ID NO 16
<211> LENGTH: 240
<212> TYPE: DNA
<213> ORGANISM: Arabidopsis

<400> SEQUENCE: 16 agacgttta gttttatttc tcattcccaa tttatttcct aactaatcta gacactagga      60
atctattgaa atttctttag gtttatggtt ttaacttctc tcagaacatc aaagggttta     120
caagttctgc attttcatt cacttgtata tgtctctgta tctacgtatt tctgtaaaag     180
atttataata gtattcacat gattatgtct ttaagcttgg tttgtcataa ttgaatcacg     240
```

<210> SEQ ID NO 17
<211> LENGTH: 240
<212> TYPE: DNA
<213> ORGANISM: Arabidopsis

<400> SEQUENCE: 17

```
agacgtttta gttttatttc tcattcccaa tttattctct aactaatcta gacactagga      60
atctattgaa atttcttcag gtttatggtt ttaatttctc tcagaacatc aaagggttta     120
caagttctgc atctttcatt tatttgcaca tgtctctgta tctacgtatt tctgtaaaag     180
attcataata gtatttatat gatcacgtct ttaagcttgg tttgtcataa ttgaattacg     240
```

<210> SEQ ID NO 18
<211> LENGTH: 240
<212> TYPE: DNA
<213> ORGANISM: Arabidopsis

<400> SEQUENCE: 18

```
agacgtttta gttttatttc tcattcccaa tttattccct aactaatcta gacactagga      60
atctattgaa atttcttcag gtttatggtt ttaacttctc tcagaacatc aaagggttta     120
caagttctgc atctttcatt tatttgcaca tgtctctgta tctacgtatt tctgtaaaag     180
attcataata gtattcacat gatcacgtct ttaagtttgg tttgttataa ttgaatcacg     240
```

<210> SEQ ID NO 19
<211> LENGTH: 240
<212> TYPE: DNA
<213> ORGANISM: Arabidopsis

<400> SEQUENCE: 19

```
agacgtttta gttttatttc tcattcccaa tttattccct aactaatcta gacactagga      60
atctattgaa atttcttcag gtttatggtt ttaacttctc tcagaacatc aaagggttta     120
caagttctgt atctttcatt cacttgcata tgtctctgta tctacgtatt tctgtaaaag     180
atttataata gtattcacat gatcacgtct ttaagcttgg tttgtcataa ttgaatcacg     240
```

<210> SEQ ID NO 20
<211> LENGTH: 240
<212> TYPE: DNA
<213> ORGANISM: Arabidopsis

<400> SEQUENCE: 20

```
agatgtttta gttttatttt ttatttttaa tttattccct aactaatcta gacactagga      60
atctattgaa atttcttcag gtttatggtt ttaactttt  ttagaacatc aaagggttta     120
caagttctgc atctttcatt tacttgcaca tgtctctgta tctacgtatt tctgtaaaag     180
attcataata gtattcacat gatcacgtct ttaagcttgg tttgttataa ttgaattatg     240
```

<210> SEQ ID NO 21
<211> LENGTH: 240
<212> TYPE: DNA
<213> ORGANISM: Arabidopsis

<400> SEQUENCE: 21

```
agacgtttta gttttatttt tcattcccaa tttattccct aactaattta gatattagga      60
atttattgaa atttcttcag gtttatggtt ttaacttctc tcagaacatc aaagggttta     120
taagttctgc atctttttatt cacttgcaca tgtttctgta tctacgtatt tctgtaaaag     180
atttataata gtattcacat gatcacgtct ttaagtttgg tttgtcataa ttgaattatg     240
```

<210> SEQ ID NO 22
<211> LENGTH: 240
<212> TYPE: DNA
<213> ORGANISM: Arabidopsis

<400> SEQUENCE: 22

| | | | | |
|---|---|---|---|---|
| agacgtttta | gttttatttt | tcatttttaa | tttatttttt | aattaattta gatattagga | 60 |
| atctattgaa | atttcttcag | gtttatggtt | ttaacttctc | tcagaatatt aaagggttta | 120 |
| taagttttgt | atctttcatt | cacttgcata | tgtctctgta | tctacgtatt tctgtaaaag | 180 |
| attcataata | gtattcacat | gatcacgtct | ttaagcttgg | tttgtcataa ttgaattacg | 240 |

<210> SEQ ID NO 23
<211> LENGTH: 240
<212> TYPE: DNA
<213> ORGANISM: Arabidopsis

<400> SEQUENCE: 23

| | | | | |
|---|---|---|---|---|
| agacgtttta | gttttatttc | tcattcctaa | tttattccct | aactaatcta gacactagga | 60 |
| atctattgaa | atttcttcag | gtttatggtt | ttaacttctc | tcagaacatc aaagggttta | 120 |
| caagttctgc | atctttcatt | cacttgcaca | tgtctctgta | tctacgtatt tctgtaaaag | 180 |
| atttataata | gtattcacat | gatcacgtct | ttaagcttgg | tttgtcataa ttgaatcacg | 240 |

<210> SEQ ID NO 24
<211> LENGTH: 240
<212> TYPE: DNA
<213> ORGANISM: Arabidopsis

<400> SEQUENCE: 24

| | | | | |
|---|---|---|---|---|
| agacgtttta | gttttatttc | tcattcctaa | tttattccct | aactaatcta gacactagga | 60 |
| atctattgaa | atttcttcag | gtttatggtt | ttaacttctc | tcagaacatc aaagggttta | 120 |
| caagttctgc | atctttcatt | cacttgcaca | tgtctctgta | tctacgtatt tctgtaaaag | 180 |
| atttataata | gtattcacat | gatcacgtct | ttaagcttgg | tttgtcataa ttgaatcacg | 240 |

USE OF METHYLATED NUCLEIC ACID SEGMENTS FOR ISOLATING CENTROMERE DNA

This application is a divisional application of application Ser. No. 09/888,220, filed Jun. 22, 2001, now U.S. Pat. No. 6,649,347. This application claims the priority of U.S. Provisional Application No. 60/228,793, filed Jun. 23, 2000, the disclosure of which is specifically incorporated herein by reference in its entirety.

The government owns rights in the invention pursuant to U.S. Department of Agriculture Grant No. 96-3304-3491, National Science Foundation Grant No. 9872641 and Grant No. DOEDE-FG05-92OR22072 from the Consortium for Plant Biotechnology.

BACKGROUND OF THE INVENTION

I. Field of the Invention

The present invention relates generally to the field of molecular biology. More particularly, it concerns methods for isolating centromere DNA.

II. Description of Related Art

It is well documented that centromere function is crucial for stable chromosomal inheritance in almost all eukaryotic organisms, including essentially all plants (reviewed in Nicklas 1988) or animals. For example, broken chromosomes that lack a centromere (acentric chromosomes) are rapidly lost from cell lines, while fragments that have a centromere are faithfully segregated. The centromere accomplishes this by attaching, via centromere-associated proteins, to the spindle fibers during mitosis and meiosis, thus ensuring proper gene segregation during cell divisions.

To date, the most extensive and reliable characterization of centromere sequences has come from studies of lower eukaryotes such as *S. cerevisiae* and *S. pombe*, where the ability to analyze centromere functions has provided a clear picture of the desired DNA sequences. None of the essential components identified in unicellular organisms, however, function in higher eukaryotic systems. This has seriously hampered efforts to produce artificial chromosomes in higher organisms.

Genetic characterization of centromeres has relied primarily on segregation analysis of chromosome fragments, and in particular on analysis of trisomic strains that carry a genetically marked, telocentric fragment (for example, see Koornneef 1983). This approach is imprecise, however, because a limited set of fragments can be obtained, and because normal centromere function is influenced by surrounding chromosomal sequences (for example, see Koornneef, 1983).

A more precise method for mapping centromeres that can be used in intact chromosomes is tetrad analysis (Mortimer et al., 1981), which provides a functional definition of a centromere in its native chromosomal context. However, the technique is currently limited to a small number of organisms and is relatively labor intensive (Preuss 1994, Smyth 1994). To date, among higher plants, the technique has only been used successfully in *Arabidopsis* (Copenhaver, 1999).

Another avenue of investigation of centromeres has been study of the proteins that are associated with centromeres (Bloom 1993; Earnshaw 1991). Human autoantibodies that bind specifically in the vicinity of the centromere have facilitated the cloning of centromere-associated proteins (CENPs, Rattner 1991). Yeast centromere-associated proteins also have been identified, both through genetic and biochemical studies (Bloom 1993; Lechner et al., 1991).

Despite the aforementioned methods of analysis, the centromeres of most organisms remain poorly defined. Although repetitive DNA fragments mapping both cytologically and genetically to centromeric regions in plants and other higher eukaryotes have been identified, little is known regarding the functionality of these sequences (see Richards et al., 1991; Alfenito et al., 1993; and Maluszynska et al., 1991). Many of these sequences are tandemly-repeated satellite elements and dispersed repeated sequences in series of repeats ranging from 300 kB to 5000 kB in length (Willard 1990). Whether repeats themselves represent functional centromeres remains controversial, as other genomic DNA is required to confer inheritance upon a region of DNA (Willard, 1997).

One characteristic of centromeres which is not well understood is the methylation of cytosines at the carbon 5 position (Martinez-Zapater et al., 1986; Maluszynska and Heslop-Harrison, 1991; Vongs et al., 1993). Methylation is a characteristic feature of many eukaryotic genomes and has been shown to be correlated with heterochromatic regions including regions of repetitive DNA and centromeres (Martienssen and Richards, 1995; Ng and Bird, 1999).

The genomes of both animals and plants contain cytosine methylation, with overall levels of CpG modification often reaching 60 to 90% (Jones and Wolffe, 1999; Gruenbaum et al., 1981). In euchromatin, DNA methylation is concentrated in small regions such as CpG islands and provides epigenetic modifications that regulate genome imprinting, gene expression, and DNA repair (Robertson and Jones, 2000; Singer et al., 2001). In contrast, the role of the extensive DNA methylation found in repetitive, heterochromatic portions of the genome is less clear. In some cases, this methylation reduces recombination; in others, it may play a structural role (J. Bender, 1998; Vongs et al., 1993; Yoder et al., 1997).

A means that has been utilized to study the distribution of methylation in genomes is the use of methylation sensitive restriction endonucleases either alone or in combination with isoschizomeric restriction endonucleases lacking sensitivity to methylation (Jeddeloh and Richards, 1996). An example of such an isoschizomeric pair is HpaII and MspI, which both cut the sequence 5'-C/CGG-3', but each enzyme differs in its sensitivity to cytosine methylation (Butkus et al., 1987; McClelland et al., 1994). Such analyses involving methylation have often been directed to the sparsely methylated portion of genomes, which comprises the majority of coding sequences.

While the above studies have been useful in helping to elucidate the structure and function of centromeres, they have failed to provide an efficient method for cloning centromere nucleic acid sequences. The development of such methods could allow the isolation of centromeres from a broad variety of organisms, potentially allowing the creation of artificial chromosome vectors tailored to numerous economically important species. Such a technique would avoid the need for costly methodologies described by the prior art and represent a significant advance in biotechnology research.

SUMMARY OF THE INVENTION

In one aspect of the invention, a method is provided for obtaining a centromere nucleic acid sequence from a selected species. The method may comprise the steps of: a) preparing a first sample of genomic DNA from a selected species; b) obtaining a plurality of methylated nucleic acid segments from the genomic DNA; and c) screening the methylated nucleic acid segments to identify a centromere nucleic acid sequence. In the method, obtaining may comprise any method of preparing a collection of methylated nucleic acid segments, including contacting genomic DNA with a methylation sensitive nuclease and selecting nucleic acid segments exhibiting resistance to cleavage with the methylation sensitive restriction endonuclease to obtain the plurality of methylated nucleic acid segments. Obtaining methylated DNA may also comprise use of an antibody specific to methylated DNA, for example, by immunoprecipitating methylated nucleic acid segments with an antibody capable of specifically binding methylated DNA or associated proteins.

In another aspect of the invention, the method for obtaining a centromere nucleic acid sequence from a selected species may be further defined as comprising labeling at least a first methylated nucleic segment from a plurality of methylated nucleic acid segments, hybridizing the first methylated nucleic segment to a clone comprising genomic DNA of a selected species and detecting the labeling to obtain a clone comprising a centromere nucleic acid sequence. In the method for obtaining a centromere nucleic acid sequence from a selected species, screening may comprise using an array, for example, in a method comprising the steps of: (i) obtaining an array comprising cloned genomic DNA from the selected species; (ii) detecting a candidate centromere nucleic acid sequence from the cloned genomic DNA of the array, where the candidate centromere nucleic acid sequence comprises a nucleic acid sequence complementary to a nucleic acid sequence of at least a first member of the plurality of methylated nucleic acid segments; and (iii) identifying a centromere nucleic acid sequence from the candidate centromere sequence.

In yet another aspect of the invention, the method for obtaining a centromere nucleic acid sequence from a selected species may comprise detecting a plurality of candidate centromere nucleic acid sequences from an array, where the candidate centromere nucleic acid sequences comprise nucleic acid sequences complementary a nucleic acid sequence of at least a first member of the plurality of methylated nucleic acid segments. An array used with the invention may comprise potentially any target nucleic acid sequences, including cloned genomic DNA. The array may also comprise nucleic acids attached to a solid support. In one embodiment of the invention, the array may comprise cloned genomic DNA attached to a solid support in any selected pattern, including a grid. The cloned genomic DNA may be from any type of clone, including a bacterial artificial chromosome or yeast artificial chromosome clone. Potentially any suitable solid support may be used with the array, including, a microscope slide or hybridization filter.

Detecting nucleic acids in accordance with the invention may comprise use of any suitable label. For example, in the method of obtaining a centromere nucleic acid sequence, the detecting may comprise fluorescently labeling a plurality of methylated nucleic acid segments and hybridizing the labeled plurality of methylated nucleic acid segments to an array. Alternatively, detecting may comprise labeling the plurality of methylated nucleic acid segments with an antigen, hybridizing the labeled plurality of methylated nucleic acid segments to an array and detecting the antigen with a molecule which binds the antigen. Labeling probes may comprise radioactively labeling a plurality of methylated nucleic acid segments and hybridizing the labeled plurality of methylated nucleic acid segments to an array. An array used with the invention may comprise a plurality of DNA pools, the pools comprising the nucleic acid sequences of at least a first and a second clone comprising genomic DNA from a selected species.

In still yet another aspect of the invention, methylated nucleic acid segments may be obtained by a method comprising (i) obtaining a second sample of genomic DNA from a selected species; (ii) contacting the second sample of genomic DNA with an isoschizomer of a methylation sensitive restriction endonuclease, wherein the isoschizomer is not methylation sensitive; (iii) resolving separately first and second samples of genomic DNA following the contacting with the isoschizomer and the methylation sensitive restriction endonuclease; and (iv) selecting a plurality of methylated nucleic acid segments from at least a first nucleic acid fraction present in the first sample of genomic DNA and not present in the second sample of genomic DNA. The method may further comprise contacting the second sample of genomic DNA with a methylation sensitive restriction endonuclease. Any methylation sensitive restriction endonuclease may potentially be used with the invention, including, for example, AatII, AciI, AgeI, AhaII, AscI, AvaI, BsaAI, BsaHI, BsiEI, BsiWI, BspDI, BsrFI, BssHII, BstBI, BstUI, Cfr10I, ClaI, EagI, Eco47III, Esp3I, FseI, FspI, HaeII, HgaI, HhaI, HinPII, HpaII, KasI, MluI, NaeI, NarI, NgoMIV, NotI, NruI, PmlI, Psp1406I, PvuI, RsrII, SacII, SalI, SmaI, SnaBI, TaiI, and XhoI. Alternatively, a non-methylation sensitive restriction endonuclease may be used with the invention, including, for example, BamHI, BanII, BbsI, BsaJI, BsaWI, BsmI, Bspl286I, BspEI, BspMI, BsrBI, BstEII, BstYI, Csp6I, Eaml105I, EarI, Eco0I09I, EcoRI, EcoRV, FokI, HaeIII, HgiAI, HphI, KpnI, MspI, PaeR7I, PmeI, SacI, SfaNI, SphI, TaqI, TfiI, Tth111I, and XmaI.

In still yet another aspect of the invention, methylated nucleic acid segments may be obtained by a method comprising determining the resistance of the methylated nucleic acid segments to restriction based on the length of the methylated nucleic acid segments following contacting with a methylation sensitive restriction endonuclease. In the method, the average length of the plurality of methylated nucleic acid segments may be at least 3 kb, 4 kb, 5 kb, 7 kb, 8 kb, or at least 10 kb, or another length determined to represent the fraction of methylated nucleic acid segments.

In still yet another aspect, the method of obtaining a centromere nucleic acid sequence from a selected species may be further defined as comprising obtaining a plurality of unmethylated nucleic acid segments and comparing the plurality of unmethylated nucleic acid segments to a plurality of methylated nucleic acid segments to identify at least a first methylated nucleic acid segment present in the plurality of methylated nucleic acid segments and not present in the plurality of unmethylated nucleic acid segments. The method may be further defined as comprising hybridizing a plurality of unmethylated nucleic acid segments to one or both of a first methylated nucleic acid segment or a clone comprising genomic DNA of a selected species, wherein the plurality of unmethylated nucleic acid segments have not received labeling. In the method, obtaining a plurality of unmethylated nucleic acid segments may comprise identifying a plurality of nucleic acid sequences which are susceptible to restriction with a methylation sensitive restriction endonuclease. The method may be further defined as comprising measuring an average length of the plurality of unmethylated nucleic acid segments following restriction with the methylation sensitive restriction endonuclease. In certain embodiments of the invention, the average length of the plurality of unmethylated nucleic acid segments may be less than about 5 kb, 4 kb, 3 kb, 2 kb or about 1 kb or smaller following restriction with the methylation sensitive restriction endonuclease.

In still yet another aspect of the invention, in the method for obtaining a centromere nucleic acid sequence from a selected species, the selected species may be further defined as a plant, including a dicotyledonous plant or a mammal, such as a human. Examples of dicotyledonous plants include tobacco, tomato, potato, sugar beet, pea, carrot, cauliflower, broccoli, soybean, canola, sunflower, alfalfa, cotton and *Arabidopsis*. In certain further embodiments, the dicotyledonous plant is not *Arabidopsis*. The plant may also be a monocotyledonous plant, including wheat, maize, rye, rice, turfgrass, oat, barley, sorghum, millet, and sugarcane.

In still yet another aspect of the invention, the method for obtaining a centromere nucleic acid sequence from a selected species may comprise screening to identify a candidate centromere sequence not comprising repetitive DNA.

In still yet another aspect of the invention, the step of contacting in the method for obtaining a centromere nucleic acid sequence from a selected species may comprise: (i) incubating the genomic DNA with a methylation sensitive restriction endonuclease to digest unmethylated DNA; (ii) resolving digested genomic DNA from undigested genomic DNA by electrophoresis; and (iii) isolating a plurality of methylated nucleic acid segments from the undigested genomic DNA. In the method, the average length of the plurality of methylated nucleic acid segments may be at least about 3 kb, 4 kb, 5 kb 7 kb, 8 kb, or at least 10 kb, or another length determined to represent the fraction of methylated nucleic acid segments.

In still yet another aspect of the invention, the method for obtaining a centromere nucleic acid sequence from a selected species may comprise fluorescent in situ hybridization of at least a first methylated nucleic acid segment from the plurality of methylated nucleic acid segments. The method may also comprise determining the nucleic acid sequence of at least a first methylated nucleic acid segment from the plurality of methylated nucleic acid segments. The method may still further comprise comparing the nucleic acid sequence of the first methylated nucleic acid segment to a known centromere sequence. In another embodiment of the invention, comparing may comprise immunoprecipitating a centromere nucleic acid sequence and comparing the sequence to the nucleic acid sequence of the first methylated nucleic acid segment. This may comprise immunoprecipitating the centromere nucleic acid sequences with an antibody capable of binding methylated DNA. Alternatively, this may comprise immunoprecipitating the centromere nucleic acid sequences with an antibody capable of binding a centromere-associated protein.

In still yet another aspect of the invention, the method for obtaining a centromere nucleic acid sequence from a selected species may comprise genetically mapping at least a first methylated nucleic acid segment from the plurality of methylated nucleic acid segments.

In still yet another aspect of the invention, the method for obtaining a centromere nucleic acid sequence from a selected species may comprise determining the extent of acetylation of at least a first histone bound to at least a first methylated nucleic acid segment from the plurality of methylated nucleic acid segments.

In still yet another aspect of the invention, the method for obtaining a centromere nucleic acid sequence from a selected species may comprise transforming a cell with at least a first methylated nucleic acid segment from the plurality of methylated nucleic acid segments. The cell may be transformed with the methylated nucleic acid segment.

The cell may be further defined as integratively or non-integratively transformed with the methylated nucleic acid segment. The nucleic acid segment may or may not be methylated when it is transformed in the organism and may still further be defined as remethylated. Screening may comprise observing a phenotypic effect present in the integratively transformed cells or whole organisms comprising the cells, wherein the phenotypic effect is absent in a control cell not integratively transformed with the methylated nucleic acid segment, or an organism comprising the control cell. The phenotypic effect may be selected from the group consisting of reduced viability, reduced efficiency of transforming, genetic instability in the integratively transformed nucleic acid, aberrant tissue sectors, increased ploidy, aneuploidy, and increased integrative transformation in distal or centromeric chromosome regions.

In still yet another aspect of the invention, in the method for obtaining a centromere nucleic acid sequence from a selected species, a first methylated nucleic acid segment may be further defined as comprising a recombinant construct. The recombinant construct may comprise any additional selected elements, including an autonomous replicating sequence (ARS), a structural gene, and a selectable or screenable marker gene.

In still yet another aspect of the invention, a centromere nucleic acid sequence is provided which has been prepared by a method for obtaining a centromere nucleic acid sequence from a selected species in accordance with the invention. Further provided by the invention, is an organism or cell transformed in accordance with the invention, as well as a progeny of any generation of such an organism, the organism comprising the first methylated nucleic acid segment.

In still yet another aspect of the invention, a method of obtaining a centromere nucleic acid sequence from a selected organism is provided, the method comprising the steps of: a) preparing a first sample of genomic DNA from a selected organism; b) contacting said genomic DNA with a strand-specific methylation sensitive restriction endonuclease; c) nick-translating the genomic DNA; and c) detecting a centromere nucleic acid sequence that hybridizes to the nick-translated genomic DNA. In one embodiment of the invention, the strand-specific methylation sensitive restriction endonuclease is selected from the group consisting of HpaI, KpnI, MaeII, and Sau3A.

The method of detecting may comprise screening an array. Use of such an array may comprise the steps of a) obtaining an array comprising cloned genomic DNA from said selected organism; and b) detecting a centromere nucleic acid sequence from said cloned genomic DNA of said array by hybridizing the nick translated genomic DNA to said array. In one embodiment of the invention, a plurality of centromere nucleic acid sequences are detected from said array. The array may comprise the cloned genomic DNA attached to a solid support. The array may or may not comprising the cloned genomic DNA attached in a selected pattern, such as a grid. Any cloned genomic DNA could be used, such as from a bacterial artificial chromosome or yeast artificial chromosome clone. Any solid support can be used, such as a microscope slide or hybridization filter. In one embodiment of the invention, the array comprises a plurality of DNA pools, the pools comprising the nucleic acid sequences of at least a first and a second clone comprising genomic DNA from a selected organism.

Contacting may, in certain embodiments of the invention, be further defined as comprising a) obtaining a second sample of genomic DNA from said selected organism; b)

contacting said second sample of genomic DNA with an isoschizomer of said strand-specific methylation sensitive restriction endonuclease, wherein said isoschizomer is not a strand-specific methylation sensitive restriction endonuclease; c) resolving separately said first and said second samples of genomic DNA following said contacting; and d) selecting a plurality of hemimethylated nucleic acid segments from at least a first nucleic acid fraction present in said first sample of genomic DNA and not present in said second sample of genomic DNA. Any suitable labeling can be used with the nick-translating, including use of radioactive labeling, labeling the genomic DNA with an antigen and labeling the genomic DNA with a fluorophore.

In certain embodiments of the invention, the selected organisms used with the method is a plant. The plant may be a dicotyledonous plant, including tobacco, tomato, potato, sugar beet, pea, carrot, cauliflower, broccoli, soybean, canola, sunflower, alfalfa, cotton and *Arabidopsis*. The plant can also be a monocotyledonous plant, including wheat, maize, rye, rice, turfgrass, oat, barley, sorghum, millet, and sugarcane. Alternatively, the selected organism is a mammal, including a human.

In certain embodiments of the invention, the method is further defined as comprising fluorescent in situ hybridization of the centromere nucleic acid sequence, and may also comprise determining the nucleic acid sequence of the centromere nucleic acid sequence. In further embodiments, the method comprises comparing the nucleic acid sequence of the centromere nucleic acid sequence to a known centromere sequence. In still further embodiments, the method comprises transforming a cell with the centromere nucleic acid sequence, either integratively or non-integratively, with the centromere nucleic acid sequence. The method may also comprise screening for a phenotypic effect present in the integratively transformed cells or an organism comprising the cells, wherein said phenotypic effect is absent in a control cell not integratively transformed with said centromere nucleic acid sequence or an organism comprising said control cell. Examples of phenotypic effects that could be screened include reduced viability, reduced efficiency of said transforming, genetic instability in the integratively transformed nucleic acid, aberrant tissue sectors, increased ploidy, aneuploidy, and increased integrative transformation in distal or centromeric chromosome regions.

The centromere nucleic acid sequence can be transformed alone, or may be on a recombinant construct, including fragments thereof. The centromere nucleic acid sequence may also be further defined as comprising cloned DNA. The cloned DNA may or may not be methylated, for example, because methylation may be lost following cloning. The cloned DNA may also be remethylated prior to transforming, and may also be defined as hemimethylated. The recombinant DNA may or may not include any other desired elements, including one or more telomere, an autonomous replicating sequence (ARS), structural gene, and selectable or screenable marker gene.

In still yet another aspect, the invention provides a centromere nucleic acid sequence prepared by any of the foregoing methods. Also proveded are a non-human organism prepared by such methods, as well as a progeny of any generation of such an organism.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A, 1B. Strand-specific methylation of centromeric DNA sequences. (FIG. 1A) Sequence chromatogram from CEN5 (Copenhaver et al., 1999). The unmodified wild-type sequence (middle) is compared to sequences generated by bisulfite treatment (top and bottom); unmethylated cytosines (arrows) and cytosines protected by methylation (shading) are indicated. (FIG. 1B) Independent sequences (upper and lower strands) of a 240 bp CEN2 fragment amplified from bisulfite-treated DNA (Copenhaver et al., 1999). For the analysis, 10 ug of seedling genomic DNA was sheared into 1–2 kb fragments, denatured in 0.1 M NaOH (15 min, 20° C.), neutralized and ethanol precipitated. Non-methylated cytosines were deaminated in 1.2 ml of 4M $NaHSO_3$, 500 µM hydroquinone, pH 5.0 at 50° C. for 24 hrs. DNA was purified on a gel filtration column, incubated in 0.3 M NaOH (10 min, 20° C.), and ethanol precipitated. Black boxes indicate the position of cytosines in the original sequence.

(FIG. 2A) DNA sequences are numbered 1–20 as in Table 1; circles, regions with significantly different methylation levels between the two complementary strands. (FIG. 2B) Abundance of hemi-methylated Sau3A I sites along the 255 BAC and P1 clones in the sequenced tiling path; gaps correspond to portions of the chromosome that have not been sequenced (The *Arabidopsis* Genome Initiative, Nature 408, 796, 2000; Lin et al., 1999). Levels of nick translation products following a Sau3A I digest are reported relative to Mbo I-digested genomic DNA. Quantitation was performed with Imagequant software (Molecular Dynamics).

(FIG. 4A) Each centromeric region is drawn to scale and indicated by the shaded box; physical sizes are derived from DNA sequencing (chromosomes II and IV) or from estimates based on BAC fingerprinting (Marra et al., 1999; Mozo et al., 1999) (chromosomes I, III, and V). Indicated for each chromosome are positions of markers (above), the number of tetratype/total tetrads at those markers (below), the boundaries of the centromere (black circles), and the name of contigs derived from fingerprint analysis (Marra et al., 1999; Mozo et al., 1999). For each contig, more than two genetic markers, developed from the database of BAC-end sequences (http://www.tigr.org/tdb/at/abe/bac_end_search.html) were scored. PCR primers corresponding to these sequences were used to identify size or restriction site polymorphisms in the Columbia and Landsberg ecotypes (Bell and Ecker, 1994; Konieczny and Ausubel, 1993); primer sequences are available (http://genome-www.stanford.edu/*Arabidopsis*/aboutcaps.html). Tetratype tetrads resulting from treatments that stimulate crossing over (boxes); positions of markers in centimorgans (cM) shared with the recombinant inbred (RI) map (ovals) (http://nasc.nott.ac.uk/new_ri_map.html; Somerville and Somerville, 1999); and sequences bordering gaps in the physical map that correspond to 180 bp repeats (open circles) (Round et al., 1997), 5S rDNA (black circles) or 160 bp repeats (gray circles) are indicated (Copenhaver et al., 1999). (FIG. 4B) Shows centromere regions denoted in FIG. 4A with regions corresponding to clones identified through isolation of methylated DNA, as described in Example 3, indicated by the thick black bar within the shaded centromere regions. The comparative and subtractive methods described in Example 3 identified the clones indicated by the thick black bars, all of which were located in the centromere. The subtractions and/or comparisons described in the example eliminated nearly all non-centromere clones, which comprised approximately 50%–70% of the initial selection of clones detected by hybridization to methylated DNA, giving a yield of centromere sequence containing clones approaching 100% with use of stringent selection criteria.

FIG. 7. Method for analysis of dicentric chromosomes in *Arabidopsis*. BiBAC vectors containing centromere fragments (~100 kb) are integrated into the *Arabidopsis* genome using *Agrobacterium*-mediated transformation procedures and studied for adverse affects due to formation of dicentric chromosomes. 1) BiBACs containing centromere fragments are identified using standard protocols. 2) Plant transformation. 3) Analysis of defects in growth and development of plants containing dicentric chromosomes.

(FIG. 8A) Shows a sample set of BAC clones identified by probing with fragments less than 5 kb in size following digestion of *Arabidopsis* genomic DNA with the methylation-sensitive endonuclease HpaII. During hybridization, unlabeled methylated DNA fragments (the fraction over 10 kb in size after cutting with HpaII) was included with the probe mixture. (FIG. 8B) The same filter region as in FIG. 8A but probed with fragments corresponding to highly methylated DNA (the probe was made from the fraction greater than 10 kb in size after cutting with HpaII). Some clones were identified by both methods. Desirable as candidate centromeric clones were those that yielded a stronger signal when probing with methylated DNA fragments as compared to the non-methylated fraction.

FIG. 9. List of centromeric BACs identified as described in Examples 3 and 4. A screen for centromere-containing clones was carried out as described in Examples 3 and 4. The identity of BACs detected with methylated DNA was determined based on filter signal position (column 2). The BAC clones were assigned to previously assembled contigs based on their identity (column 1) (see Marra et al., 1999). The signal from separate hybridizations with both labeled methylated genomic DNA (column 3) and labeled unmethylated genomic DNA (column 4) labeled was manually scored as dark (D), medium (M), or light (L). Hybridizations were also carried out using as a probe DNA of 180 bp repeats, a series of repeats that are know to reside in *Arabidopsis* centromeres (X) (column 5). The results show a number of clones that were identified in centromere regions but that did not contain 180 bp repeats. Repetitive DNA that is non-centromeric can be labeled by both the methylated and non-methylated fraction. Effective blocking of these signals may be carried out, for example, by including unlabeled repetitive DNA with the probe, or by subtracting clones hybridizing to the methylated and unmethylated fractions.

FIG. 10. Representative sample of hybridization data. 1) Selected clones from list in FIG. 9 show that methylated DNA corresponding to centromeric clones may be identified both containing or not containing 180 bp repeats known to be present at centromeres in *Arabidopsis*. 2) Clones shown to contain rDNA repeats are indicated. As can be seen, rDNA containing clones may be from methylated portions of the genome. Signals from repeats such as rDNA may be blocked as described herein below. 3) Although 180 bp repeats were found in many centromeric clones, non-methylated DNA containing sequences were also identified that contained the 180 bp repeat DNA. Thus, it may be desirable to carry out studies in which the 180 bp repeat is not probed for. For example, it may be desired to use subtractions, competitive hybridizations or other techniques to eliminate signal from the 180 bp repeats.

FIG. 13. Assay of chromosome stability. The stability of natural chromosomes, constructed minichromosome, or dicentric chromosomes can be assessed by monitoring the assortment of color markers through cell division. The markers are linked to the centromere in modified BAC or BiBAC vectors and introduced into cells. Regulation of the marker gene by an appropriate promoter determines which tissues will be assayed. For example, root-specific promoters, such as SCARECROW make it possible to monitor assortment in files of root cells; post-meiotic pollen-specific promoters such as LAT52 allow monitoring of assortment through meiosis, and general promoters such as the 35S Cauliflower mosaic virus promoter make it possible to monitor assortment in many other tissues. Qualitative assays assess the general pattern of stability and measure the size of sectors corresponding to marker loss, while quantitative assays require knowledge of cell lineage and allow the number of chromosome loss events to be calculated during mitosis and meiosis.

DETAILED DESCRIPTION OF THE INVENTION

Figures 2A, 2B:
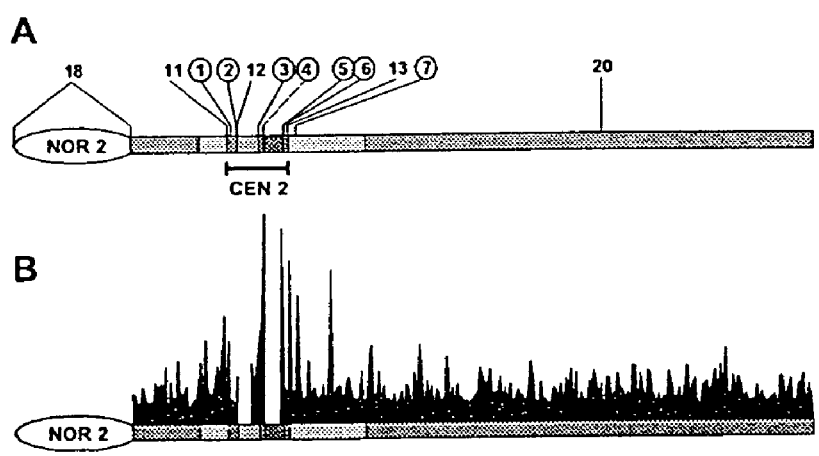
FIG. 2A, 2B. Distribution of methylation on chromosome 2 in *Arabidopsis*. Scale drawing depicting the rDNA cluster (NOR2), the centromere (CEN2), pericentromeric regions, an insertion of the mitochondrial genome, and the 180 bp series of repeats (The *Arabidopsis* Genome Initiative, Nature 408, 796, 2000).

The invention overcomes the deficiencies of the prior art by providing an efficient method for the isolation of centromeres. The invention overcomes limitations in the prior art by eliminating the need for costly genetic mapping programs or imprecise cytological techniques for the isolation of centromeres. In particular, the current invention provides efficient techniques for the isolation of centromere sequences by way of an initial isolation of methylated centromere sequences or of sequences associated with centromere-specific proteins. Through use of the techniques of the invention in the model plant organism *Arabidopsis thaliana*, the inventors were able in several days to obtain an initial collection of approximately 2695 bacterial artificial chromosome (BAC) clones of which as many as 30–50% were subsequently shown to comprise centromere DNA. This is in marked contrast to the approximate 3 year mapping program expected for the genetic mapping of a centromere (see, e.g., Copenhaver et al. 1997, 1999). Using stringent scoring criteria, including comparison of signal obtained by separate hybridizations to methylated and unmethylated nucleic acid segments, the proportion of identified clones containing centromere sequences approached 100% (Examples 3 and 4).

I. Isolation of Centromere Nucleic Acids

An advantage of the invention is that it allows centromere sequences to be rapidly obtained without the need for genetic mapping or other costly mapping techniques. In the technique, methylated nucleic acid segments could be isolated by potentially any method. Two efficient methods for the isolation comprise use of antibodies specific for methylated nucleic acids and, particularly, methods exploiting the resistance of methylated centromeric DNA to cleavage with methylation sensitive restriction endonucleases. The methylated nucleic acid segments obtained by such techniques will generally comprise methylated bases at a frequency which is greater than that of the average nucleic segment in the target organism. In certain embodiments of the invention, methylated nucleic acid segments prepared in accordance with the invention may comprise a frequency of methylated bases which places the given methylated nucleic acid segment among about the $51^{st}$, $55^{th}$, $60^{th}$, $70^{th}$, $80^{th}$, $90^{th}$, $95^{th}$, $98^{th}$, $99^{th}$, or $99.9^{th}$ percentile for extent of methylation of bases relative to a random selection of nucleic acid segments of comparable size from the genome of the target organism, up to and including, complete methylation of a given methylated nucleic acid segment or collection of methylated nucleic acid segments. In further embodiments of the invention, methylated nucleic acid segments comprise a mean size following restriction endonuclease digestion that is larger than the mean for the genomic DNA of the organisms from which the methylated nucleic acid segments were obtained.

Isolated methylated DNA fragments can be further screened to identify candidate centromere sequences. For example, by first digesting genomic DNA with a methylation sensitive restriction endonuclease, methylated DNA fragments may be isolated in the undigested fraction of DNA. In another embodiment, antibodies specific for methylated DNA can be used to purify or immunoprecipitate methylated DNA fragments. The methylated DNA fragments can then be labeled and used to isolate a large number of bacterial artificial chromosome clones. In certain embodiments of the invention, the clones may be part of a library that is comprised in an array, thereby allowing efficient screening and scoring of hits, as well as the comparison of multiple data layers that may be obtained during the screening for centromere sequences.

In accordance with the methods of the invention, the collection of candidate centromere sequences obtained may be narrowed to increase the likelihood that they contain centromere sequences. In one embodiment of the invention, this may comprise subtracting members of the population of unmethylated DNA from the population of methylated DNA. This could be achieved, for example, by including unlabeled unmethylated DNA with the labeled methylated DNA during the identification of candidate centromere sequences, thereby helping to ensure that the candidate clones represent only those sequences unique to methylated portions of the target genome.

An efficient embodiment of the invention comprises the hybridization of labeled methylated DNA fractions to arrays comprising a library of genomic DNA clones. In this way, clones containing candidate centromere sequences can be rapidly identified from the target genome. The list of candidate centromere sequences can be rapidly refined through subsequent hybridizations. For example, further refinement of the sample of methylated sequences can be made by removing those sequences that were detected as a result of background due to repetitive sequences. This may be particularly desirable in view of studies suggesting that some non-centromere DNA is methylated. One technique for this would be to separately hybridize a fraction of labeled total genomic, or repetitive DNA-enriched genomic DNA (for example, DNA of ribosomal RNA genes) to the same collection of genomic clones as was hybridized with the fraction of methylated DNA segments. Those sequences giving strong signal upon hybridization with the genomic DNA or repetitive DNA could then be removed from the population of candidate centromere sequences, as the signals obtained may be attributable to hybridization to non centromeric repetitive sequences. The desired collection of candidate centromere sequences will include those candidates that hybridize strongly to the methylated DNA fraction but not to non-centromeric repetitive DNA.

Removal of background from repetitive DNA could also be achieved by way of competitive hybridizations. For example, an excess of unlabeled total genomic DNA may be added to the labeled methylated DNA fragments prior or during isolation of the candidate centromere sequences. The unlabeled repetitive sequences would be expected to be present in higher proportion relative to the low-copy DNA and thus would be expected to be blocked by homologous sequences present in the methylated DNA fraction more efficiently than would lower-copy sequences. Alternatively, such a competitive hybridization could be carried out using unlabeled DNA enriched for repetitive elements, such as a Cot-1 DNA fraction, the fraction that most rapidly re-anneals when single stranded DNA is in solution.

A. Hybridizations

For detection of centromere sequences, methylated DNA segments will preferably be greater than 5 kb in length and still more preferably greater than 10 kb in length following restriction with a methylation sensitive restriction endonuclease. However, once the methylated DNA segments have been isolated, it may be preferable to prepare smaller probe fragments. In one embodiment of the invention, probes are generated by using random oligonucleotides (for example, 6 mers) as primers to amplify labeled fragments of the methylated DNA segments. In other embodiments of the invention, the use of a probes or primers of between 13 and 100 nucleotides, preferably between 17 and 100 nucleotides in length, or in some aspects of the invention up to 1–2 kilobases or more in length, allows the formation of a duplex molecule that is both stable and selective. Molecules having complementary sequences over contiguous stretches greater than 20 bases in length are generally preferred, to increase stability and/or selectivity of the hybrid molecules obtained. One will generally prefer to use nucleic acid molecules for hybridization having one or more complementary sequences of 20 to 30 nucleotides, or even longer where desired. Such sequences may correspond to an isolated plurality of methylated nucleic acid segments isolated from size-fractionated DNA and then labeled.

Accordingly, nucleic acid sequences prepared with the invention may be used for their ability to selectively form duplex molecules with complementary stretches of DNAs and/or RNAs or to provide primers for amplification of DNA or RNA from samples. Depending on the application envisioned, one would desire to employ varying conditions of hybridization to achieve varying degrees of selectivity of the probe or primers for the target sequence.

For applications requiring high selectivity, one will typically desire to employ relatively high stringency conditions to form the hybrids. For example, relatively low salt and/or high temperature conditions, such as provided by a high stringency hybridization buffer such as 7% SDS in 0.5 M NaPO$_4$, 1% BSA, 1 mM EDTA and 10 μg salmon sperm DNA, or alternatively, about 0.02 M to about 0.10 M NaCl at temperatures of about 50° C. to about 70° C. This may be followed by a wash in 2×SSC buffer in 1% SDS. Such high stringency conditions tolerate little, if any, mismatch between the probe or primers and the template or target strand and would be particularly suitable for isolating specific single copy nucleic acid sequences. It is generally appreciated that conditions can be rendered more stringent by the addition of increasing amounts of formamide.

In other embodiments of the invention, hybridization may be achieved under conditions of, for example, 50 mM Tris-HCl (pH 8.3), 75 mM KCl, 3 mM MgCl$_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM MgCl$_2$, at temperatures ranging from approximately 40° C. to about 72° C.

In certain embodiments, it will be advantageous to employ nucleic acids, including methylated and unmethylated nucleic acids, in combination with an appropriate means for determining hybridization, such as a label. A wide variety of appropriate indicator means are known in the art, including fluorescent, radioactive (e.g., $^{32}P$), enzymatic or other ligands, such as avidin/biotin, which are capable of being detected. In certain embodiments, one may desire to employ a fluorescent label or an enzyme tag such as urease, alkaline phosphatase or peroxidase, instead of radioactive or other environmentally undesirable reagents. In the case of enzyme tags, calorimetric indicator substrates are known that can be employed to provide a detection means that is visibly or spectrophotometrically detectable, to identify specific hybridization with complementary nucleic; acid containing samples.

In general, it is envisioned that the nucleic acid sequences and derivatives thereof provided by the invention will be useful as reagents in solution hybridization for detection of centromere sequences. In embodiments involving a solid phase, the test DNA (or RNA) is adsorbed or otherwise affixed to a selected matrix or surface. This fixed, single stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663; 5,900,481 and 5,919,626. Other methods of hybridization that may be used in the practice of the present invention are disclosed in U.S. Pat. Nos. 5,849,481; 5,849,486 and 5,851,772. The relevant portions of these and other references identified in this section of the Specification are incorporated herein by reference.

B. Detection of Nucleic Acids

Following isolation of nucleic acids, it may be desirable to separate the nucleic acids according to size. Such an isolation represents an efficient technique for the isolation of methylated nucleic acid segments. In one embodiment of the invention, the separation may be carried out by use of agarose, agarose-acrylamide or polyacrylamide gel electrophoresis using standard methods (Sambrook et al., 1989). Separated nucleic acids may be cut out and eluted from the gel for further manipulation. In one embodiment of the invention, this may be achieved using a Qiagen kit or β-agarose digestion. Using low melting point agarose gels, the separated band may be removed by heating the gel, followed by extraction of the nucleic acid.

Separation of nucleic acids may also be effected by chromatographic techniques known in art. There are many kinds of chromatography that may be used in the practice of the present invention, including adsorption, partition, ion-exchange, hydroxylapatite, thin-layer, and gas chromatography as well molecular sieve, reverse-phase, column, paper, as HPLC.

In certain embodiments, the separated nucleic acids are visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to X-ray film or visualized under the appropriate excitatory spectra.

In particular embodiments of the invention, detection is by Southern blotting and hybridization with a labeled probe. The techniques involved in Southern blotting are well known to those of skill in the art (see Sambrook et al., 1989). One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,8,53,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

C. Amplification of Nucleic Acids

In certain embodiments of the invention, amplification techniques could be used. For example, methylated nucleic acid sequences or fragments of such nucleic acids could be used as primers in order to amplify centromere sequences flanking the primer. These centromere sequences could then be cloned. Nucleic acids used as a template for amplification may be isolated from cells, tissues or other samples according to standard methodologies (Sambrook et al., 1989). In certain embodiments, analysis is performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double stranded and/or single-stranded form, although the single-stranded form is preferred.

Depending upon the desired application, high stringency hybridization conditions may be selected that will only allow hybridization to sequences that are completely complementary to the primers. In other embodiments, hybridization may occur under reduced stringency to allow for amplification of nucleic acids contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Affymax technology; Bellus, 1994).

A number of template dependent processes are available to amplify nucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in their entirety.

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR™ and oligonucleotide ligase assay (OLA), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Qbeta Replicase, described in PCT Application No. PCT/US87/00880, may also be used as an amplification method in the present invention. In this method, a replicative sequence of RNA that has a region complementary to that of a target is added to a sample in the presence of an RNA polymerase. The polymerase will copy the replicative sequence that may then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated herein by reference in their entirety). European Application No. 329 822 disclose a nucleic acid amplification process involving cyclically synthesizing single-stranded RNA ("ssRNA"), ssDNA, and double-stranded DNA (dsDNA), which may be used in accordance with the present invention.

PCT Application WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR" (Frohman, 1990; Ohara et al., 1989).

D. Competitive Hybridizations

Use of competitive hybridizations may be desirable in certain embodiments of the invention. Competitive hybridizations may, for example, be used to eliminate potential background from non-centromere repetitive sequences or from other non-centromere sequences. In many instances, repetitive DNA sequences may comprise interspersed repetitive DNA, or for example, tandemly repeated DNA such as DNA encoding ribosomal RNA. Signal from repetitive sequences may be "blocked" by inclusion of unlabeled total genomic DNA in a mixture of labeled probe DNA, or by use of the unlabeled DNA in prehybridizations before application of the labeled probe. Even more effective than total genomic DNA for blocking will be DNA that is "enriched" for repetitive, such as $C_0t$-1 DNA (Zwick et al., 1997), or alternatively, DNA that can be digested into fragments smaller than 3 kb by a methylation sensitive endonuclease.

The proportion of blocking DNA to probe DNA used will vary and will depend on a number of factors, including: the relative proportion of sequences to be blocked in the probe/primer and target sequences, the desired level of sensitivity in the detection, the size of repetitive sequences, and the degree of sequence homology between the probe sequences to be blocked and those of the target. Typical concentrations of unlabeled blocking DNA that may be used include from about 10 to about 200 fold excess, relative to the probe, including about 20, 40, 50, 60, 70, 80, 90, 100, 110, 120, 130, 140, 150, 160, 170, 180, and 190 fold excess. Alternatively, one may wish to use concentrations of blocking DNA greater or lesser than this range, including about 5, 300, 400, 500, 600, 700, 800, 900, or about 1000 fold excess. The optimal concentration used, however, will be dependent on the above mentioned factors and will be known to those of skill in the art in light of the present disclosure.

E. Kits

All the essential materials and/or reagents required for detecting a centromere sequence in a sample of genomic DNA may be assembled together in a kit. This generally will comprise enzymes suitable for modifying the genomic DNA, including restriction endonucleases. The kits may also include means for resolving the digestion products, as well as buffers to provide the necessary reaction mixture. Such kits may also include enzymes and other reagents suitable for detection of specific centromere nucleic acids or amplification products. Such kits generally will comprise, in suitable means, distinct containers for each individual reagent or enzyme.

II. Isolation of Centromere Sequences Using Arrays

One advantage of the invention is that it allows arrays to be employed for the efficient isolation of large numbers of candidate centromere sequences that can then be screened for confirmation as centromeres. In such an array, target nucleic acid sequences may be located so that positive signals at a particular location on the array can be correlated with a particular target sequence. Although the nucleic acids need not be placed at any particular location on the array, it will generally be desired that the location is know such that identified target sequences will be of known identity. Where the nucleic acids are arranged in a precise order, simultaneous screening of potentially thousands of sequences may be facilitated. The use of arrays involves the binding of DNA to known, although not necessarily selected, locations, termed sectors, on a solid support. Through hybridization of a specific probe or primer to the array, such as a plurality of methylated nucleic acid segments, for example, sequences corresponding to the labeled DNA may be identified from the total collection of sequences in the array, and preferably, an entire target genome. The identified clones will therefore be expected to correspond to the methylated regions within the target genome.

The use of arrays can also be coupled with pooling techniques. Pools correspond to numerous clones or other DNA fragments mixed together and placed in a particular location on the array. Use of such pools can greatly decrease the total number of clones required to be screened while still identifying the individual clones containing those sequences.

A. Preparation of Arrays

Many different methods for preparation of arrays of DNA on solid supports are known to those of skill in the art. For example, specific methods for preparing arrays disclosed in: Affinity Techniques, Enzyme Purification: Part B, Meth. Enz. 34 (ed. W. B. Jakoby and M. Wilchek, Acad. Press, N.Y. (1974) and Immobilized Biochemicals and Affinity Chromatography, Adv. Exp. Med. Biol. 42 (ed. R. Dunlap, Plenum Press, N.F. 1974), each of which is specifically incorporated herein by reference in its entirety). Examples of other techniques that have been described include the use of successive application of multiple layers of biotin, avidin, and extenders (U.S. Pat. No. 4,282,287, specifically incorporated herein by reference in its entirety); through methods employing a photochemically active reagent and a coupling agent that attaches the photoreagent to the substrate (U.S. Pat. No. 4,542,102, specifically incorporated herein by reference in its entirety), use of polyacrylamide supports on which are immobilized oligonucleotides (PCT Patent Publication No. 90/07582, specifically incorporated herein by reference in its entirety), through use of solid supports on which oligonucleotides are immobilized via a 5'-dithio linkage (PCT Patent Publication No. 91/00868, specifically incorporated herein by reference in its entirety); and through use of a photoactivateable derivative of biotin as the agent for immobilizing a biological polymer of interest onto a solid support (see U.S. Pat. No. 5,252,743; and PCT Patent Publication No. 91/07087 to Barrett et al., each specifically incorporated herein by reference in its entirety). In the case of a solid support made of nitrocellulose or the like, standard techniques for UV-crosslinking may be of particular utility (Sambrook et al., 1989).

The solid support surface upon which an array is produced may potentially be any suitable substance. Examples of materials that can be used include polymers, plastics, resins, polysaccharides, silica or silica-based materials, carbon, metals, inorganic glasses, membranes, etc. It may also be advantageous to use a surface that is optically transparent, such as flat glass or a thin layer of single-crystal silicon. Contemplated as being especially useful are nylon filters, such as Hybond N+ (Amersham Corporation, Amersham, UK). Surfaces on the solid substrate will usually, though not always, be composed of the same material as the substrate, and the surface may further contain reactive groups, which could be carboxyl, amino, hydroxyl, or the like.

It is contemplated that one may wish to use a surface that is provided with a layer of crosslinking groups (U.S. Pat. No. 5,412,087, specifically incorporated herein by reference in its entirety). Crosslinking groups could be selected from any suitable class of compounds, for example, aryl acetylenes, ethylene glycol oligomers containing 2 to 10 monomer units, diamines, diacids, amino acids, or combinations thereof. Crosslinking groups can be attached to the surface by a variety of methods that will be readily apparent to one of skill in the art. For example, crosslinking groups may be attached to the surface by siloxane bonds formed via reactions of crosslinking groups bearing trichlorosilyl or tris-alkoxy groups with hydroxyl groups on the surface of the substrate. The crosslinking groups can be attached in an ordered array, i.e., as parts of the head groups in a polymerized Langmuir Blodgett film. The linking groups may be attached by a variety of methods that are readily apparent to one skilled in the art, for instance, by esterification or amidation reactions of an activated ester of the linking group with a reactive hydroxyl or amine on the free end of the crosslinking group.

B. Nucleic Acid Compositions for Preparation of Arrays

In certain embodiments of the invention, arrays may comprise clones of genomic DNA from one or more target species. Although potentially any type of clone may be used, a particularly useful type of clone is the bacterial artificial chromosome (BAC), as data has suggested that YAC clones may sometimes not span centromeres (Willard, 1997). The construction and characterization of a bacterial artificial chromosome library from, for example, *Arabidopsis thaliana* has been described (Choi et al., 1995). BAC libraries for numerous other plant species have been described and are publicly available including, for example, tomato (Hamilton et al., 1999), soybean (Meksem et al., 1999), wheat (Moullet et al., 1999), sorghum (Woo et al., 1994) and apple (Vinatzer et al., 1998). The construction and characterization of the IGF *Arabidopsis* BAC library and a complete BAC-based physical map of the *Arabidopsis thaliana* genome has been described by Mozo et al., (1998).

C. Detection of Centromere Sequences from Arrays

The ultimate goal of producing an array in accordance with current invention, will be in screening large numbers of clones for centromere sequences. Therefore, once an array is obtained, the first step will, in a preferred embodiment, involve hybridizing the array with a solution containing marked (labeled) nucleic acid sequences to identify candidate centromere sequences. Preferably, the array will comprise clones of genomic DNA representing an entire target genome.

Following hybridization, the surface is then washed free of unbound probe, and the signal corresponding to the probe label is identified for those regions on the surface where the probe has high affinity. Suitable labels for the probe include, but are not limited to, radiolabels, chromophores, fluorophores, chemiluminescent moieties, antigens and transition metals. In the case of a fluorescent label, detection can be accomplished with a charge-coupled device (CCD), fluorescence microscopy, or laser scanning (U.S. Pat. No. 5,445,934, specifically incorporated herein by reference in its entirety). When autoradiography is the detection method used, the marker is a radioactive label, such as $^{32}$P, and the radioactivity is detected, for example, the surface could be exposed to X-ray film, which is developed and read out on a scanner or, alternatively, simply scored manually. With radiolabeled probes, exposure time will typically range from one hour to several days. Fluorescence detection using a fluorophore label, such as fluorescein, attached to the ligand will usually require shorter exposure times. Alternatively, the presence of a bound probe may be detected using a variety of other techniques, such as an assay with a labeled enzyme, antibody, or the like. Other techniques using various marker systems for detecting bound ligand will also be readily apparent to those skilled in the art.

Detection may, alternatively, be carried out using PCR. For example, the methylated DNA fragments could be used as primers for PCR reactions and PCR detection could be carried out in situ on the slide. In this case one may wish to utilize one or more labeled nucleotides in the PCR mix to produce a detectable signal. Detection may also be carried out in a standard PCR reaction on the prepared samples to be screened. For this type of detection, the sectors in the array will not consist of DNA bound to solid support but will consist of DNA samples in solution in the wells of a microtiter dish.

III. Screening of Candidate Centromere Sequences

The invention provides an efficient method for isolation of centromere sequences. In studies employing the techniques of the invention in *Arabidopsis thaliana* frequently 30–50% of hybridizing clones contained centromere nucleic acid sequences. By employing the subtractive and comparative methods described herein, a nearly pure set of centromere clones can be obtained. Although such a highly enriched collection of centromere sequences could readily be assayed for centromere activity, it may be desirable to employ one or more techniques to further enrich the population of candidates for centromere sequences. Examples of the techniques are set forth below.

A. Utilization of Conserved Sequences

It has been shown that numerous centromere sequences are highly conserved (Copenhaver et al., 1999). Therefore, candidate centromere sequences could be screened for known syntenic genes, repeats or other sequences characteristic for centromeres. This could be done based on sequencing or could employ hybridization techniques. Where hybridization is used to obtain centromere sequences, it may be desirable to use less stringent hybridization conditions to allow formation of a heteroduplex. In these circumstances, one may desire to employ conditions such as about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature or decreased salt. Thus, hybridization conditions can be readily manipulated, and thus will generally be a method of choice depending on the desired results.

B. Identification of Centromere-Associated Characteristics

Another method for enriching for centromere sequences takes advantage of the unique DNA properties associated with centromeres and adjacent pericentromere regions. The centromeres of *Arabidopsis*, for example, are composed of long series of repeats of 180 bp repeats flanked by regions that are 10–70% retroelements, up to 15% pseudogenes and up to 29% transposons (Copenhaver et al., 1999). This is unique to the centromere, as retroelements, transposons and pseudogenes are very rare outside the centromere and pericentromere region. Furthermore, gene density decreases from an average of a gene every 4.5 kb on the chromosomal arm down to one in 150 kb at the centromere. This unique centromere composition could be exploited in a number of ways to enrich for centromere sequences, for example: (1) markers specific for retroelements, transposons, repeat DNA elements and pseudogenes can be devised to identify sequences that are dense with similar elements, and (2) utilizing sequence databases, clones comprising the predicted numbers of repetitive DNA, pseudogenes, retroelements and transposons, similar to the identified composition of other organisms can be used to identify centromere sequences.

C. Utliztion of Centromere-Associated Proteins

Another technique for enriching for centromere sequences involves chromatin immunoprecipitation (Dedon, 1991) of known centromere associate proteins, such as CENP-A, CENP-C and CENP-B. Still another technique for enriching for centromere sequences involves chromatin immunoprecipitation of centromere associated proteins such as deacetylated histones (Kuo and Allis, 1998). Yet another technique for enriching for centromere sequences involves isolating DNA fragments resistant to endonuclease digestion. Because centromeres are regarded as one of the most endonuclease-resistant portions of the genome, undigested DNA fragments remaining after nuclei are treated by any endonuclease, including DnaseI, Micrococcal Nuclease, S1 Nuclease or restriction endonucleases, often correspond to centromeres.

The sequences obtained by these techniques can be compared to those obtained in accordance with other embodiments of the invention, thereby confirming a particular sequence as being of centromere origin. Antibodies specific to centromere proteins can be incubated with proteins extracted from cells. Extracts can be native or previously treated to cross-link DNA to proteins. The antibodies and bound proteins can be purified away from the protein extracts and the DNA isolated. The DNA can then be used as a probe for fluorescent in situ hybridization (FISH) or to probe libraries to find neighboring centromere sequences.

1. Centromere-Associated Protein Specific Antibodies

Antibodies directed to centromere-associated proteins may be either monoclonal or polyclonal. The centromere-associated protein targets of the antibodies will include proteins that bind to the centromere region. Further, it is specifically contemplated that these centromere-associated protein specific antibodies would allow for the further isolation and characterization of the centromere-associated proteins. Recombinant production of such proteins provides a source of antigen for production of antibodies.

Alternatively, the centromere may be used as a ligand to isolate, using affinity methods, centromere-associated proteins. Once isolated, these protein can be used as antigens for the production polyclonal and monoclonal antibodies. A variation on this technique has been demonstrated by Rattner (1991), by cloning of centromere-associated proteins through the use of antibodies that bind in the vicinity of the centromere.

Means for preparing and characterizing antibodies are well known in the art (see, e.g., Antibodies: A Laboratory Manual, Cold Spring Harbor Laboratory, 1988, incorporated herein by reference). The methods for generating monoclonal antibodies (mAbs) generally begin along the same lines as those for preparing polyclonal antibodies. Briefly, a polyclonal antibody is prepared by immunizing an animal with an immunogenic composition in accordance with the present invention and collecting antisera from that immunized animal. A wide range of animal species can be used for the production of antisera. Typically the animal used for production of antisera is a rabbit, a mouse, a rat, a hamster, a guinea pig or a goat. A rabbit is a preferred choice for production of polyclonal antibodies because of the ease of handling, maintenance and relatively large blood volume.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin also can be used as carriers. Means for conjugating a polypeptide to a carrier protein are well known in the art and include glutaraldehyde, m-maleimido-bencoyl-N-hydroxysuccinimide ester, carbodimide and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection also may be given. The process of boosting and titering is repeated until a suitable titer is achieved. When a desired level of immunogenicity is obtained, the immunized animal can be bled and the serum isolated and stored, and/or the animal can be used to generate mAbs.

Monoclonal antibodies may readily be prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified chromosome-associated protein, polypeptide or peptide. The immunizing composition is administered in a manner effective to stimulate antibody producing cells. Rodents such as mice and rats are preferred animals, however, the use of rabbit, sheep, or frog cells also is possible. The use of rats may provide certain advantages (Goding 1986), but mice are preferred, with the BALB/c mouse being most preferred as this is most routinely used and generally gives a higher percentage of stable fusions.

Following immunization, somatic cells with the potential for producing antibodies, specifically B lymphocytes (B cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then with cells of an immortal myeloma cell, generally one of the same species as the that was immunized. Myeloma cell lines suited for use in hybridoma-producing procedures preferably are non-antibody-producing, have high fusion efficiency, enzyme deficiencies that render them incapable of growing in certain selective media that support the growth of only the desired fused cells (hybridomas).

Any one of a number of myeloma cells may be used, as are known to those of skill in the art (Goding 1986; Campbell 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler et al., 1975; 1976), and those using polyethylene glycol (PEG), such as 37% (v/v) PEG, (Gefter et al., 1977). The use of electrically induced fusion methods also is appropriate (Goding 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but 5 they have a limited life span in culture and generally die within about two weeks, Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines also could be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

2. ELISAs and Immunoprecipitation

ELISAs may be used in conjunction with the invention, for example, in identifying binding of a centromere-associated protein to a candidate centromere sequence. Such an assay could thereby facilitate the isolation of centromeres from a variety of species. In an ELISA assay, proteins or peptides comprising centromere-associated protein antigen sequences are immobilized onto a selected surface, preferably a -surface exhibiting a protein affinity such as the wells of a polystyrene microtiter plate. After washing to remove incompletely adsorbed material, it is desirable to bind or coat the assay plate wells with a nonspecific protein that is known to be antigenically neutral with regard to the test antisera such as bovine serum albumin (BSA), casein or solutions of milk powder. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or clinical or biological extract to be tested in a manner conducive to immune complex (antigen/antibody) formation. Such conditions preferably include diluting the antisera with diluents such as BSA, bovine gamma globulin (BGG) and phosphate buffered saline (PBS)/Tween®. These added agents also tend to assist in the reduction of nonspecific background. The layered antisera is then allowed to incubate for from about 2 to about 4 hours, at temperatures preferably on the order of about 25° to about 27° C. Following incubation, the antisera-contacted surface is washed so as to remove non-immunocomplexed material. A preferred washing procedure includes washing with a solution such as PBS/Tween®, or borate buffer.

Following formation of specific immunocomplexes between the test sample and the bound antigen, and subsequent washing, the occurrence and even amount of immunocomplex formation may be determined by subjecting same to a second antibody having specificity for the first. To provide a detecting means, the second antibody will preferably have an associated enzyme that will generate color or light development upon incubating with an appropriate chromogenic substrate. Thus, for example, one will desire to contact and incubate the antisera-bound surface with a urease or peroxidase-conjugated anti-human IgG for a period of time and under conditions that favor the development immunocomplex formation (e.g., incubation for 2 hours at room temperature in PBS-containing solution).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectra spectrophotometer.

3. Western Blots

Centromere-associated protein antibodies may find use in immunoblot or western blot analysis, for example, for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. This is especially useful when the antigens studied are immunoglobulins (precluding the use of immunoglobulins binding bacterial cell wall components), the antigens studied cross-react with the detecting agent, or they migrate at the same relative molecular weight as a cross-reacting signal.

Immunologically-based detection methods for use in conjunction with Western blotting include enzymatically-, radiolabel-, or fluorescently-tagged secondary antibodies against the protein moiety are considered to be of particular use in this regard.

IV. Transformed Host Cells and Transgenic Organisms

Methods and compositions for transforming a bacterium, a yeast cell, a plant cell, a mammal cell or an entire plant with one or more nucleic acid sequence, including a nucleic acid sequence comprising a centromere, form part of the current invention. A transgenic bacterium, yeast cell, mammalian cell, plant cell or plant derived from such a transformation process or the progeny and seeds from such a transgenic plant also are further embodiments of the invention.

Means for transforming bacteria and yeast cells are well known in the art. Typically, means of transformation are similar to those well known means used to transform other bacteria or yeast such as *E. coli* or *Saccharomyces cerevisiae*. Methods for DNA transformation of cells include *Agrobacterium*-mediated plant transformation, protoplast transformation (as used herein "protoplast transformation" includes PEG-mediated transformation, liposome-mediated transformation, electroporation and protoplast fusion transformation), gene transfer into pollen, injection into reproductive organs, injection into immature embryos and particle bombardment. Each of these methods has distinct advantages and disadvantages. Thus, one particular method of introducing genes into a particular plant strain may not necessarily be the most effective for another plant strain, but it is well known in the art which methods are useful for a particular plant strain.

There are many methods for introducing transforming DNA segments into cells, but not all are suitable for delivering DNA to cells. Suitable methods are believed to include virtually any method by which DNA can be introduced into a cell, such as by *Agrobacterium* infection, direct delivery of DNA such as, for example, by PEG-mediated transformation of protoplasts (Omirulleh et al., 1993), by desiccation/inhibition-mediated DNA uptake, by electroporation, by agitation with silicon carbide fibers, by acceleration of DNA coated particles, etc. In certain embodiments, acceleration methods are preferred and include, for example, microprojectile bombardment and the like.

Technology for introduction of DNA into cells is well-known to those of skill in the art. Four general methods for delivering a gene into cells have been described: (1) chemical methods (Graham et al., 1973; Zatloukal et al., 1992); (2) physical methods such as microinjection (Capecchi, 1980), electroporation (Wong et al., 1982; Fromm et al., 1985; U.S. Pat. No. 5,384,253) and the gene gun (Johnston et al., 1994; Fynan et al., 1993); (3) viral vectors (Clapp 1993; Lu et al., 1993; Eglitis et al., 1988a; 1988b); and (4) receptor-mediated mechanisms (Curiel et al., 1991; 1992; Wagner et al., 1992).

A. Electroporation

The application of brief, high-voltage electric pulses to a variety of animal and plant cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of cloned genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

The introduction of DNA by means of electroporation, is well-known to those of skill in the art. In this method, certain cell wall-degrading enzymes, such as pectin-degrading enzymes, are employed to render the target recipient cells more susceptible to transformation by electroporation than untreated cells. Alternatively, recipient cells are made more susceptible to transformation, by mechanical wounding. To effect transformation by electroporation one may employ either friable tissues such as a suspension culture of cells, or embryogenic callus, or alternatively, one may transform immature embryos or other organized tissues directly. One would partially degrade the cell walls of the chosen cells by exposing them to pectin-degrading enzymes (pectolyases) or mechanically wounding in a controlled manner. Such cells would then be recipient to DNA transfer by electroporation, which may be carried out at this stage, and transformed cells then identified by a suitable selection or screening protocol dependent on the nature of the newly incorporated DNA.

B. Microprojectile Bombardment

A further advantageous method for delivering transforming DNA segments to cells is microprojectile bombardment. In this method, particles may be coated with nucleic acids and delivered into cells by a propelling force. Exemplary particles include those comprised of tungsten, gold, platinum, and the like.

An advantage of microprojectile bombardment, in addition to it being an effective means of reproducibly stably transforming monocots, is that neither the isolation of protoplasts (Cristou et al., 1988) nor the susceptibility to *Agrobacterium* infection is required. An illustrative embodiment of a method for delivering DNA into maize cells by acceleration is a Biolistics Particle Delivery System, which can be used to propel particles coated with DNA or cells through a screen, such as a stainless steel or Nytex screen, onto a filter surface covered with cells cultured in suspension. The screen disperses the particles so that they are not delivered to the recipient cells in large aggregates.

For the bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. If desired, one or more screens also are positioned between the acceleration device and the cells to be bombarded. Through the use of techniques set forth herein one may obtain up to 1,000 or more foci of cells transiently expressing a marker gene. The number of cells in a focus that express the exogenous gene product 48 hours post-bombardment often range from 1 to 10 and average 1 to 3.

In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. It is believed that pre-bombardment manipulations are especially important for successful transformation of immature embryos.

Accordingly, it is contemplated that one may wish to adjust various of the bombardment parameters in small scale studies to fully optimize the conditions. One may particularly wish to adjust physical parameters such as gap distance, flight distance, tissue distance, and helium pressure. The execution of other routine adjustments will be known to those of skill in the art in light of the present disclosure.

C. *Agrobacterium*-Mediated Transfer

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art (see, for example, the methods described Fraley et al., 1985; Rogers et al., 1987). Advances in *Agrobacterium*-mediated transfer now allow introduction of large segments of DNA (Hamilton, 1997; Hamilton et al., 1996).

Using conventional transformation vectors, chromosomal integration is required for stable inheritance of the foreign DNA. However, vectors comprising centromeres obtained in accordance with the invention may be used for transformation with or without integration, as the centromere function required for inheritance is encoded within the vector. In particular embodiments, transformation events in which the vector is not chromosomally integrated may be preferred, in that problems with site-specific variations in expression and insertional mutagenesis may be avoided.

The region of DNA to be transferred is defined by the border sequences, and intervening DNA is usually inserted into the plant genome as described (Spielmann et al., 1986; Jorgensen et al., 1987). Modern *Agrobacterium* transformation vectors are capable of replication in *E. coli* as well as *Agrobacterium*, allowing for convenient manipulations as described (Klee et al., 1985). Moreover, recent technological advances in vectors for *Agrobacterium*-mediated gene transfer have improved the arrangement of genes and restriction sites in the vectors to facilitate construction of vectors capable of expressing various polypeptide coding genes. The vectors described (Rogers et al., 1987), have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

*Agrobacterium*-mediated transformation of leaf disks and other tissues such as cotyledons and hypocotyls or whole plants appears to be limited to plants that *Agrobacterium* naturally infects. *Agrobacterium*-mediated transformation is most efficient in dicotyledonous plants. Few monocots appear to be natural hosts for *Agrobacterium*, although transgenic plants have been produced in asparagus and more significantly in maize using *Agrobacterium* vectors as described (Bytebier et al., 1987; U.S. Pat. No. 5,591,616, specifically incorporated herein by reference). Therefore, commercially important cereal grains such as rice, corn, and wheat must usually be transformed using alternative methods. However, as mentioned above, the transformation of asparagus using *Agrobacterium* also can be achieved (see, for example, Bytebier et al., 1987). *Agrobacterium*-mediated transfer may be made more efficient through the use of a mutant that is defective in integration of the *Agrobacterium* T-DNA but competent for delivery of the DNA into the cell (Mysore et al., 2000a). Additionally, even in *Arabidopsis* ecotypes and mutants that are recalcitrant to *Agrobacterium* root transformation, germ-line transformation may be carried out (Mysore et al., 2000b).

A transgenic plant formed using *Agrobacterium* transformation methods often contains a single insertion on one chromosome. Such transgenic plants can be referred to as being hemizygous for the added DNA. A more accurate name for such a plant is an independent segregant, because each transformed plant represents a unique T-DNA integration event. More preferred is a transgenic plant that is homozygous for the added foreign DNA; i.e., a transgenic plant that contains two copies of a the insertion, one at the same locus on each chromosome of a chromosome pair. A homozygous transgenic plant can be obtained by sexually mating (selfing) an independent segregant transgenic plant that contains a single added insertion, germinating some of the seed produced and analyzing the resulting plants produced for enhanced activity of a marker gene relative to a control (native, non-transgenic) or an independent segregant transgenic plant.

It is to be understood that two different transgenic plants also can be mated to produce offspring that contain two independently segregating added, exogenous minichromosome vectors. Selfing of appropriate progeny can produce plants that are homozygous for both added, exogenous nucleic acids that encode a polypeptide of interest. Backcrossing to a parental plant and out-crossing with a non-transgenic also are contemplated.

D. Other Transformation Methods

Transformation of protoplasts can be achieved using methods based on calcium phosphate precipitation, polyethylene glycol treatment, electroporation, and combinations of these treatments (see, e.g., Potrykus et al., 1985; Lorz et al., 1985; Fromm et al., 1986; Uchimiya et al., 1986 Callis et al., 1987; Marcotte et al., 1988).

Application of these systems to different strains for the purpose of making transgenic organisms depends upon the ability to regenerate that particular strain from protoplasts. Illustrative methods for the regeneration of cereals from protoplasts are described (Fujimura et al., 1985; Toriyama et al., 1986; Yamada et al., 1986; Abdullah et al., 1986).

To transform strains that cannot be successfully regenerated from protoplasts, other ways to introduce DNA into intact cells or tissues can be utilized. For example, regeneration of cereals from immature embryos or explants can be effected as described (Vasil 1988). In addition, "particle gun" or high-velocity microprojectile technology can be utilized (Vasil 1992).

Using the latter technology, DNA is carried through the cell wall and into the cytoplasm on the surface of small metal particles as described (Klein et al., 1987; Klein et al., 1988; McCabe et al., 1988). The metal particles penetrate through several layers of cells and thus allow the transformation of cells within tissue explants.

Protoplast fusion, for example, could be used to integrate a recombinant construct comprising a centromere into a host cell, such as a yeast cell, and then fuse those cells to protoplasts. The chromosomes lacking centromeres (such as yeast chromosomes in this example) would be eliminated by the cell while the minichromosome would be stably maintained. Numerous examples of protocols for protoplast fusion that could be used with the invention have been described (see, e.g., Negrutiu et al., 1992, and Peterson).

Liposome fusion could be used to introduce a recombinant construct comprising a centromere, such as a minichromosome, by, for example, packaging the recombinant construct into small droplets of lipids (liposomes) and then fusing these liposomes to protoplasts thus delivering the AC into the cell (see Lurqui and Rollo, 1993).

V. Restriction Endonucleases

In certain embodiments of the invention, restriction endonucleases, including both methylation-sensitive and non-methylation sensitive restriction endonucleases, may be used. By "methylation sensitive" it is meant a restriction endonuclease that exhibits reduced efficiency of cleaving a target cut site when that cut site is methylated relative to the same site which is unmethylated. The reduction in efficiency of restriction among methylated cut sites may be about 10%, 25%, 50%, or more preferably, from about 75% to about 100% relative to the efficiency of restriction at unmethylated cut sites under identical conditions. Particularly useful will be methylation-sensitive restriction endonucleases that have non methylation sensitive isoschizomers, thereby allowing comparisons of genomic DNA digests and subsequent identification of uncut DNA due to methylation. One particularly useful pair of isoschizomers that may be employed with the invention are MspI and HpaII.

Numerous restriction endonucleases are known to those of skill in the art and may be employed with the current invention. Examples of such restriction endonucleases that could potentially be used include, but are not necessarily limited to, AatI, AatII, AccI, AccII, AccIII, Acc65I, AclI, AclII, AdeI, AflIII, AgeI, AhaII, AhdI, AluI, AlwI, Alw21I, Alw26I, Alw44I, AlwNI, AmaI, AorI, ApaI, ApaLI, ApyI, AquI, AscI, Asp718I, AspMI, AspMDI, AtuCI, AvaI, AvaII, BaeI, BalI, BamFI, BamHI, BamKI, BanI, BanII, BazI, BbeI, BbIII, BbrPI, BbuI, BbvI, Bca77I, BcgI, BcIVI, BclI, BcnI, BepI, Bfl57I, Bfl89I, BfrI, BglI, BglII, BlnI, Bme216I, BmeTI, BnaI, BpII, BpII, BpuI, Bpu10I, Bpu1102I, BsaI, BsaAI, BsaBI, BsaHI, BsaJI, BsaWI, BscFI, BseCI, BseDI, BseGI, BseLI, BseMI, BsgI, Bsh1365I, BshNI, BsIBI, BsIEI, BsILI, BsIMI, BsIWI, BsIXI, BslI, BsmI, BsmAI, BsoBI, BsoFI, Bsp106I, Bsp119I, Bsp120I, Bsp143I, Bsp143II, Bsp1286I, BspDI, BspEI, BspFI, BspHI, BspKT6I, BspLI, BspLU11III, BspMI, BspMII, BspRI, M.BspRI, BspST5I, BspXI, BspXII, BspZEI, BsrBI, BsrFI, BssSI, Bst1107I, BstBI, BstEII, BstEIII, BstGI, BstNI, BstOI, BstUI, BstVI, BstXI, BstYI, Bsu15I, BsuBI, BsuEII, BsuFI, BsuMI, BsuRI, CacI, CbII, CfoI, CfrI, Cfr6I, Cfr9I, CfrII, Cfrl3I, CfrBI, ClaI, CpeI, Csp6I, Csp45I Csp68KII, CtyI, CvlAI, CvlAII, CvlBI, M.CvlBIII, CvlJI, N.CvPII, CjlQI, N.CvlQXI, CvlRI, CvlRII, DdeI, DpI, DpinII, DraI, DraII, DraIII, DrdI, DsaV, EaeI, EagI, Eam1104I, EantI1051, EarI, EcaI, Ec1186II, Eco24I, Eco3II, Eco32I, Eco47I, Eco47III, EcoM, Eco88I, Eco91I, Eco105I, Eco147I, Eco1831I, EcoAI, EcoBI, EcoDI, EcoHI, EcoHK311, EcoKI, EcoO109I, EcoPI, EcoP15I, EcoRI, -M.EcoRI, EcoRII, EcoRV, EcoR124I, EcoR]241I, EheI, Esp3I, FauI, FnuDII, FnuEI, Fnu4HI, FokI, MFokI, FseI, FspI, Fsp4HI, GsuI, HaeII, HaeIII, HapII, HgaI, HgIAI, HgICI, HgICII, HgIDI, HgIEI, HgIHI, HhaI, MalI, HlnII, Hln6I, HWII, HlincII, HindII, HindIII, Hinfl, HpaI, HpaII, HphI, Hpy1881, HsoI, ItaI, KasI, KpnI, Kpn21, KspAI, L1AI, MaeII, MbII, MboI, MboII, MJ71, MluI, M9273I, M9273II, MlyI, MmeI, MmeII, MnII, MseI, MspI, MthTI, MthZI, MunI, MvaI, Mva1269I, NaeI, NanII, NarI, NcII, NcIAI, NcoI, NdeI, NgoBV, NgoBVIII, NgoCI, NgoCII, NgoFvII, NgoMIV, NgoPII, NgoSII, NgoWI, NheI, NlaIII, NlaX, NmuDI, NmuEI, NotI, NruI, NsbI, NsII, NspI, NspV, PacI, PaeI, PaeR71, PagI, PfaI, PflMI, PgII, PmeI, PmlI, PshAI, Psp5II, Psp1406I, PspGI, PstI, PvuI, PvuII, Ral8I, RalF40I, RflFI, RflFII, Rrh4273I, RsaI, RshI, RsrI, RsrII, SacI, SaDI, SalI, SaffiI, SapI, Sau961, Sau3239I, Sau3AI, SauLPI, Sbol3l, ScaI, ScrFI, SduI, SexAI, SfaNI, SjlI, SInI, SmaI, SnaBI, SnoI, SoII, SpeI, SphI, Sru30DI, Sse9I, Sse83871, SsoI, SsoII, SspRFI, StII, StsI, StuI, StyD41, StyLTI, StyLTIII, StYSJI, StYSPI, StySQI, TaII, TaqX, TaqXI, TpiI, TflI, ThaI, Tsp451, Tth111I, TthHB81, Van9II, VspI, XbaI, XcmI, XcyI, XhoI, XhoII, XmaI, XmnI, XorII, and ZanI.

VI. Plants

The term "plant," as used herein, refers to any type of plant. The inventors have provided below an exemplary description of some plants that may be used with the invention. However, the list is not limiting, as other types of plants will be known to those of skill in the art and could be used with the invention.

A common class of plants exploited in agriculture are vegetable crops, including artichokes, kohlrabi, arugula, leeks, asparagus, lettuce (e.g., head, leaf, romaine), bok choy, malanga, broccoli, melons (e.g., muskmelon, watermelon, crenshaw, honeydew, cantaloupe), brussels sprouts, cabbage, cardoni, carrots, napa, cauliflower, okra, onions, celery, parsley, chick peas, parsnips, chicory, Chinese cabbage, peppers, collards, potatoes, cucumber plants (marrows, cucumbers), pumpkins, cucurbits, radishes, dry bulb onions, rutabaga, eggplant, salsify, escarole, shallots, endive, garlic, spinach, green onions, squash, greens, beet (sugar beet and fodder beet), sweet potatoes, swiss-chard, horseradish, tomatoes, kale, turnips, and spices.

Other types of plants frequently finding commercial use include fruit and vine crops such as apples, apricots, cherries, nectarines, peaches, pears, plums, prunes, quince almonds, chestnuts, filberts, pecans, pistachios, walnuts, citrus, blueberries, boysenberries, cranberries, currants, loganberries, raspberries, strawberries, blackberries, grapes, avocados, bananas, kiwi, persimmons, pomegranate, pineapple, tropical fruits, pornes, melon, mango, papaya, and lychee.

Many of the most widely grown plants are field crop plants such as evening primrose, meadow foam, corn (field, sweet, popcorn), hops, jojoba, peanuts, rice, safflower, small grains (barley, oats, rye, wheat, etc.), sorghum, tobacco, kapok, leguminous plants (beans, lentils, peas, soybeans), oil plants (rape, mustard, poppy, olives, sunflowers, coconut, castor oil plants, cocoa beans, groundnuts), fiber plants (cotton, flax, hemp, jute), lauraceae (cinnamon, camphor), or plants such as coffee, sugarcane, tea, and natural rubber plants.

Still other examples of plants include bedding plants such as flowers, cactus, succulents and ornamental plants, as well as trees such as forest (broad-leaved trees and evergreens, such as conifers), fruit, ornamental, and nut-bearing trees, as well as shrubs and other nursery stock.

VII. Centromere Compositions

Certain aspects of the present invention concern methods for isolating centromere containing nucleic acid segments and recombinant vectors comprising such sequences. As used herein, the term "nucleic acid segment" refers to a nucleic acid molecule that has been purified from total genomic nucleic acids of a particular species or has been made synthetically. Therefore, a nucleic acid segment conferring centromere function refers to a nucleic acid segment that contains centromere sequences yet is isolated away from, or purified free from, total genomic nucleic acids. Included within the term "nucleic acid segment," are nucleic acid segments and smaller fragments of such segments, and also recombinant vectors, including, for example, BACs, YACs, plasmids, cosmids, phage, viruses, and the like.

Similarly, a nucleic acid segment comprising an isolated or purified centromeric sequence refers to a nucleic acid segment including centromere sequences and, in certain aspects, regulatory sequences, isolated substantially away from other naturally occurring sequences, or other nucleic acid sequences. In this respect, the term "gene" is used for simplicity to refer to a functional nucleic acid segment, protein, polypeptide or peptide encoding unit. As will be understood by those in the art, this functional term includes both genomic sequences, cDNA sequences and smaller engineered gene segments that may express, or may be adapted to express, proteins, polypeptides or peptides.

"Isolated substantially away from other sequences" means that the sequences of interest, in this case centromere sequences, are included within a sample of genomic nucleic acids. Of course, this refers to the nucleic acid segment as originally isolated, and does not exclude genes or coding regions later added to the segment by the hand of man.

In particular embodiments, the invention concerns isolated nucleic acid segments and recombinant vectors including nucleic acid sequences that encode a centromere functional sequence. Nucleic acid segments that exhibit centromere function activity will be most preferred. The nucleic acid segments provided by the present invention, regardless of the length of the sequence itself, may be combined with other nucleic acid sequences, such as promoters, polyadenylation signals, additional restriction endonuclease recognition sites, multiple cloning sites, other coding segments, and the like, such that their overall length may vary considerably. It is therefore contemplated that a nucleic acid fragment of almost any length may be employed, with the total length preferably being limited by the ease preparation and use in the intended recombinant DNA protocol.

A. Primers and Probes

In addition to their use in the construction of recombinant constructs, including artificial chromosomes, the nucleic acid sequences provided hereby may find a variety of other uses. For example, the centromere sequences obtained with the invention, may find use as probes or primers in nucleic acid hybridization embodiments. As such, it is contemplated that nucleic acid segments that comprise a sequence region that consists of at least a 10 nucleotide long contiguous sequence that has the same sequence as, or is complementary to, a 10 nucleotide long contiguous DNA segment of a methylated nucleic acid sequence of a centromere.

As described in detail herein, the ability of such nucleic acid probes to specifically hybridize to centromeric sequences will enable them to be of use in detecting the presence of similar, partially complementary sequences from other plants or animals. However, other uses are envisioned, including the use of the centromeres for the preparation of mutant species primers, or primers for use in preparing other genetic constructions.

Nucleic acid fragments having sequence regions consisting of contiguous nucleotide stretches of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100 or even of 101–200 nucleotides or so, identical or complementary to a centromere sequence provided by the current invention, are particularly contemplated as hybridization probes for use in, e.g., Southern and Northern blotting and FISH hybridization to chromosomes. Smaller fragments will generally find use in hybridization embodiments, wherein the length of the contiguous complementary region may be varied, such as between about 10–14 and about 100 or 200 nucleotides, but larger contiguous complementarity stretches also may be used, according to the length complementary sequences one wishes to detect.

Of course, fragments may also be obtained by other techniques such as, by mechanical shearing or by restriction endonuclease digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. Nos. 4,683,195 and 4,683,202 (each incorporated herein by reference), by introducing selected sequences into recombinant vectors for recombinant production, and by other recombinant DNA techniques generally known to those of skill in the art of molecular biology.

Accordingly, the centromere sequences provided by the current invention may be used for their ability to selectively form duplex molecules with complementary stretches of DNA fragments. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, for example, as described herein above.

B. Large Nucleic Acid Segments

Using multiple methylated centromere sequences, it may be possible to purify a contiguous DNA fragment that contains the centromere sequences as well as additional centromere sequences located between the methylated sequences. In order to carry this out, very large DNA fragments up to the size of an entire chromosome are prepared by embedding tissues in agarose using, for example, the method described by Copenhaver et al., (1995). These large pieces of DNA can be digested in the agarose with any restriction endonuclease. Those restriction endonucleases that will be particularly useful for isolating intact centromeres include enzymes that yield very large DNA fragments. Such restriction endonucleases include those with specificities greater than six base pairs, for example, Asc I, Bae I, BbvC I, Fse I, Not I, Pac I, Pme I, PpuM I, Rsr II, SanD I, Sap I, SexA I, Sfi I, Sgf I, SgrA I, Sbf I, Srf I, Sse8387 I, Sse8647 I, Swa, UbaD I, and UbaE I, or any other enzyme that cuts at a low frequency within the target-plant genome, and specifically within the centromeric region. Alternatively, a partial digest with a more frequent cutting restriction endonuclease could be used.

Alternatively, large DNA fragments spanning some or all of a centromere could be produced using RecA-Assisted Restriction Endonuclease (RARE) cleavage (Ferrin, 1991). In order to carry this out, very large DNA fragments up to the size of an entire chromosome are prepared by embedding tissues in agarose using, for example, the method described by Copenhaver et al., (1995). Single stranded DNA oligomers with sequences homologous to sites flanking the region of DNA to be purified are made to form triple stranded complexes with the agarose embedded DNA using the recombinase enzyme RecA. The DNA is then treated with a site specific methylase such as, for example, Alu I methylase, BamH I methylase, dam methylase, EcoR I methylase, Hae III methylase, Hha I methylase, HpaII methylase, or Msp methylase. The methylase will modify all the sites specified by its recognition sequence except those within the triplex region protected by the RecA/DNA oligomer complex. The RecA/DNA oligomer complex are then removed from the agarose embedded DNA and the DNA is then cleaved with the restriction endonuclease corresponding to the methylase used, for example, if EcoRI methylase was used then EcoRl restriction endonuclease would be used to perform the cleavage. Only those sites protected from modification will be subject to cleavage by the restriction endonuclease. Thus by using sequences flanking the centromeric regions that contain the recognition sequence of a site specific methylase/restriction endonuclease pair RARE can be used to cleave the entire region from the rest of the chromosome. It is important to note that this method can be used to isolate a DNA fragment of unknown composition by using centromere sequences flanking it. Thus, this method may be used to isolate the DNA contained within any gaps in the physical map for the centromeres. The DNA isolated by this method can then be sequenced.

Large DNA fragments produced by digestion with restriction endonucleases or by RARE cleavage are then separated by size using pulsed-field gel electrophoresis (PFGE) (Schwartz et al., 1982). Specifically, Contour-clamped Homogenous Electric Field (CHEF) electrophoresis (a variety of PFGE) can be used to separate DNA molecules as large as 10 Mb (Chu et al., 1985). Large DNA fragments resolved on CHEF gels can then be analyzed using standard Southern hybridization techniques to identify and measure the size of those fragments that contain both centromere flanking sequences and therefor, the centromere. After determining the size of the centromere containing fragment by comparison with known size standards, the region from the gel that contains the centromere fragment can be cut out of a duplicate gel. This centromeric DNA can then be analyzed, sequenced, and used in a variety of applications, as described herein, including the construction of artificial chromosomes.

C. Recombinant Constructs Comprising Centromere Sequences

In light of the instant disclosure it will be possible for those of ordinary skill in the art to construct recombinant DNA constructs comprising centromeres isolated in accordance herewith. Useful construction methods are well-known to those of skill in the art (see, for example, Maniatis et al., 1982). As constructed, such constructs may preferably include an autonomous replication sequence (ARS) functional in the target organism, a centromere functional in the target organism, and optionally, a telomere functional in the target organism or exogenous genes.

The basic elements in addition to a centromere that may be used in constructing recombinant vectors will be known to those of skill in the art. For example, one type of telomere sequence that could be used is an *Arabidopsis* telomere, which consists of head to tail series of repeats of the monomer CCCTAAA totaling a few (for example, 3–4) kb in length. The telomeres of *Arabidopsis*, like those of other organisms, vary in length and do not appear to have a strict length requirement. An example of a cloned telomere can be found in GenBank accession number M20158 (Richards and Ausubel, 1988). Yeast telomere sequences have also been described (see, e.g., Louis, 1994; Genbank accession number S70807). Additionally, a method for isolating a higher eukaryotic telomere from *Arabidopsis thaliana* was described by Richards and Ausubel (1988).

It is commonly believed that higher eukaryotes do not posses a specific sequence that is used as a replication origin, but instead replicate their DNA from random sites distributed along the chromosome. In *Arabidopsis*, it is thought that the cell will form origins of replications about once every 70 kb (Van't Hof, 1978). Thus, because higher eukaryotes have origins of replication at potentially random positions on each chromosome, it is not possible to describe a specific origin sequence, but it may generally be assumed that a segment of DNA of a sufficient size will be recognized by the cell and origins will be generated on the construct. For example, any piece of *Arabidopsis* genomic DNA larger than 70 kb would be expected to contain an ARS. By including such a segment of DNA on a recombinant vector, ARS function may be provided to the vector. Additionally, many *S. cerevisiae* autonomous replicating sequences have been sequenced and could be used to fulfill the ARS function on a yeast shuttle vector. One example is the *Saccharomyces cerevisiae* autonomously replicating sequence ARS131A (GenBank number L25319). Many origins of replications have been also been sequenced and cloned from *E. coli* and could be used with the invention, for example, the Col E1 origin of replication (Ohmori and Tornizawa, 1979; GenBank number V00270). One *Agrobacterium* origin that could be used is RiA4. The localization of origins of replication in the plasmids of *Agrobacterium rhizogenes* strain A4 was described by Jouanin et al. (1985).

1. Considerations in the Preparation of Recombinant Constructs

In addition to the basic elements, positive or negative selectable markers (e.g., antibiotic or herbicide resistance genes), and a cloning site for insertion of foreign DNA may be included. In addition, a visible marker, such as green fluorescent protein, also may be desirable. In order to propagate the vectors in *E. coli*, it is necessary to convert the linear molecule into a circle by addition of a stuffer fragment between the telomeres. Inclusion of an *E. coli* plasmid replication origin and selectable marker also may be preferred. It also may be desirable to include *Agrobacterium* sequences to improve replication and transfer to cells. It may also be desirable to include sequences for site-specific recombination such as the lox sites recognized by the cre recombinase.

Artificial chromosomes that replicate in yeast also may be constructed to take advantage of the large insert capacity and stability of repetitive DNA inserts afforded by this system (see Burke et al., 1987). In this case, yeast ARS and CEN sequences may be added to the vector. The artificial chromosome is maintained in yeast as a circular molecule using a stuffer fragment to separate the telomeres.

A fragment of DNA, from any source whatsoever, may be purified and inserted into a recombinant construct at any appropriate restriction endonuclease cleavage site. The DNA segment usually will include various regulatory signals for the expression of proteins encoded by the fragment. Alternatively, regulatory signals resident in the recombinant construct may be utilized.

The techniques and procedures required to accomplish insertion are well-known in the art (see Maniatis et al., 1982). Typically, this is accomplished by incubating a circular plasmid or a linear DNA fragment in the presence of a restriction endonuclease such that the restriction endonuclease cleaves the DNA molecule. Endonucleases preferentially break the internal phosphodiester bonds of polynucleotide chains. They may be relatively unspecific, cutting polynucleotide bonds regardless of the surrounding nucleotide sequence. However, the endonucleases that cleave only a specific nucleotide sequence are called restriction endonucleases. Restriction endonucleases generally internally cleave DNA molecules at specific recognition sites, making breaks within "recognition" sequences that in many, but not all, cases exhibit two-fold symmetry around a given point. Such enzymes typically create double-stranded breaks.

Many of these enzymes make a staggered cleavage, yielding DNA fragments with protruding single-stranded 5' or 3' termini. Such ends are said to be "sticky" or "cohesive" because they will hydrogen bond to complementary 3' or 5' ends. As a result, the end of any DNA fragment produced by an enzyme, such as EcoRI, can anneal with any other fragment produced by that enzyme. This properly allows splicing of foreign genes into plasmids, for example. Some restriction endonucleases that may be particularly useful with the current invention include HindIII, PsiI, EcoRI, and BamHI.

Some endonucleases create fragments that have blunt ends, that is, that lack any protruding single strands. An alternative way to create blunt ends is to use a restriction endonuclease that leaves overhangs, but to fill in the overhangs with a polymerase, such as Klenow, thereby resulting in blunt ends. When DNA has been cleaved with restriction endonucleases that cut across both strands at the same position, blunt end ligation can be used to join the fragments directly together. The advantage of this technique is that any pair of ends may be joined together, irrespective of sequence.

Those nucleases that preferentially break off terminal nucleotides are referred to as exonucleases. For example, small deletions can be produced in any DNA molecule by treatment with an exonuclease that starts from each 3' end of the DNA and chews away single strands in a 3' to 5' direction, creating a population of DNA molecules with single-stranded fragments at each end, some containing terminal nucleotides. Similarly, exonucleases that digest DNA from the 5' end or enzymes that remove nucleotides from both strands have often been used. Some exonucleases that may be particularly useful in the present invention include Bal31, SI, and ExoIII. These nucleolytic reactions can be controlled by varying the time of incubation, the temperature, and the enzyme concentration needed to make deletions. Phosphatases and kinases also may be used to control which fragments have ends that can be joined. Examples of useful phosphatases include shrimp alkaline phosphatase and calf intestinal alkaline phosphatase. An example of a useful kinase is T4 polynucleotide kinase.

Once the source DNA sequences and vector sequences have been cleaved and modified to generate appropriate ends they are incubated together with enzymes capable of mediating the ligation of the two DNA molecules. Particularly useful enzymes for this purpose include T4 ligase, *E. coli* ligase, or other similar enzymes. The action of these enzymes results in the sealing of the linear DNA to produce a larger DNA molecule containing the desired fragment (see, for example, U.S. Pat. Nos. 4,237,224; 4,264,731; 4,273,875; 4,322,499 and 4,336,336, which are specifically incorporated herein by reference).

It is to be understood that the termini of the linearized plasmid and the termini of the DNA fragment being inserted must be complementary or blunt in order for the ligation reaction to be successful. Suitable complementarity can be achieved by choosing appropriate restriction endonucleases (i.e., if the fragment is produced by the same restriction endonuclease or one that generates the same overhang as that used to linearize the plasmid, then the termini of both molecules will be complementary). As discussed previously, in one embodiment of the invention, at least two classes of the vectors used in the present invention are adapted to receive the foreign oligonucleotide fragments in only one orientation. After joining the DNA segment to the vector, the resulting hybrid DNA can then be selected from among the large population of clones or libraries.

A method useful for the molecular cloning of DNA sequences includes in vitro joining of DNA segments, fragmented from a source of high molecular weight genomic DNA, to vector DNA molecules capable of independent replication. The cloning vector may include plasmid DNA (see Cohen et al., 1973), phage DNA (see Thomas et al., 1974), SV40 DNA (see Nussbaum et al., 1976), yeast DNA, *E. coli* DNA and most significantly, plant or animal DNA.

A variety of processes are known that may be utilized to effect transformation; i.e., the inserting of a heterologous DNA sequences into a host cell, whereby the host becomes capable of efficient expression of the inserted sequences.

2. Regulatory Elements

In one embodiment of the invention, recombinant constructs-may include a plant promoter, for example, the CaMV 35S promoter (Odell et al., 1985), or others such as CAMV 19S (Lawton et al., 1987), nos (Ebert et al., 1987), Adh (Walker et al., 1987), sucrose synthase (Yang & Russell, 1990), a-tubulin, actin (Wang et al., 1992), cab (Sullivan et al., 1989), PEPCase (Hudspeth & Grula, 1989) or those associated with the R gene complex (Chandler et al., 1989). Tissue specific promoters such as root cell promoters (Conkling et al., 1990) and tissue specific enhancers (Fromm et al., 1989) are also contemplated to be useful, as are inducible promoters such as ABA- and turgor-inducible promoters. In particular embodiments of the invention, a Lat52 promoter may be used (Twell et al., 1991). A particularly useful tissue specific promoter is the SCARECROW (Scr) root-specific promoter (DiLaurenzio et al., 1996).

As the DNA sequence between the transcription initiation site and the start coding sequence, i.e., the untranslated leader sequence, can influence gene expression. Therefore, one may also wish to employ a particular leader sequence.

It is envisioned that a functional gene could be introduced under the control of novel promoters or enhancers, etc., or perhaps even homologous or tissue specific (for example, root-, collar/sheath-, whorl-, stalk-, earshank-, kernel- or leaf-specific) promoters or control elements. In particular embodiments of the invention, the functional gene may be in an antisense orientation relative to the promoter.

3. Terminators

It may also be desirable to link a functional gene to a 3' end DNA sequence that acts as a signal to terminate transcription and allow for the poly-adenylation of the mRNA produced by coding sequences. Such a terminator may be the native terminator of the functional gene or, alternatively, may be a heterologous 3' end. Examples of terminators that could be used with the invention are those from the nopaline synthase gene of *Agrobacterium tumefaciens* (nos 3' end) (Bevan et al., 1983), the terminator for the T7 transcript from the octopine synthase gene of *Agrobacterium tumefaciens*, and the 3' end of the protease inhibitor I or II genes from potato or tomato.

4. Marker Genes

It may be desirable to use one or more marker genes in accordance with the invention. Such markers may be adapted for use in prokaryotic, lower eukaryotic or higher eukaryotic systems, or may be capable of use in any combination of the foregoing classes of organisms. By employing a selectable or screenable marker protein, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait that one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the invention.

Included within the terms selectable or screenable markers also are genes that encode a "secretable marker" whose secretion can be detected as a means of identifying or selecting for transformed cells. Examples include markers that are secretable antigens that can be identified by antibody interaction, or even secretable enzymes that can be detected by their catalytic activity. Secretable proteins fall into a number of classes, including small, diffusible proteins detectable, e.g., by ELISA; small active enzymes detectable in extracellular solution (e.g., α-amylase, β-lactamase, phosphinothricin acetyltransferase); and proteins that are inserted or trapped in the cell wall (e.g., proteins that include a leader sequence such as that found in the expression unit of extensin or tobacco PR-S).

With regard to selectable secretable markers, the use of a gene that encodes a protein that becomes sequestered in the cell wall, and which protein includes a unique epitope is considered to be particularly advantageous. Such a secreted antigen marker would ideally employ an epitope sequence that would provide low background in tissue, a promoter-leader sequence that would impart efficient expression and targeting across the plasma membrane, and would produce protein that is bound in the cell wall and yet accessible to antibodies. A normally secreted wall protein modified to include a unique epitope would satisfy all such requirements.

a.) Selectable Markers

Many selectable marker genes may be used in accordance with invention including, but not limited to, neo (Potrykus et al., 1985), which provides kanamycin resistance and can be selected for using kanamycin, G418, paromomycin, etc.; bar, which confers bialaphos or phosphinothricin resistance; a mutant EPSP synthase protein (Hinchee et al., 1988) conferring glyphosate resistance; a nitrilase such as bxn from *Klebsiella ozaenae* which confers resistance to bromoxynil (Stalker et al., 1988); a mutant acetolactate synthase (ALS) which confers resistance to imidazolinone, sulfonylurea or other ALS inhibiting chemicals (European Patent Application 154,204, 1985); a methotrexate resistant DBFR (Thillet et al., 1988), a dalapon dehalogenase that confers resistance to the herbicide dalapon; or a mutated anthranilate synthase that confers resistance to 5-methyl tryptophan. Where a mutant EPSP synthase is employed, additional benefit may be realized through the incorporation of a suitable chloroplast transit peptide, CTP (U.S. Pat. No. 5,188,642) or OTP (U.S. Pat. No. 5,633,448) and use of a modified maize EPSPS (PCT Application WO 97/04103).

An illustrative embodiment of selectable marker capable of being used in systems to select transformants are those that encode the enzyme phosphinothricin acetyltransferase, such as the bar gene from *Streptomyces hygroscopicus* or the pat gene from *Streptomyces viridochromogenes*. The enzyme phosphinothricin acetyl transferase (PAT) inactivates the active ingredient in the herbicide bialaphos, phosphinothricin (PPT). PPT inhibits glutamine synthetase, (Murakami et al., 1986; Twell et al., 1989) causing rapid accumulation of ammonia and cell death. The use of bar as a selectable marker gene and for the production of herbicide-resistant rice plants from protoplasts was described by Rathore et al., (1993).

A number of *S. cerevisiae* marker genes are also known and could be used with the invention, such as, for example, the HIS4 gene (Donahue et al., 1982; GenBank number J01331). An example of an *E. coli* marker gene that has been cloned and sequenced and could be used in accordance with the invention is the Ap gene, which confers resistance to beta-lactam antibiotics such as ampacillin (nucleotides 4618 to 5478 of GenBank accession number U66885).

b.) Screenable Markers

Screenable markers that may be employed include a β-glucuronidase (GUS) or uidA gene that encodes an enzyme for which various chromogenic substrates are known; an R-locus gene, which encodes a product that regulates the production of anthocyanin pigments (red color) in plant tissues (Dellaporta et al., 1988); a β-lactamase gene (Sutcliffe, 1978), which encodes an enzyme for which various chromogenic substrates are known (e.g., PADAC, a chromogenic cephalosporin); a xylE gene (Zukowsky et al., 1983) which encodes a catechol dioxygenase that can convert chromogenic catechols; an α-amylase gene (Ikuta et al., 1990); a tyrosinase gene (Katz et al., 1983) which encodes an enzyme capable of oxidizing tyrosine to DOPA and dopaquinone which in turn condenses to form the easily-detectable compound melanin; a β-galactosidase gene, which encodes an enzyme for which there are chromogenic substrates; a luciferase (lux) gene (Ow et al., 1986), which allows for bioluminescence detection; an aequorin gene (Prasher et al., 1985) which may be employed in calcium-sensitive bioluminescence detection; or a gene encoding for green fluorescent protein (Sheen et al., 1995; Haseloff et al., 1997; Reichel et al., 1996; Tian et al., 1997; WO 97/41228).

Genes from the maize R gene complex can also be used as screenable markers. The R gene complex in maize encodes a protein that acts to regulate the production of anthocyanin pigments in most seed and plant tissue. Maize strains can have one, or as many as four, R alleles that combine to regulate pigmentation in a developmental and tissue specific manner. Thus, an R gene introduced into such cells will cause the expression of a red pigment and, if stably incorporated, can be visually scored as a red sector. If a maize line carries dominant alleles for genes encoding for the enzymatic intermediates in the anthocyanin biosynthetic pathway (C2, A1, A2, Bz1 and Bz2), but carries a recessive allele at the R locus, transformation of any cell from that line with R will result in red pigment formation. Exemplary lines include Wisconsin 22 which contains the rg-Stadler allele and TR112, a K55 derivative which is r-g, b, P1. Alternatively, any genotype of maize can be utilized if the C1 and R alleles are introduced together.

Another screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It also is envisioned that this system may be developed for populational screening for bioluminescence, such as on tissue culture plates, or even for whole plant screening. The gene that encodes green fluorescent protein (GFP) is contemplated as a particularly useful reporter gene (Sheen et al., 1995; Haseloff et al., 1997; Reichel et al., 1996; Tian et al., 1997; WO 97/41228). Expression of green fluorescent protein may be visualized in a cell or plant as fluorescence following illumination by particular wavelengths of light.

c.) Negative Selectable Markers

Introduction of genes encoding traits that can be selected against may be useful for eliminating minichromosomes from a cell or for selecting against cells that comprise a particular minichromosome. An example of a negative selectable marker that has been investigated is the enzyme cytosine deaminase (Stouggard, 1993). In the presence of this enzyme the compound 5-fluorocytosine is converted to 5-fluorouracil which is toxic to plant and animal cells. Therefore, cells comprising a minichromosome with this gene could be directly selected against. Other genes that encode proteins that render the plant sensitive to a certain compound will also be useful in this context. For example, T-DNA gene 2 from *Agrobacterium tumefaciens* encodes a protein that catalyzes the conversion of α-naphthalene acetamide (NAM) to α-naphthalene acetic acid (NAA) renders plant cells sensitive to high concentrations of NAM (Depicker et al., 1988).

VIII. Definitions

As used herein, the term "array" refers to a collection of nucleic acid sequences from which specific sequences or subsets of sequences can be identified. The array can comprise DNA sequences bound to a solid support and can also include DNA compositions in solution in suitable containers. The nucleic acid sequences need not be arranged in any particular order in the array, and may, for example, represent the random order of clones lifted from growth medium onto a filter. The nucleic acid sequences will preferably be at a known location such that the identity of the clone or nucleic acid detected at a particular location will be known. Alternatively, a pattern such as a grid or other arrangement may be used to facilitate identification of the source nucleic acid at a location on the array.

As used herein, the terms "autonomous replicating sequence" or "ARS" or "origin of replication" refer to an origin of DNA replication recognized by proteins that initiate DNA replication.

As used herein, the terms "binary BAC' or "binary bacterial artificial chromosome" refer to a bacterial vector that contains the T-DNA border sequences necessary for *Agrobacterium* mediated transformation (see, for example, Hamilton et al., 1996; Hamilton, 1997; and Liu et al., 1999.)

As used herein, the term "candidate centromere sequence" refers to a nucleic acid sequence believed to be of centromere origin and that may be assayed for potential centromere function.

As used herein, the term "centromere-associated protein" refers to a protein encoded by the genome which binds to the centromere, either to the centromere DNA itself or to other centromere-associated proteins.

As used herein, a "centromere nucleic acid sequence" is any DNA sequence that confers an ability to segregate to daughter cells through cell division. In one context, this sequence may produce a segregation efficiency to daughter cells ranging from about 1% to about 100%, including to about 5%, 10%, 20%, 30%, 40%, 50%, 60%, 70%, 80%, 90% or about 95% of daughter cells. Variations in such a segregation efficiency may find important applications within the scope of the invention; for example, mini-chromosomes carrying centromeres that confer 100% stability could be maintained in all daughter cells without selection, while those that confer 1% stability could be temporarily introduced into a transgenic organism, but be eliminated when desired. In particular embodiments of the invention, the centromere may confer stable segregation of a nucleic acid sequence, including a recombinant construct comprising the centromere, through mitotic or meiotic divisions, including through both meiotic and meiotic divisions.

As used herein, the term "digested DNA" refers to DNA that, when exposed to an endonuclease, produces fragments smaller than the genomic average of DNA that has been exposed to the endonuclease.

As used herein, the term "epigenetic" refers to a heritable trait that is not due to DNA sequence itself.

As used herein, the term "euchromatin" refers to a chromosome region that is not highly condensed.

As used herein, "eukaryote" refers to living organisms whose cells contain nuclei. A eukaryote may be distinguished from a "prokaryote" which is an organism that lacks nuclei. Prokaryotes and eukaryotes differ fundamentally in the way their genetic information is organized, as well as their patterns of RNA and protein synthesis.

As used herein, the term "expression" refers to the process by which a structural gene produces an RNA molecule, typically termed messenger RNA (mRNA). The mRNA is typically, but not always, translated into polypeptide(s).

As used herein, the terms "fluorescent in situ hybridization" or "FISH" refer to the DNA detection method wherein fluorescently labeled nucleic acid segments are hybridized to their complement.

As used herein, the term "genome" refers to all of the genes and DNA sequences that comprise the genetic information within a given cell of an organism. Usually, this is taken to mean the information contained within the nucleus, but also includes the organelles.

As used herein, the term "heterochromatin" refers to a chromosome region that is highly condensed.

As used herein, the term "hemimethylated" refers to the situation wherein DNA has a methyl group on one strand and no methyl on the complementary strand. Hemimethylation can occur at a single nucleotide or over short or long regions.

As used herein, the term "higher eukaryote" means a multicellular eukaryote, typically characterized by its greater complex physiological mechanisms and relatively large size. Generally, complex organisms such as plants and animals are included in this category. Preferred higher eukaryotes to be transformed by the present invention include, for example, monocot and dicot angiosperm species, gymnosperm species, fern species, mosses, plant tissue culture cells of these species, animal cells and algal cells. It will of course be understood that prokaryotes and eukaryotes alike may be transformed in accordance with the invention.

As used herein, the term "hybridization" refers to the pairing of complementary RNA and DNA strands to produce an RNA-DNA hybrid, or alternatively, the pairing of two DNA single strands from genetically different or the same sources to produce a double stranded DNA molecule.

As used herein, the term "hybridization filter" refers to an object to which nucleic acids can be fixedly attached, and to which probes may be hybridized, for example, in Southern Hybridization. Exemplary hybridization filters will be made of nitrocellulose or nylon, although any other materials may potentially also be used.

As used herein, the term "isoschizomer" refers to a restriction endonuclease enzyme that recognizes and binds to the same recognition sequence as another restriction endonuclease, but is isolated from different microbial sources. The restriction endonuclease isoschizomers may or may not cleave in the exact location as the restriction endonuclease with which it is being compared.

As used herein, a "library" is a collection of cloned DNA fragments. In principle, any nucleic acid sequence can be isolated by screening the library with a specific hybridization probe (see, for example, Young et al., 1977). Each library may contain the DNA of a given organism inserted as discrete restriction endonuclease-generated fragments or as randomly sheered fragments cloned into many thousands of vectors. For purposes of the present invention, E. coli, yeast, and Salmonella plasmids are particularly useful when the genome inserts come from other organisms.

As used herein, the term "lower eukaryote" refers to a eukaryote characterized by a comparatively simple physiology and composition, and most often unicellularity. Examples of lower eukaryotes include flagellates, ciliates, and yeast.

As used herein the term "methylated nucleic acid segment" or "methylated DNA segment" refers to a DNA segment containing methylated bases in a target species at a frequency greater than the genomic average or in a different pattern than the genomic average, such as in the case of hemimethylated DNA. The term includes sequences that are complementary to methylated sequences but are not necessarily themselves methylated. For example, non-methylated amplification products of methylated genomic DNA segments may be prepared from methylated sequences.

As used herein the term "methylation sensitive restriction endonuclease" refers to a restriction endonuclease with a decreased capacity to cleave methylated DNA relative to unmethylated DNA.

As used herein, the term "microscope slide" refers to an object similar to a standard slide used for holding a specimen to be observed under a microscope. The microscope slide will preferably be made of glass or a similar material and will have a flat surface, however, it will be understood to those of skill in the art that various trivial modifications may be made to a typical microscope slide and still not depart from the scope and meaning of the term as defined in the current invention.

As used herein, the term "plant" includes plant cells, plant protoplasts, plant calli and the like, as well as whole plants regenerated therefrom.

As used herein, the term "plasmid" or "cloning vector" refers to a closed covalently circular extrachromosomal DNA or linear DNA that is able to autonomously replicate in a host cell and which is normally nonessential to the survival of the cell. A wide variety of plasmids and other vectors are known and commonly used in the art (see, for example, Cohen et al., U.S. Pat. No. 4,468,464, which discloses examples of DNA plasmids, and which is specifically incorporated herein by reference).

As used herein, the term "pool" or "DNA pool" refers to a composition of DNA made from the combination of DNA from sources, such as individual cells, clones or individual. The pool will typically be constructed to allow the identification of individuals desired genetic sequence from a population of sequences without the need to individually screening every individual sequence within that population. For example, pools of clones of genomic DNA could be used to greatly reduce the size of an array needed to allow the detection of a specific clone or clones comprising a given nucleic acid sequence from a genome.

As used herein, a "probe" is any biochemical reagent (usually tagged in some way for ease of identification), used to identify or isolate a gene, a gene product, a DNA segment or a protein.

As used herein the term "regulatory sequence" refers to any DNA sequence that influences the efficiency of transcription or translation of any gene. The term includes, but is not limited to, sequences comprising promoters, enhancers and terminators.

As used herein, the terms "satellite" or "satellite elements" refer to DNA sequences repeated in homogeneous or heterogeneous mixtures in multiples of three or more copies.

As used herein, a "selectable marker" is a gene the presence of which results in a clear phenotype, and most often a growth advantage for cells that contain the marker. This growth advantage may be present under standard conditions, altered conditions such as elevated temperature, or in the presence of certain chemicals such as herbicides or antibiotics. Use of selectable markers is described, for example, in Broach et al. (1979). Examples of selectable markers include the thymidine kinase gene, the cellular adenine-phosphoribosyltransferase gene and the dihydrylfolate reductase gene, hygromycin phosphotransferase genes, the bar gene and neomycin phosphotransferase genes, among others. Preferred selectable markers in the present invention include genes whose expression confer antibiotic or herbicide resistance to the host cell, sufficient to enable the maintenance of a vector within the host cell, and which facilitate the manipulation of the plasmid into new host cells. Of particular interest in the present invention are proteins conferring cellular resistance to ampicillin, chloramphenicol, tetracycline, G-418, bialaphos, and glyphosate for example.

As used herein, a "screenable marker" is a gene whose presence results in an identifiable phenotype. This phenotype may be observable under standard conditions, altered conditions such as elevated temperature, or in the presence of certain chemicals used to detect the phenotype.

As used herein, the term "selected species" refers to any species that one desires to obtain a centromere nucleic acid sequence.

As used herein, the term "strand-specific methylation sensitive restriction endonuclease" refers to a restriction endonuclease that preferentially cuts hemimethylated DNA on the methylated strand.

As used herein, the term "telomere" refers to a sequence capable of capping the ends of a chromosome, thereby reducing degradation of the chromosome end.

As used herein, the terms "transformation" or "transfection" refer to the acquisition in cells of new DNA sequences through the chromosomal or extra-chromosomal addition of DNA. This is the process by which naked DNA, DNA coated with protein, DNA modified by methylation, or whole minichromosomes are introduced into a cell, resulting in a potentially heritable change.

IX. EXAMPLES

The following examples are included to demonstrate preferred embodiments of the invention. It should be appreciated by those of skill the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Isolation of Centromere Sequences

The methods described herein in Example 3 were used to successfully to isolate centromere DNA from *Arabidopsis thaliana* of the Columbia and Dijon ecotype. First, the CTAB method was used to extract high quality genomic DNA according to the method described in Example 3A. Using the methylation sensitive enzyme Hpa II, genomic DNA was cleaved and separated into different size fragments on an agarose gel as described in Example 3B. Highly methylated DNA (>5 Kb fragments) and unmethylated DNA or DNA with low levels of methylation (<5 Kb fragments) were isolated from the gel.

A Columbia (7.5× coverage of the genome) and a Dijon BAC library (2.6× coverage of the genome) filters from the TAMU BAC center (Texas A&M University) were then probed individually with $^{32}P$ labeled methylated and unmethylated DNA fragments using the procedure set forth in Example 3C. In the study with the Dijon library 304 BACs were identified by the highly methylated DNA probe. 101 of the BAC clones were also detected using the unmethylated probe and thus were eliminated, yielding a total of 203 potential centromere BACs identified by the hybridizations. To confirm that the identified BACs included centromere sequences, BAC end sequencing was carried out on 45 randomly selected BACs. Sequencing and BLAST results indicated that that 42 of the 45 randomly selected BACs, or over 93%, mapped to the centromere.

Example 2

Detection of Methylated Centromere Sequences

Known centromere sequences from *Arabidopsis* were used to analyze the abundance and patterns of methylation in centromeres. In *Arabidopsis*, over 5 Mb of sequence from the centromeric regions have been obtained, more than from any other higher eukaryote to date (see, e.g., "The *Arabidopsis* Genome Initiative," Nature 408, 796, 2000; Copenhaver et al., 1999). The results of the study demonstrated that, unlike other heterochromatic portions of the genome, *Arabidopsis* centromeres contain distinct methylation profiles.

A. Sequencing Demonstrates Heavy Methylation of Centromere DNA.

Bisulfite sequencing, a method that allows direct assessment of methylation status, was used to demonstrate that the centromere regions of *Arabidopsis* contain high levels of methylation. This methylation was found to occur on cytosines in all possible contexts (e.g., CpG, CpNpG, or CpNpN). For the analysis, several sequences were analyzed from centromeres, as well as sequences from the chromosome arms (see FIG. 1 and Table 1). The results were repeated twice with seedlings from the Columbia strain and were confirmed in seedlings from the Ws strain, as well as in other tissues from Columbia. The study was carried out as follows.

DNA sequencing was performed after treating genomic DNA with bisulfite, a method that converts non-methylated cytosines to uracil (Frommer et al., 1992). 10 ug of seedling genomic DNA was sheared into 1–2 kb fragments, denatured in 0.1 M NaOH (15 min, 20° C.), neutralized and ethanol precipitated. Non-methylated cytosines were deaminated in 1.2 ml of 4M $NaHSO_3$, 500 μM hydroquinone, pH 5.0 at 50° C. for 24 hrs. DNA was purified on a gel filtration column, incubated in 0.3 M NaOH (10 min, 20° C.), and ethanol precipitated. For each locus analyzed, separate amplifications of the upper and lower strands were carried out with unidirectional PCR. To eliminate biased amplification of methylated strands, primers were used corresponding to regions lacking cytosine residues. Ten independent amplifications were performed per locus, and the products were cloned and sequenced (Luff et al., 1999; Nagane et al., 2000).

Several CENTROMERE 2 (CEN2) sequences (e.g., genes, pseudogenes, non-coding unique sequences and satellites; Copenhaver et al., 1999) were amplified, as were portions of other *Arabidopsis* centromeres (CEN1–5), non-centromeric heterochromatin (rDNA from NOR2), a repetitive knob from chromosome 4 (Copenhaver and Pikaard, 1996; Fransz et al., 2000) and two euchromatic genes (SUPERMAN, K14B15.1, from chromosome 3, and T28P16.15 from chromosome 2; Jacobsen and Meyerowitz, 1997; Lin et al., 1999). Data obtained from the same batches of bisulfite treated genomic DNA, extracted from thousands of 5 day old seedlings of the Columbia ecotype, were compared (Table 1). The results demonstrated the heavy methylation of centromere sequences. Studies using seedlings of the Ws strain or Columbia ecotype tissues collected at different developmental stages yielded similar data.

B. DNA Sequencing Demonstrated that the Pattern of Centromere Methylation Sometimes Shows Strand Specificity.

DNA sequencing revealed that some, but not all, centromere regions exhibited a strand-specific methylation pattern. This type of methylation (hemimethylation) has been observed before in newly replicated DNA, where up to 50% of any given cytosine can be methylated. However, the extent of hemimethylation observed in centromeres was different, with as much as 100% hemimethylation. This pattern of hemimethylation appears to be unique to centromeres, as it was not seen in other DNA analyzed (FIG. 2, Table 1).

Surprisingly, methylation levels were often found to differ dramatically when the upper and lower strands from the centromeric and pericentromeric regions were compared (FIG. 1). In a representative chromatogram (FIG. 1A), only a few cytosines in the upper strand were methylated, whereas every cytosine in the lower strand was methylated. This pattern was more apparent when several independent clones of the same sequence were examined. Amplified fragments revealed 81% and 17% methylation of cytosines in the lower and upper strands, respectively (FIG. 1B). Because these products were amplified from the same bisulfite-treated DNA sample, they reflect the average methylation status of a population of growing cells.

Examination of multiple sequences showed methylation in the centromeric regions was often strongly biased toward one strand, with one strand often displaying very limited levels of methylation. These differences were highly significant, ranging between 1.7 and 136 fold (Table 1A). Unlike the CpG methylation typical of mammalian cells, plant DNA methyltransferases can also modify cytosines in other contexts (CWG or CH: W=A or T and H=A, T or C) (Jacobsen and Meyerowitz, 1997). In the centromere regions, highly significant strand biases in non-CpG methylation were detected, whereas CpG methylation was sometimes distributed on both strands (Table 1A), suggesting that different methyltransferases vary in their reactivity with centromere DNA. These biases occurred in all types of sequences, whether coding or non-coding, including a recently inserted mitochondrial DNA sequence within CEN2 (Copenhaver et al., 1999). Biases in methylation of DNA strands were observed previously in the Dc8 gene of carrot (Zhou et al., 1998) and in the promoter of a human retrotransposon (Woodcock et al., 1997). The broad distribution of biased methylation found in the *Arabidopsis* centromeres suggests that the location or context of the sequences, and not the sequences themselves, triggers strand-specific DNA methylation.

To determine whether the methylation patterns observed in the centromeres were a consequence of their heterochromatic states, the 18S-25S rDNA spacer in NOR2 and the knob on chromosome 4 were examined (Copenhaver and Pikaard, 1996; Fransz et al., 2000). These sequences contained similar levels of methylation on both DNA strands, (rDNA, 80 and 84%, respectively; knob, 46 and 67%, respectively) (Table 1B). Some centromeric and pericentromeric sequences showed a similar pattern, with both DNA strands carrying substantial levels of methylation (Table 1B). As expected, the euchromatic regions contained very little methylation. Integrating these data with the physical and genetic maps of chromosome 2 showed that high levels of methylation were present in all heterochromatic regions, yet the genetically-defined centromere and the nearby pericentromeric regions (Copenhaver et al., 1999) uniquely contained one DNA strand with low methylation levels, resulting in a strong asymmetry (FIG. 2A). These observations indicated that heterochromatic DNA alone is not a signal for biases in strand methylation.

The observed methylation status of selected portions of the *Arabidopsis* genome is provided in Table 1, below. The analyzed DNA sequences (numbered 1–20) are indicated by location on a sequenced BAC or P1 clone, locus on a given chromosome (centromere, CEN; pericentromere, PeriCen; euchromatin, EuChr; nucleolar organizing region, NOR), nucleotide position on the complete chromosome sequence, and type (nMito, an integrated portion of the mitochondrial genome; satellite, 180 bp repeat; knob, a heterochromatic repeat (The *Arabidopsis* Genome Initiative, Nature 408, 796, 2000)). Percent cytosine methylation is reported for each strand (upper and lower rows, respectively) as an average (±standard deviation) from ten independent clones and is divided into sub-categories CG, CWG (W=A or T), or CH (H=A or T or C) or summed (total); n is the total number of cytosines in the sequence; fold difference is the ratio of average methylation on the upper and lower strands.

TABLE 1

Observed methylation status of selected portions of the *Arabidopsis* genome.

| | BAC (locus) | Position | Type | % Methylation (n) CG | % Methylation (n) CWG | % Methylation (n) CH | % Methylation (n) Total | Fold Difference |
|---|---|---|---|---|---|---|---|---|
| A | | | | | | | | |
| 1. | T13E11 (CEN2) | 3028750–3029080 | gene | 98 ± 5.3 (60) | 94 ± 9.7 (50)** | 75 ± 13 (520)*** | 78 ± 11 (630)*** | 1.9 |
| | | | | 87 ± 23 (60) | 72 ± 19 (50) | 29 ± 32 (520) | 41 ± 28 (630) | |
| 2. | T5M2 (CEN2) | 3217479–3217830 | non-coding | 90 ± 17 (40) | 23 ± 25 (40)*** | 14 ± 26 (560)*** | 19 ± 24 (640)*** | 4.1 |
| | | | | 95 ± 11 (40) | 80 ± 16 (40) | 78 ± 8.0 (460) | 79 ± 7.1 (540) | |
| 3. | T5E7 (CEN2) | 3508767–3509077 | nMito | 83 ± 21 (60) | 58 ± 31 (60)* | 34 ± 35 (390)* | 43 ± 31 (510)* | 1.7 |
| | | | | 97 ± 7.0 (60) | 83 ± 18 (60) | 67 ± 33 (550) | 71 ± 29 (670) | |
| 4. | T12J2 (CEN2) | 3595356–3595661 | non-coding | 40 ± 38 (30)*** | 33 ± 28 (60)*** | 13 ± 22 (340)*** | 17 ± 22 (430)*** | 4.7 |
| | | | | 93 ± 14 (30) | 95 ± 8.1 (60) | 80 ± 12 (460) | 83 ± 11 (550) | |
| 5. | T14C8 (CEN2) | 3809181–3809652 | satellite | 100 ± 0.0 (70)* | 100 ± 0.0 (30)*** | 89 ± 4.3 (760)*** | 91 ± 3.8 (860)*** | 3.1 |
| | | | | 82 ± 21 (70) | 60 ± 26 (30) | 21 ± 25 (590) | 29 ± 23 (690) | |
| 6. | T14C8 (CEN2) | 3818592–3818854 | pseudogene | 0.0 ± 0.0 (130)*** | 1.3 ± 4.0 (80)*** | 0.5 ± 1.1 (380)*** | 0.5 ± 1.1 (590)*** | 136 |
| | | | | 66 ± 28 (130) | 75 ± 26 (80) | 69 ± 26 (310) | 69 ± 25 (520) | |
| 7. | F12P23 (PeriCen2) | 4168299–4168613 | non-coding | 11 ± 26 (150)*** | 10 ± 32 (20)*** | 9.3 ± 25 (410)*** | 9.8 ± 25 (580)*** | 8.3 |
| | | | | 74 ± 22 (150) | 90 ± 21 (20) | 82 ± 13 (600) | 81 ± 14 (770) | |
| 8. | F23H6 (CEN3) | 13978956–13979219 | gene‡ | 100 ± 0.0 (20) | 100 ± 0.0 (40)** | 89 ± 7.6 (670)** | 90 ± 7.0 (730)** | 2.1 |
| | | | | 90 ± 21 (20) | 58 ± 39 (40) | 37 ± 42 (290) | 43 ± 39 (350) | |
| 9. | T14A11 (CEN3) | 14302655–14302385 | non-coding | 98 ± 5.3 (60)* | 91 ± 18 (70)*** | 80 ± 23 (530)** | 83 ± 20 (660)*** | 2.8 |
| | | | | 83 ± 19 (60) | 36 ± 39 (70) | 17 ± 32 (290) | 30 ± 28 (420) | |
| 10. | T3P1 (CEN5) | 3689–3857† | non-coding | 90 ± 32 (30) | 0 (0) | 76 ± 40 (210)* | 78 ± 38 (240)* | 1.9 |
| | | | | 90 ± 23 (30) | 0 (0) | 34 ± 43 (240) | 40 ± 39 (270) | |
| B | | | | | | | | |
| 11. | T25N22 (PeriCen2) | 2924911–2925241 | gene | 49 ± 36 (70) | 51 ± 46 (80) | 44 ± 38 (440) | 45 ± 39 (590) | 1.4 |
| | | | | 44 ± 42 (70) | 40 ± 39 (80) | 30 ± 28 (440) | 33 ± 30 (590) | |
| 12. | T5M2 (CEN2) | 3237818–3238247 | nMito | 98 ± 3.7 (130) | 92 ± 6.7 (110) | 67 ± 24 (610) | 75 ± 17 (850) | 1.1 |
| | | | | 95 ± 5.4 (130) | 92 ± 12 (110) | 80 ± 16 (600) | 84 ± 12 (840) | |
| 13. | F7B19 (CEN2) | 3930056–3930457 | gene | 43 ± 40 (170)* | 48 ± 47 (110) | 46 ± 43 (440) | 46 ± 42 (720) | 1.7 |
| | | | | 76 ± 20 (170) | 76 ± 21 (110) | 75 ± 16 (670) | 76 ± 16 (950) | |
| 14. | F9D18 (CEN1) | 1936–2230† | non-coding | 98 ± 5.7 (170) | 86 ± 21 (100) | 60 ± 42 (410) | 73 ± 29 (680) | 1.4 |
| | | | | 84 ± 25 (170) | 68 ± 19 (100) | 36 ± 32 (370) | 54 ± 23 (320) | |
| 15. | F2112 (CEN4) | 3001709–3001151 | non-coding | 98 ± 3.0 (240) | 100 ± 0.0 (80)* | 87 ± 9.7 (810) | 90 ± 7.0 (1130) | 1.0 |
| | | | | 99 ± 1.8 (240) | 89 ± 15 (80) | 88 ± 7.2 (1090) | 90 ± 6.0 (1410) | |
| 16. | F14G16 (CEN4) | 3054014–3054466 | non-coding | 90 ± 23 (30) | 0 (0) | 41 ± 35 (370) | 44 ± 33 (400) | 1.3 |
| | | | | 97 ± 11 (30) | 0 (0) | 55 ± 47 (300) | 59 ± 43 (330) | |
| 17. | T5H22 (PeriCen4) | 1740680–1741177 | knob | 92 ± 14 (120) | 48 ± 20 (80)** | 36 ± 34 (560) | 46 ± 27 (760) | 1.4 |
| | | | | 96 ± 5.9 (120) | 74 ± 20 (80) | 62 ± 30 (790) | 67 ± 25 (990) | |
| 18. | F23H14 (NOR2) | 2421–2999 | rDNA | 93 ± 10 (400) | 94 ± 5.6 (120) | 72 ± 17 (810) | 80 ± 12 (1330) | 1.0 |
| | | | | 91 ± 13 (400) | 93 ± 6.6 (120) | 80 ± 11 (980) | 84 ± 11 (1500) | |
| 19. | K14B15 (EuChr3) | 8242470–8242680 | | 0.0 ± 0.0 (20) | 0.0 ± 0.0 (90) | 0.0 ± 0.0 (360) | 0.0 ± 0.0 (470) | NA |
| | | | | 0.0 ± 0.0 (20) | 0.0 ± 0.0 (90) | 0.0 ± 0.0 (360) | 0.0 ± 0.0 (470) | |
| 20. | T28P16 (EuChr2) | 13521833–13522177 | gene | 0.0 ± 0.0 (60) | 0.0 ± 0.0 (40) | 0.5 ± 1.0 (430) | 0.4 ± 0.8 (530) | 4.8 |
| | | | | 0.0 ± 0.0 (60) | 0.0 ± 0.0 (40) | 2.1 ± 5.5 (520) | 1.8 ± 4.6 (620) | |

Grey shading indicates statistically significant differences between strands (T-test, P < 0.05). T-test values of greater significance are indicated by
*(P = 0.05–0.01),
**(P = 0.009–0.001),
***(P < 0.001).
†Sequences not included in the complete chromosome sequence (The *Arabidopsis* Genome Initiative, Nature 408, 796, 2000) are indicated by nucleotide position in the corresponding BAC clone;
‡retroelement polyprotein;
NA, not applicable.

C. Development of an Efficient Method for Assessing the Extent of Hemimethylation within the Centromeres.

In addition to DNA sequencing, restriction analysis was used to determine the extent of methylation of centromere DNA. This method makes it possible to use nearly any restriction endonuclease to monitor the extent of methylation of a sequence, and to assess whether the DNA is fully methylated or hemimethylated (see FIG. 3). This approach alleviates the need for time consuming, labor intensive and expensive PCR product cloning and sequencing. The technique can be carried out by preparing DNA, treating a portion of the DNA with bisulfite (e.g., converting "C" nucleotides to "T", but not affecting "methyl-C" nucleotides), using strand-specific amplification and PCR to make several copies of a region of interest, cutting the DNA with a restriction endonuclease and comparing the patterns of digestion between DNA treated with bisulfite and untreated DNA.

Figure 3:
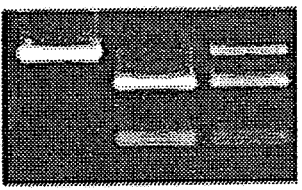
FIG. 3. Restriction endonuclease assay for hemimethylated DNA. PCR products from selected regions are numbered as in Table 1, and the restriction endonuclease used is indicated. Primers were designed to survey the same restriction site on the upper and lower strands, differences in primer location sometimes resulted in different product lengths.

Genomic restriction endonuclease sites containing methylated cytosine residues are not altered by bisulfite treatment, and consequently, PCR products amplified from these regions can be completely digested. For example, it was found that NOR2 was heavily methylated, and bisulfite-treated genomic DNA yielded PCR products from either the upper or lower strands that yielded approximately 80% digestion with Bfa I (CTAG) (FIG. 3). In contrast, bisulfite-mediated conversion of non-methylated C residues completely disrupted the EcoR I (GAATTC) site within the euchromatic SUPERMAN locus in K14B15 (FIG. 3). This method was used in an assay to assess relative methylation levels at an Alu I site (AGCT) on two complementary DNA strands within CEN2. By estimating the extent of product digestion, 46% methylation was found on the lower strand and no detectable methylation on the upper strand (FIG. 3). Similar results were obtained for the T14C8 (CEN2) fragment.

The DNA sequencing and restriction digestion methods described above were adequate for assessing methylation states of small regions or single nucleotides, respectively. However, the analysis of stand biases in cytosine methylation was expanded to an entire chromosome by using Sau3A I to nick hemimethylated GATC sites (Streeck, 1980) and $E.$ $coli$ DNA polymerase I to produce $^{32}P$ labeled probes. Prior to digestion with Sau3A I, nicks that occurred naturally or resulted from DNA damage during purification were blocked by incubation with the Klenow fragment and dideoxynucleotide triphosphates. The portion of the genome represented by the nick translation products was determined by hybridization to an ordered array of sequenced chromosome 2 BAC and P1 clones (FIG. 2B) (Lin et al., 1999).

In parallel, Mbo I-digested DNA was characterized. This methylation-insensitive isoschizomer produces double strand breaks at methylated or hemimethylated sites and provided a normalization standard for the Sau3A I digests. Examining the ratio of signal following Sau3A I and Mbo I cleavage made it possible to detect hemimethylated sites in both the repetitive and non-repetitive portions of the chromosome. Digestion with Sau3A I and Mbo I yielded nick translation fragments from the chromosome arm and from NOR2 in equal abundance, whereas nick translation fragments were generated at a much higher frequency from Sau3A I digested DNA in the vicinity of the centromere (FIG. 2B). Two repetitions of this study yielded similar patterns. The results strongly suggest that strand-specific DNA methylation is a unique feature of the centromeric region.

D. Detecting Strand-Specific Methylation of the Centromere Region Using Southern Hybridization.

The properties of the methylation sensitive enzyme Sau3A I were used to directly assess the extent of methylation in genomic DNA. This enzyme cuts unmethylated DNA, nicks hemimethylated DNA, and does not cut fully methylated DNA. Genomic DNA was digested with Sau3A I, the digested DNA was denatured to separate complementary strands, the DNA was run over a native agarose gel and the fragments were blotted and hybridized with probes specific for each strand. Quantitation of the resulting patterns showed unequal cleavage of the two strands, confirming hemi-methylation.

In this study, the nicking activity of Sau3A I was used to monitor hemimethylation at a restriction site in CEN2 (T14C8). Genomic DNA was digested to completion with Sau3A I, denatured and separated on an agarose gel, and strand-specific probes were used to detect fragments from the upper and lower strands on quantitative Southern blots. In two independent trials, the lower strand was cleaved more efficiently than the upper strand (% cleavage of upper:lower strands, 39:44 and 65:69, respectively; P<0.001, $\chi^2$ test). These results confirmed that hemimethylated DNA can be directly detected at centromeric sequences. The results indicate that biases in the methylation content of DNA strands in $Arabidopsis$ could be used to provide an epigenetic tag, marking regions that confer centromere functions for isolation.

E. Identifying Portions of the Genome that Contain Strand-Specific Methylation.

Sau3A I was used followed by nick translation to generate DNA fragments that correspond to the hemimethylated portions of the genome. To identify the nick translation products, those products were used as probes that were hybridized to filters containing arrays representing either chromosome 2, or the entire genome (FIG. 2B). The method was can be carried out as follows:

---

Prepare genomic DNA.
Treat the DNA with ddNTPs and Klenow to block the activity of all nicked sites.
Divide the DNA into two fractions.
Treat one fraction with Sau3A I and the other with Mbo I.
Add $^{32}P$ dNTPs and $E. coli$ DNA Polymerase I and perform nick translation.
Purify labeled nick translation products.
Use products to probe arrays of clones corresponding to genomic DNA.
Perform Southern hybridization, quantitate signal using imaging software.
Compare the ratio of signal from MboI and Sau3A I, regions that show substantially more signal from Sau3A I contain significant levels of hemimethylation.

---

In the method, genomic DNA is isolated with the CTAB method. For Klenow and ddNTP treatment 2 μg of genomic DNA is used, with 10× EcoPol Buffer 10 μl, 1 mM of each ddNTP (2 μl) and 5 U Klenow. Then add ddH2O to 100 μl, incubate at 37° C. for 3 hours, phenol/chloroform extract DNA followed by ethanol precipitation. For Restriction Digestion with Mbo I and Sau3A I, the reaction mixture contained 1 μg genomic DNA, 10 μl 10× Buffer, and 20 U enzyme (Mbo I or Sau3A) with ddH$_2$O added to make 100 μl. Additionally, for Sau3A digestion, 1 μl BSA was added. The solution was incubated at 37° C. for 6 hours. DNA was isolated by phenol/chloroform extraction and ethanol precipitation. Labeled probe was prepared in a solution of 1 μg digested genomic DNA (e.g., with Mbo I or Sau3A I), 5 μl 10× EcoPol Buffer, 1 μl d(A.T.G)TP mix (1 mM each), 5 μl $^{32}$P-dCTP, 10 U E. coli DNA Polymerase I, and ddH$_2$O to 50 µl. The mixture was incubated at 16° C. for 1 hour, followed by purification of probes and Southern blotting.

Example 3

Materials and Methods

A. Isolation of Genomic DNA

Tissue from Arabidopsis thaliana plants of the Columbia ecotype was harvested for DNA extraction. For DNA extraction, leaf tissue was cooled in liquid nitrogen, ground to a fine powder and transferred to an organic solvent-resistant test tube or beaker. Warm 2-ME/CTAB extraction solution (2% (w/v) CTAB, 100 mM Tris-Cl, pH 8.0, 20 mM EDTA, pH 8.0, 1.4 M NaCl, 2% β-mercaptoethanol) was added and mixed thoroughly and incubated for 10–60 min. at 65° C. with occasional mixing. The homogenate was extracted with an equal volume of 24:1 chloroform/octanol or chloroform/isoamyl alcohol, and was then centrifuged 5 min at 7500×g (8000 rpm in JA20; 10,000 rpm in a microcentriftige, for smaller samples), 4° C. The top (aqueous) phase was recovered and ⅒ volume 65° C. CTAB/NaCl solution was added. A second extraction with an equal volume of chloroform/octanol was performed as before and the aqueous phase was recovered. Nucleic acids were precipitated by adding 1 volume CTAB precipitation solution (1% (w/v) CTAB, 50 mM Tris-Cl, pH 8.0, 10 mM EDTA, pH 8.0). The precipitate was centrifuged for 5 min at 500×g (2000 rpm in JA-20; ~2700 rpm in microcentrifuge), 4° C. The supernatant was removed and the pellet resuspended in high salt TE buffer (0.5 to 1 ml per gram of starting material). The nucleic acids were precipitated by adding 0.6 volumes of isopropanol. After mixing, the precipitate was pelleted at 15 min at 7500×g, 4° C. The pellet was washed with 80% ethanol, dried and resuspended in a minimal volume of TE (10 mM Tris-Cl, pH 8.0, 0.1 mM EDTA, pH 8.0).

B. Restriction Digestion and Isolation of Methylated DNA

For restriction digests, approximately 20–40 µg of total Arabidopsis genomic DNA was added to a 200 µl reaction volume using the manufacturer's suggested buffers (New England Biolabs for HpaII and MspI) and 10–200 units of enzyme per digest. Spermidine (1 mM) and acetylated bovine serum albumin (BSA) (NEB, 0.1 mg ml$^{-1}$) can be added to aid digestion. The HpaII and MspI reactions were incubated overnight at 37° C. The digested genomic DNA samples were size-fractionated by electrophoresis through 0.6% to 1% agarose (Gibco BRL) gels.

The largest fraction of DNA, making up the methylated DNA, was isolated from the gel. Typically, this comprised fragments having a size larger than 5 kb following digestion with the methylation sensitive restriction endonuclease. The DNA was then isolated from the gel using a QiaEXII kit (Qiagen, Inc.) following the manufacturers instructions. Alternatively, bands were identified which were present in the sample using the methylation sensitive restriction digest but not the nonmethylation sensitive digest. For isolation of non-methylated nucleic acids, typically fragments smaller than 5 kb, and more preferably, smaller than 3 kb were selected from the methylation sensitive restriction digest.

C. Probe Preparation, Labeling and Hybridization

Nucleic acid segments obtained as described above were labeled with approximately 50 µCi of [α$^{-32}$]dCTP (Amersham) (3000 Ci/mmole) using 1 U Klenow (Boehringer Mannheim, Mannheim, Germany) overnight at room temperature. Filters were incubated within glass tubes in an hybridization oven (Techne HB-ID oven) in a volume of 50 ml. Membranes in duplicate were prehybridized for 2 hr—overnight at 65° C. in a 50 ml solution containing final concentrations of 0.5 M NaPO$_4$ (phosphate buffer) pH 7.2, 7% SDS, 1% BSA, 1 mM EDTA, and 10 µg/ml salmon sperm DNA. Hybridization of the replicate set of filters was performed overnight at 65° C. in the same solution with 1 to 20×10$^6$ cpm of $^{32}$P-radiolabeled probes. In the case of probes that contain one or more repetitive sequences that may cause non-gene specific hybridization, either unlabeled total genomic DNA, unlabeled C$_0$t-1 DNA, or unlabeled unmethylated DNA fragments may be added. This DNA will hybridize competitively with the non-centromeric repeated elements and effectively block their signal.

Figure 8A:
FIG. 8A, 8B. Comparison of results of hybridization to filters comprising *Arabidopsis* BAC genomic DNA clones using as a probe DNA that was either cut with a methylation sensitive restriction endonuclease (FIG. 8A), or exhibited resistance to the methylation sensitive restriction endonuclease (FIG. 8B). The results show differential detection of clones comprising DNA from methylated portions of the genome relative to the clones from unmethylated portions of the genome.
Figure 8B:
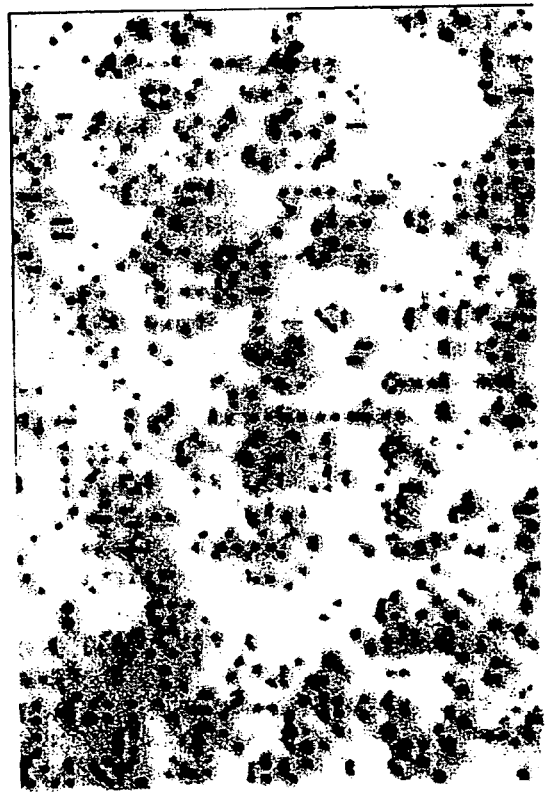
Figure 11:
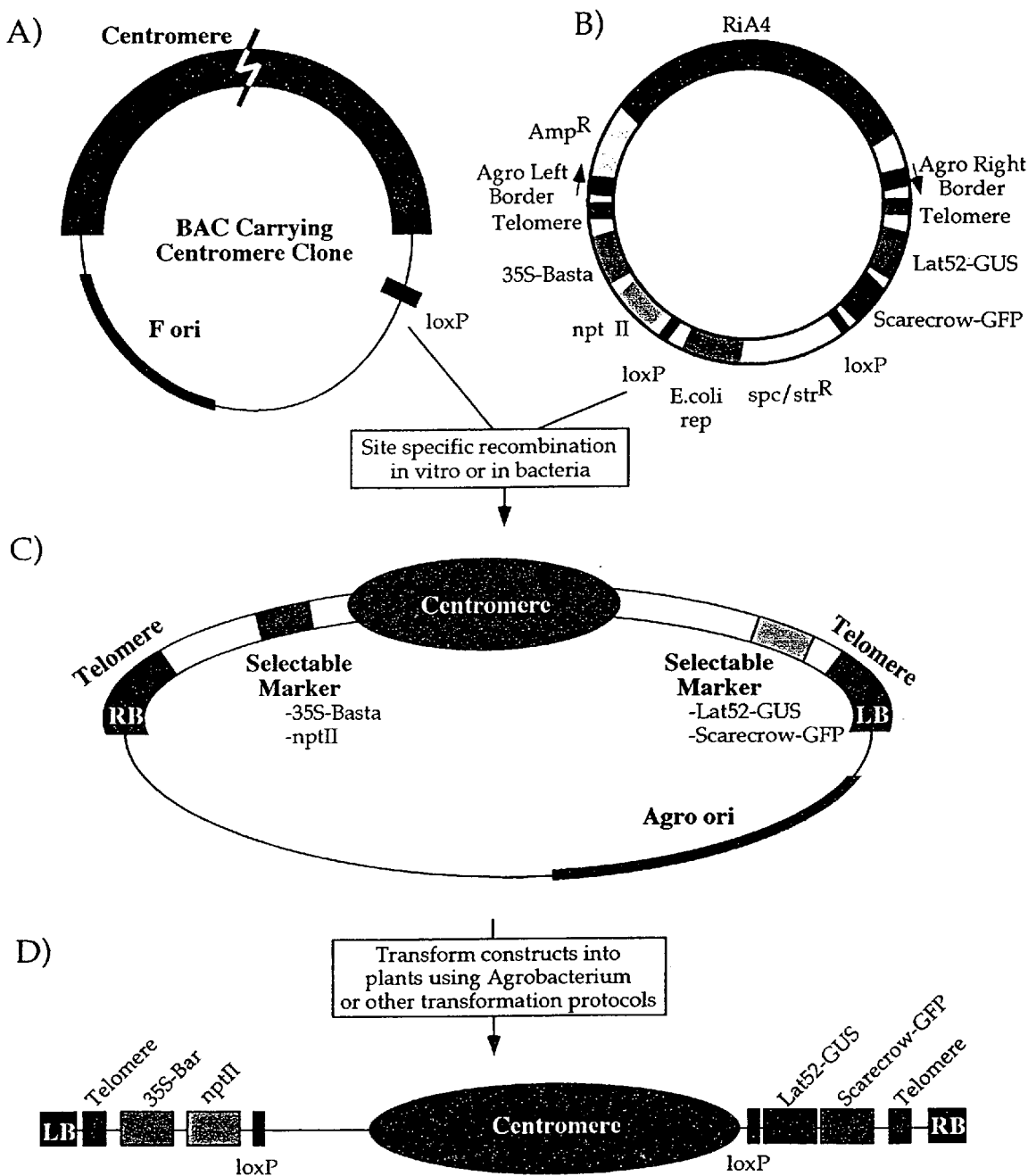
FIG. 11. Additional methods for converting a BAC clone containing centromere DNA into a minichromosome for introduction into cells. The specific elements described are provided for exemplary purposes and are not limiting or required for use in a minichromosome. A) diagram of the BAC clone, noting the position of the centromere DNA, a site-specific recombination site (for example, lox P), and the F origin of replication. B) Conversion vector containing selectable and color markers (for example, 35S-Bar, nptII, LAT52-GUS, Scarecrow-GFP), telomeres, a site-specific recombination site (for example, lox P), antibiotic resistance markers (for example, amp or spc/str), *Agrobacterium* T-DNA borders (Agro Left and Right) and origin of replication (RiA4). C) The product of site specific recombination with the Cre recombinase at the lox P sites yields a circular product with centromeric DNA and markers flanked by telomeres. D) Minichromosome immediately after transformation; subsequently, the left and right borders will likely be removed by the cell and additional telomeric sequence added by the telomerase.
Figure 12:
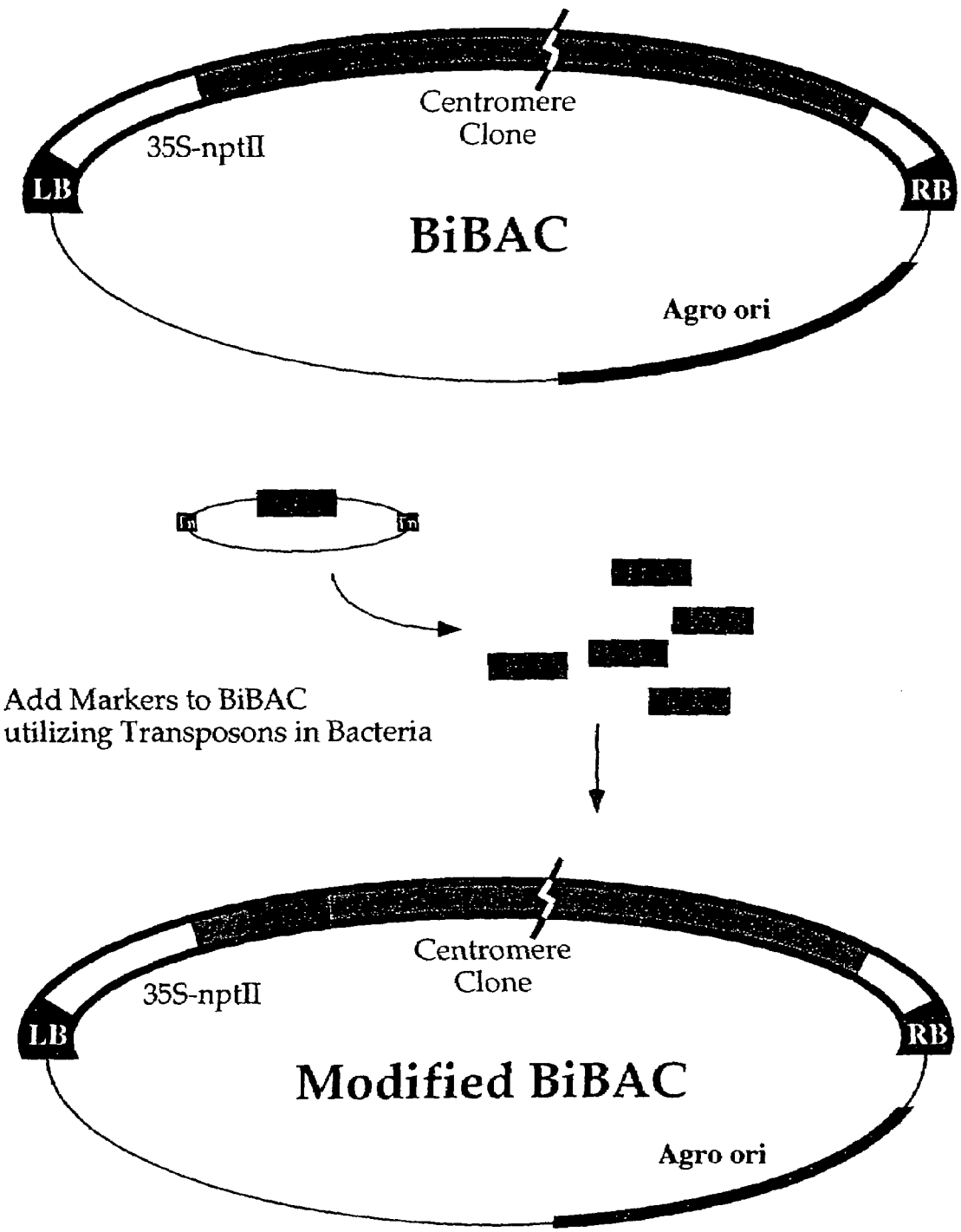
FIG. 12. Exemplary methods for adding selectable or screenable markers to BiBAC clones. The desired marker is flanked by transposon borders, and incubated with the BiBAC in the presence of transposase. Subsequently, the BiBAC is introduced into cells. Often these BiBACs may integrate into a natural chromosome, creating a dicentric chromosome which may have altered stability and may cause chromosome breakage, resulting in novel chromosome fragments. Alternatively, they could be inherited as autonomous minichromosomes.

The membranes hybridized comprised two BAC libraries from A. thaliana (Mozo, et al., 1998, Choi et al., 1995). The membranes were washed 3 times for 30 min in 2×SSC/1.0% SDS. All washes were carried out at 65° C. Exposure to phosphor screens was for 2 hrs to 2 days. The hybridization signal was manually scored to identify clones containing centromere sequences (FIG. 8A, FIG. 8B, FIG. 9). Alternatively, signals could be measured with an automated device such as an array reader.

Stripping of hybridized membranes was performed by 2 to 4 successive immersions in a solution of 0.1% SDS at 65° C. for 2 hr to overnight. Membranes were rinsed in 2×SSC for 10 min at room temperature. Membranes may be used at least 20 times.

Example 4

Confirmation of Methylated Nucleic Acid Segments as Centromere Sequences

Figure 4A:
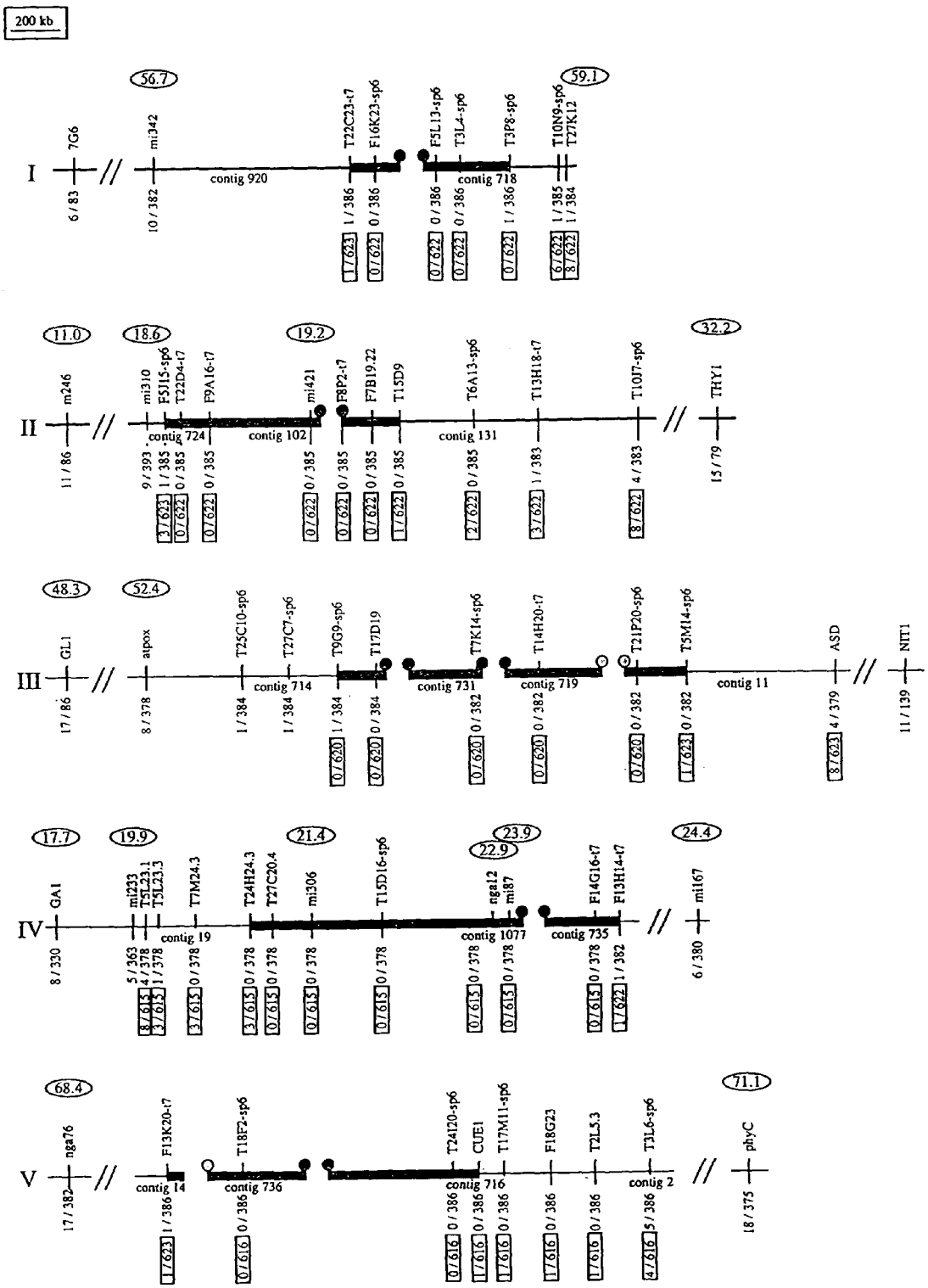
FIG. 4A, 4B. Localization of centromere sequences obtained from methylated DNA fractions on physical maps of genetically-defined *Arabidopsis* centromeres. After isolation of candidate centromere sequences using methylated DNA fractions, a study was carried out to identify clones corresponding to centromere regions.
Figure 4B:
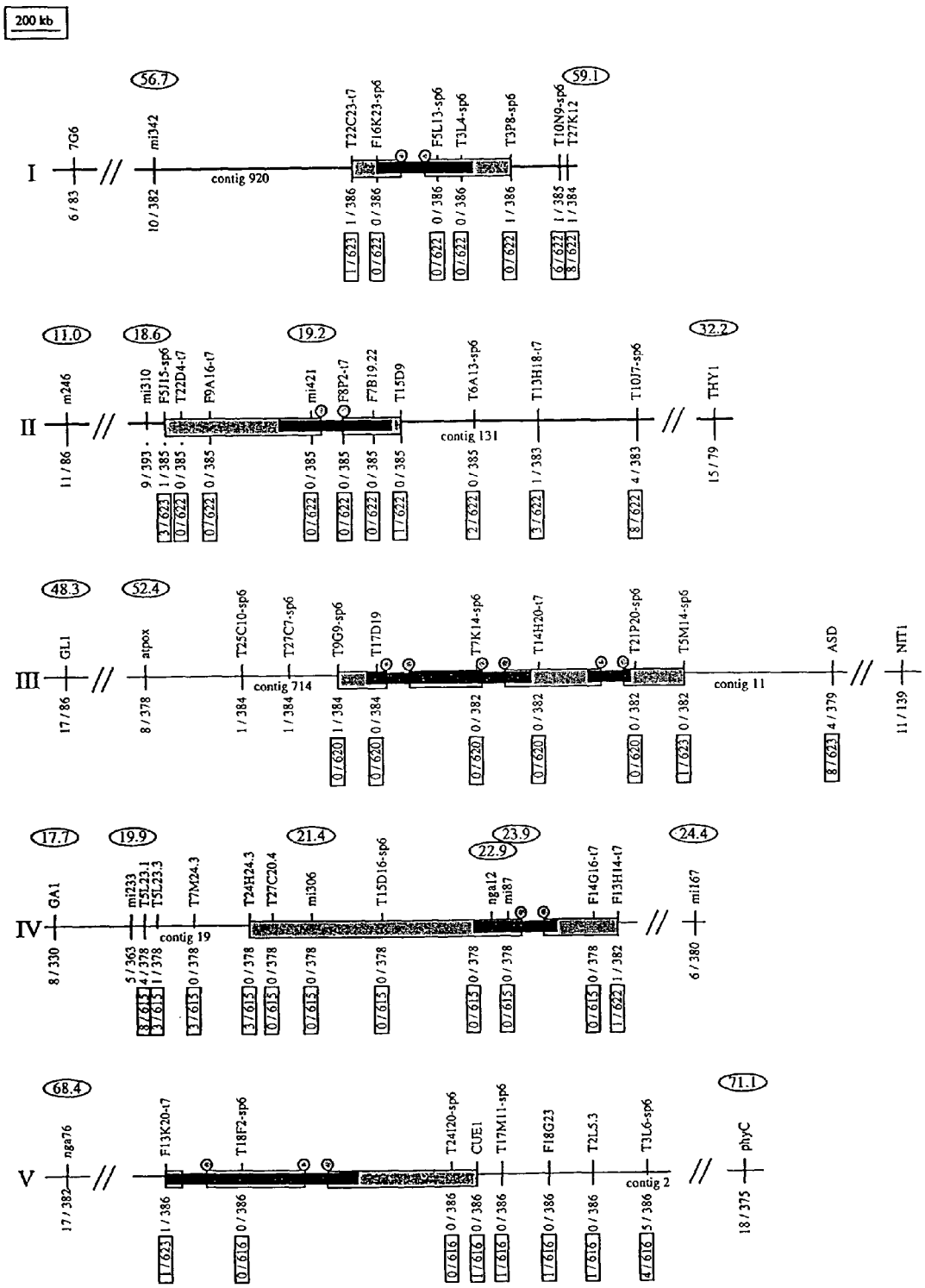

2695 BAC clones from the Columbia ecotype were identified in an initial study using hybridization of labeled methylated nucleic acid segments. An analysis was carried out to determine the relative proportion of centromere sequence containing clones within this collection. The BAC clones were identified based on their location on the filters. The detected clones were then compared to A. thaliana centromere-spanning contigs which had previously been assembled. The results of the analysis are given in FIG. 4B and FIG. 9). Over 41% of the clones were found to map to the Arabidopsis thaliana centromere. This constituted an estimated 20 fold enrichment for centromere DNA relative to a random clone. By comparison of signal obtained using methylated nucleic acids relative to signal with unmethylated nucleic acid probes (FIG. 8A, FIG. 8B, FIG. 9), and stringent selection of clones showing strong signal for methylated DNA but little or no signal for the unmethylated DNA, the yield of centromere-containing clones approached 100%.

Example 5

Automated Hybridization Signal Analysis

In addition to manual scoring of arrays, one or more optical visualization and or scoring systems may be employed with the invention. Such automated techniques may be more efficient than manual analyses and may facilitate comparisons of multiple layers of data, for example, from different hybridizations to an array. In particular, non-centromere DNA, such as unmethylated or repetitive DNA, could be separately detected on the array and those sectors of the array yielding signal subtracted from the positive "hits" yielded with the methylated probe DNA. In this way, background hits may be removed.

In one embodiment of the invention, automated analysis is carried out as follows. Filters are scanned on the PhosphorImager imaging Plate system (Molecular Dynamics, Sunnyvale, Calif.) for quantitative analysis of signal intensities. After image acquisition, the scanned 16-bit images are imported on a Sun workstation and image analysis is performed using the XdotsReader software (Cose, Le Bourget, France). The software processes the results of an exposure into images of individual filters and then translates the hybridization signal coordinates into dot localization on the filter using a reference grid for the arrangement of the dots. It takes into account slight variations in dot position attributable to filter deformation by assigning the signal detected to the nearest position expected. The software quantifies each dot individually after local background subtraction. These tasks, including image cutting, dot identification, and dot quantification are processed sequentially and automatically. The results are validated interactively, and a table is generated that contains for each dot its reference number and the experimental values.

Different types of values may be obtained for the quantification of the dot intensity: the radius of the dot, the mean of the dot pixel intensities for one dot, the maximal intensity of the pixels of the dot, the sum of the pixel intensities of the dot, and the average of the pixel intensities of the dot weighted by the distance to the center of the dot. By analyzing such intensities, signal from methylated centromere sequences may be distinguished from background signal, for example, from repetitive sequence located throughout the target genome. To take into account experimental variations in specific activity of the probe preparations or exposure time that might alter the signal intensity, the data obtained from different hybridizations may be normalized by dividing the signal intensity for each dot by the average of the intensities of all the dots present of the filter to get a normalized value.

Example 6

Constructing BAC Vectors for Testing Centromere Function

A BAC clone may be retrofitted with none, one or more telomeres and selectable markers together with the DNA elements necessary for *Agrobacterium* transformation. This method will provide a means to deliver any BAC clone into cells and to test it for centromere function.

Figure 5:
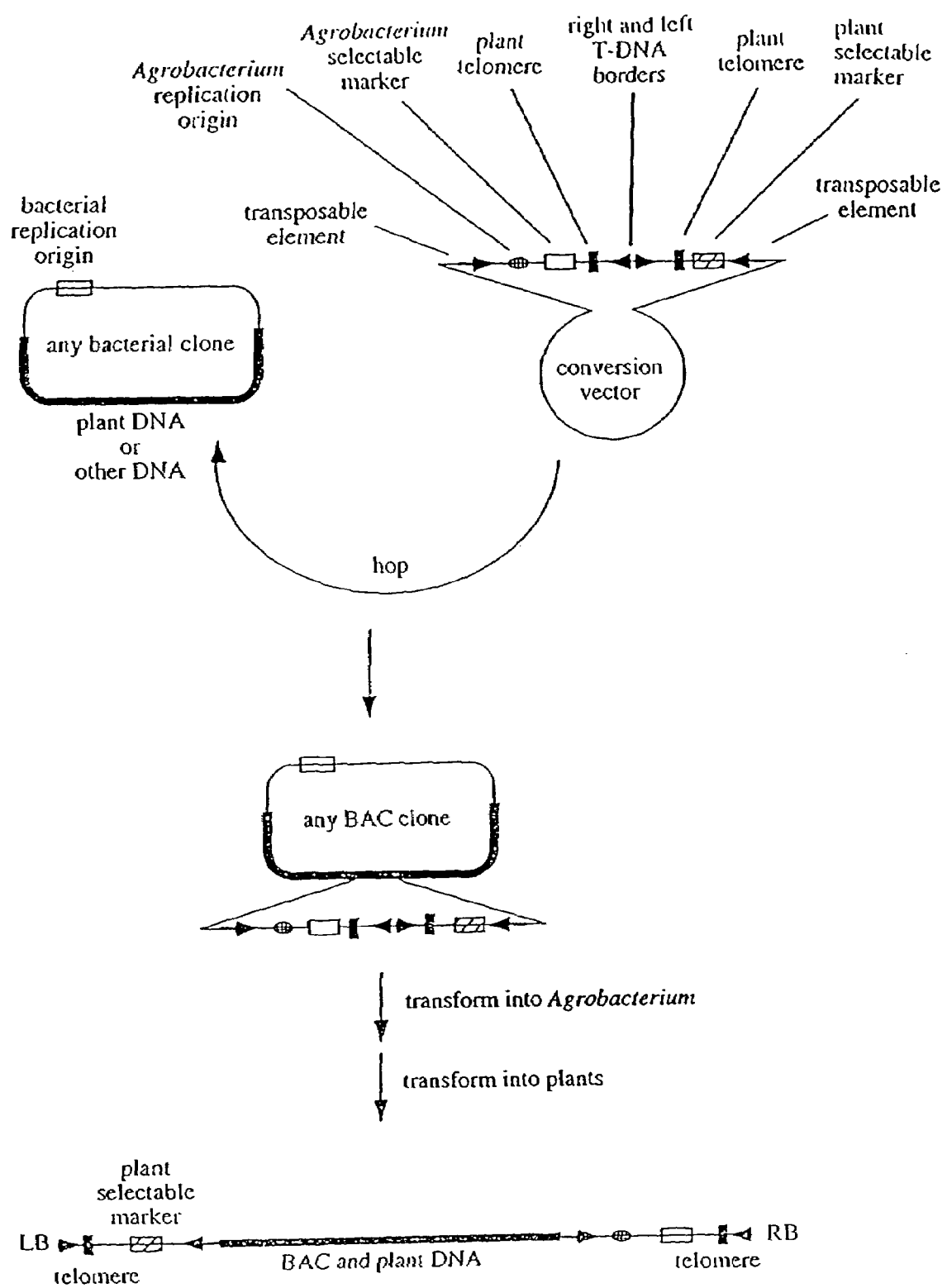
FIG. 5. Method for converting a BAC clone (or any other bacterial clone) into a minichromosome. A portion of the conversion vector will integrate into the BAC clone (or other bacterial clone of interest) either through non-homologous recombination (transposable element mediated) or by the action of a site specific recombinase system, such as Cre-Lox or FLP-FRT.

The method works in the following way. The conversion vector contains a retrofitting cassette. The retrofitting cassette is flanked by Tn10, Tn5, TO, Mu or other transposable elements and contains any combination of the following: an origin of replication and a selectable marker for *Agrobacterium*; a telomere series of repeats followed by T-DNA right and left borders followed by a second telomere series of repeats and a selectable marker (FIG. 5). The conversion vector is transformed into an *E. coli* strain carrying the target BAC. The transposable elements flanking the retrofitting cassette then mediates transposition of the cassette randomly into the BAC clone. The retrofitted BAC clone can now be transformed into an appropriate strain of *Agrobacterium* and then into cells, where it can be tested for meiotic and mitotic transmission which would indicate that the clone contained a functional centromere. Similarly any other method of transformation can be used.

Example 7

Methods for Assays

DNA analysis is performed as follows. Genomic DNA is isolated using a procedure modified from Shure et al. (1983). Approximately 1 gm tissue is ground to a fine powder in liquid nitrogen using a mortar and pestle. Powdered tissue is mixed thoroughly with 4 ml extraction buffer (7.0 M urea; 0.35 M NaCl; 0.05 M Tris-HCl, pH 8.0; 0.01 M EDTA, and 1% sarcosine). Tissue/buffer homogenate is extracted with 4 ml phenolchloroform. The aqueous phase is separated by centrifugation, passed through Miracloth, and precipitated twice using ⅒ volume of 4.4 M ammonium acetate (pH 5.2) and an equal volume of isopropanol. The precipitate is washed with 70% ethanol and resuspended in 200–500:1 TE (0.01 M Tris-Hcl and 0.001 M EDTA, pH 8.0).

The presence of a particular sequence in a target organism may be detected through the use of polymerase chain reaction (PCR). Using this technique, specific fragments of DNA can be amplified and detected following agarose gel electrophoresis. For example, two hundred to 1000 ng genomic DNA is added to a reaction mix containing 10 mM Tris-HCl (pH 8.3); 1.5 mM $Mgcl_2$; 50 mM KCl; 0.1 mg/ml gelatin; 200 µM each dATP, dCTP, dGTP, and dTTP; 0.5 µM each forward and reverse DNA primers; 20% glycerol; and 2.5 U Taq DNA polymerase. The reaction is run in a thermal cycling machine as follows with 39 repeats of the cycle: 94° C. for 3 min, 94° C. for 1 min, 50° C. for 1 min, and 72° C. for 30 s, followed by 72° C. for 5 min. Twenty µl of reaction mix is run on a 3.5% NuSieve gel in TBE buffer (90 mM Tris-borate and 2 mM EDTA) at 50V for two to four hours.

For Southern blot analysis, 20–40 µg genomic DNA is digested with 10–200 UNITS of restriction endonucleases, electrophoresed through 0.6%–1.0% agarose (Gibco BRL), and transferred (Southern, 1975) to Nytran (Schleicher and Schuell) using 10×SSC for 2 hr—overnight at 65° C. in a 50-ml solution containing final concentrations of 0.5 M $NaPO_4$ (phosphate buffer) pH 7.2, 7% SDS, 1% BSA, 1 mM EDTA, and 10 µg/ml salmon sperm DNA. Filters then are hybridized overnight at 65° C. in 6×SSC with $^{32}$P-labeled probe. Filters are washed once in 2×SSC and 0.1% SDS at 65° C. for 30 min and two times in 0.1 ×SSC, 1% SDS at 65° C. for 15 min and visualized by autoradiography using Kodak XAR5 film.

Example 8

Constructing BAC Vectors for Testing Centromere Function

A BAC clone may be retrofitted with one or more telomeres and selectable markers together with the DNA elements necessary for *Agrobacterium* transformation (FIG. 5). This method will provide a means to deliver any BAC clone into cells and to test it for centromere function.

The method works in the following way. The conversion vector contains a retrofitting cassette. The retrofitting cassette is flanked by Tn10, Tn5, TO, Mu or other transposable elements and contains an origin of replication and a selectable marker for *Agrobacterium*, a telomere series of repeats followed by T-DNA right and left borders followed by a second telomere series of repeats and a selectable marker (FIG. 5). The conversion vector is transformed into an *E. coli* strain carrying the target BAC. The transposable elements flanking the retrofitting cassette then mediate transposition of the cassette randomly into the BAC clone. The retrofitted BAC clone can now be transformed into an appropriate strain of *Agrobacterium* and then into cells where it can be tested for high fidelity meiotic and mitotic transmission which would indicate that the clone contained a complete functional centromere.

Example 9

Construction of Minichromosomes with Centromeres

Minichromosomes are constructed by combining the previously isolated essential chromosomal elements, including a centromere isolated in accordance herewith. Exemplary minichromosome vectors include those designed to be "shuttle vectors"; i.e., they can be maintained in a convenient host (such as *E. coli, Agrobacterium* or yeast) as well as plant or animal cells.

A. General Techniques for Minichromosome Construction

A minichromosome can be maintained in *E. coli* or other bacterial cells as a circular molecule by placing a removable stuffer fragment between the telomeric sequence blocks. The stuffer fragment is a dispensable DNA sequence, bordered by unique restriction sites, which can be removed by restriction digestion of the circular DNAs to create linear molecules with telomeric ends. The linear minichromosome can then be isolated by, for example, gel electrophoresis. Alternatively, if the stuffer fragment includes the border sequences for the *Agrobacterium* T-DNA, linearization will occur naturally during transformation. In addition to the stuffer fragment and the telomeres, the minichromosome contains a replication origin and selectable marker that can function in plants. Telomeres may or may not be included with the minichromosome. The minichromosomes also include a selectable marker, a centromere, and a ARS to allow replication and maintenance of the DNA molecules in cells. Finally, the minichromosome includes several unique restriction sites where additional DNA sequence inserts can be cloned. The most expeditious method of physically constructing such a minichromosome, i.e., ligating the various essential elements together for example, will be apparent to those of ordinary skill in this art.

B. Modified Technique for Minichromosome Construction

Figure 6A:
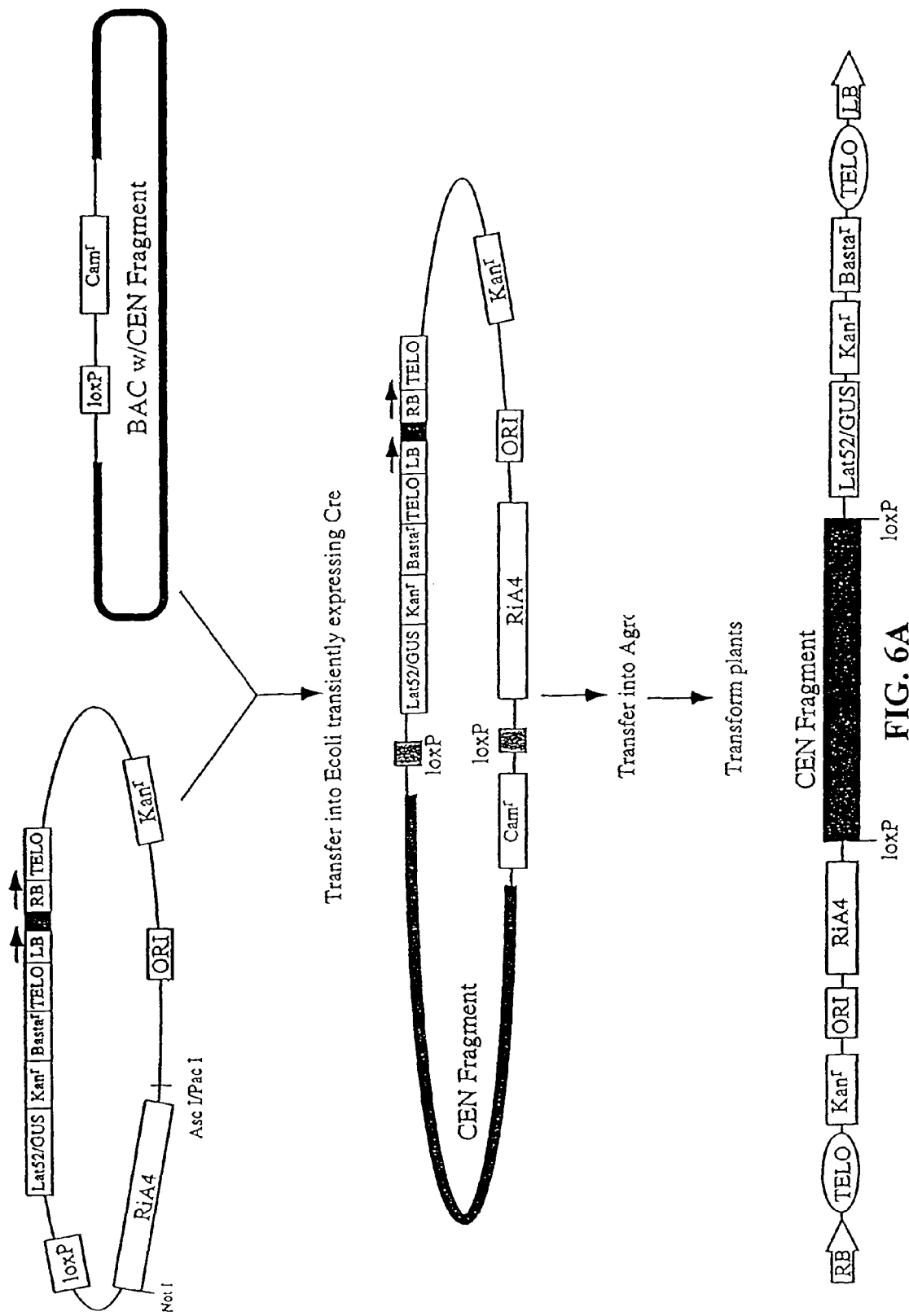
FIG. 6A-6G. Method for converting a BAC clone (or any other bacterial clone) into a minichromosome. The necessary selectable markers and origins of replication for propagation of genetic material in *E. coli, Agrobacterium* and *Arabidopsis* as well as the necessary genetic loci for *Agrobacterium* mediated transformation into *Arabidopsis* are cloned into a conversion vector. Using Cre/loxP recombination, the conversion vectors are recombined into BACs containing centromere fragments to form minichromosomes.

A two step method was developed for construction of minichromosomes, which allows adding essential elements to BAC clones containing centromeric DNA. These procedures can take place in vivo, eliminating problems of chromosome breakage that often happen in the test tube. The details and advantages of the techniques are as follows:

1.) One plasmid can be created that contains markers, origins and border sequences for *Agrobacterium* transfer, markers for selection and screening in the target organisms, telomeres, and a loxP site or other site useful for site-specific recombination in vivo or in vitro. The second plasmid can be an existing BAC clone, isolated from the available genomic libraries (FIG. 6A).

Figure 6B:
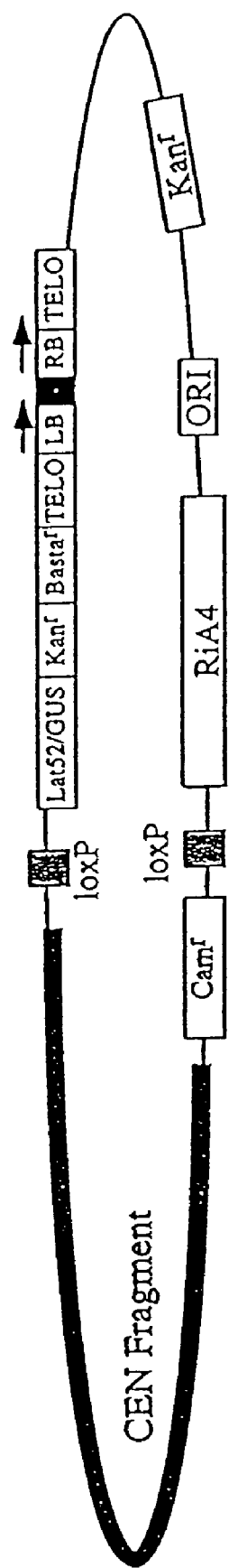

2.) The two plasmids are mixed, either within a single *E. coli* cell, or in a test tube, and the site-specific recombinase cre is introduced. This will cause the two plasmids to fuse at the loxP sites (FIG. 6B).

3.) If deemed necessary, useful restriction sites (AseI/PacI or Not I) are included to remove excess material (for example other selectable markers or replication origins).

Figure 6C:
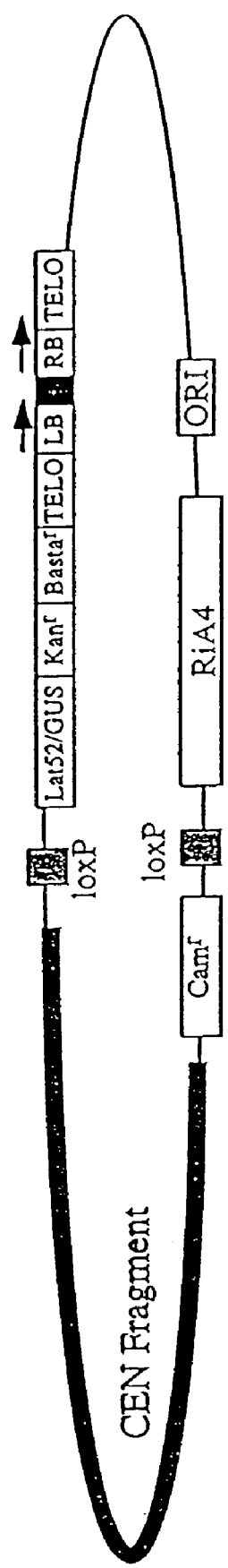
Figure 6D:
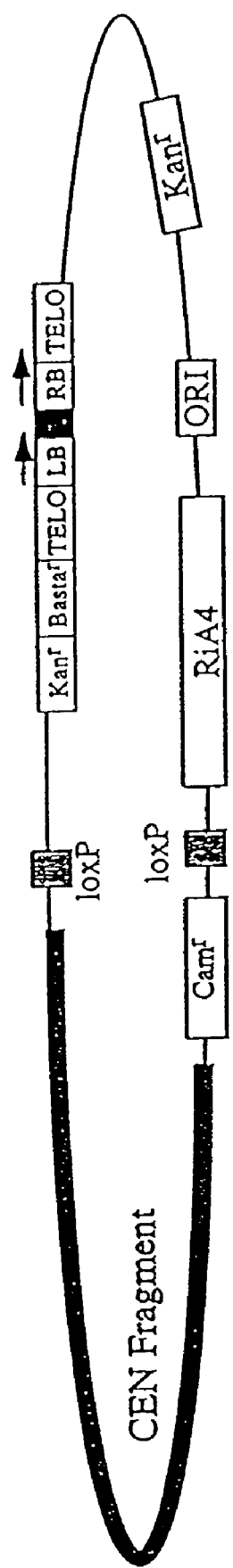
Figure 6E:
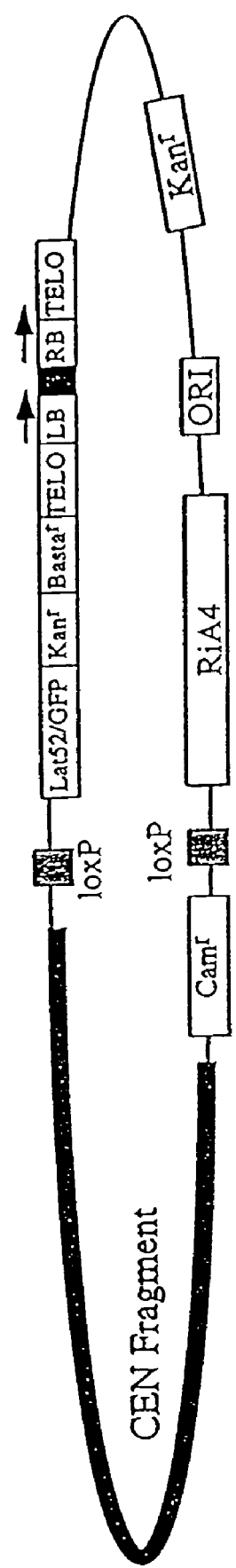

4.) Variations include vectors with or without a Kan$^R$ gene (FIGS. 6B, 6C, with or without a LAT52 GUS gene, with a LAT52 GFP gene, and with a GUS gene under the control of other promoters (FIGS. 6C, 6D and 6E) and with or without telomeres.

C. Method for Preparation of Stable Non-Integrated Minichromosomes

Figure 6F:
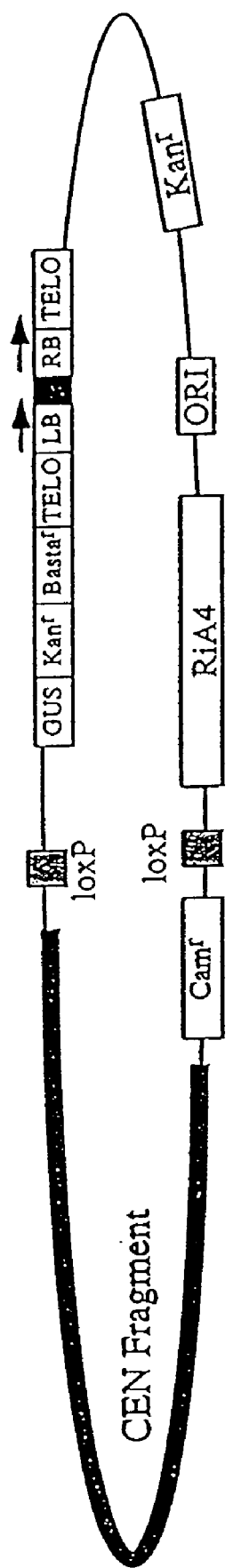
Figure 6G:
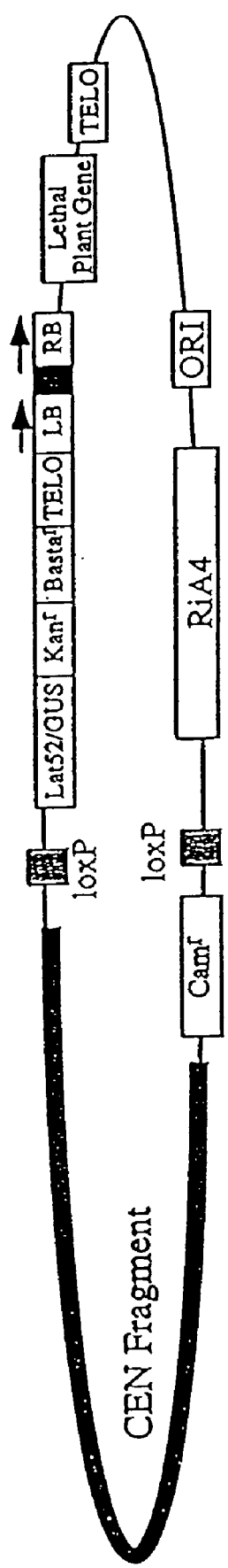

A technique has been developed to ensure that minichromosomes do no integrate into the host genome (FIG. 6F). In particular, minichromosomes must be maintained as distinct elements separate from the host chromosomes. To ensure that the introduced minichromosome does not integrate, the inventors envision a variety that would encode a lethal gene (such as diptheria toxin or any other gene product that, when expressed, causes lethality). This gene could be located between the right *Agrobacterium* border and the telomere. Minichromosomes that enter a nucleus and integrate in host chromosome would result in lethality. However, if the minichromosome remains separate, and further, if the ends of this construct are degraded up to the telomeres, then the lethal gene would be removed and the cells would survive.

Example 10

In Vivo Screening of Centromere Activity by the Analysis of Dicentric Chromosomes Centromeres isolated in accordance with the invention may be assayed in vivo (FIG. 7). In the method, cells are first transformed with binary BAC clones that contain DNA from the candidate centromere sequences. By allowing the DNA to integrate into the host chromosomes, it is expected that this integration will result in a chromosome with two centromeres, This is an unstable situation which often leads to chromosome breakage, as single chromosomes harboring two or more functional centromeres will often times break at junctions between the two centromeres when pulled towards opposite poles during mitotic and meiotic events. This can lead to severe growth defects and inviable progeny when genes important or essentially for cellular and developmental processes are disrupted by the breakage event. Therefore, regions having centromere function could be identified by looking for clones that exhibit, upon introduction into a host plant, any of the following predicted properties: reduced efficiencies of transformation; causation of genetic instability when integrated into natural chromosomes such that the transformed organisms show aberrant sectors and increased lethality; a difficulty to maintain, particularly when the transformed plants are grown under conditions that do not select for maintenance of the transgenes; a tendency to integrate into the genome at the distal tips of chromosomes or at the centromeric regions. In contrast, clones comprising non-centromeric DNA will be expected to integrate in a more random pattern. Confirmation of a resulting distribution and pattern of integration can be determined by sequencing the ends of the inserted DNA.

The screen is performed by identifying clones of greater than 100 kb that encode centromere DNA in a BiBAC library (binary bacterial artificial chromosomes) (Hamilton, 1997). This is done by screening filters comprising a BiBAC genomic library for clones that encode DNA from the centromeres (FIG. 7, step 1). The BiBAC vector is used because it can contain large inserts of *Arabidopsis* genomic material and also encodes the binary sequences needed for *Agrobacterium*-mediated transformation. The centromere sequence containing BiBAC vectors are then directly integrated into chromosomes by *Agrobacterium*-mediated transformation (FIG. 7, step 2). As a control, BiBAC constructs containing non-centromeric DNA also are used for transformation. BiBACs harboring sequences with centromere function will result in forming dicentric chromosomes. Progeny from transformed organisms will be analyzed for nonviability and gross morphological differences that can be attributed to chromosomal breaks due to the formation of dicentric chromosomes (FIG. 7, step 3). Non-centromere sequences are expected to show little phenotypic differences from wildtype individuals. As an alternative to the above-described technique. BACs identified by another means may be converted to BiBACs as described in Example 8.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural and other details supplementary to those set forth herein, are specifically incorporated he 5 by reference.

Abdullah et al., *Biotechnology*, 4: 1087, 1986.
Ahmad, K. and S. Henikoff, *J. Cell Biol.*, 153, 101 (2001).
Alfenito et al., "Molecular characterization of a maize B chromosome centric sequence," *Genetics*, 135:589–597, 1993.
Bell and Ecker, "Assignment of 30 microsatellite loci to the linkage map of *Arabidopsis*," *Genomics*, 19:137–144, 1994.
Bellus, *J Macromol. Sci. Pure Appl. Chem*, A31(1): 1355–1376 (1994).
Bender, J., *Trends Biochem Sci* 23, 252 (1998).
Bevan et al., *Nucleic Acids Research*, 11(2):369–385, 1983.
Bloom, "The centromere frontier: Kinetochore components, microtubule-based motility, and the CEN-value paradox," *Cell*, 73:621–624, 1993.
Broach et al., *Gene*, 8:121–133, 1979.
Burke et al., *Science*, 23 6:806–812, 1987.
Butkus, V., Petrauskiene, L., Maneliene, Z., Klimasauskas, S., Laucys, V. and Janulaitis, A. "Cleavage of methylated CCCGGG sequences containing either N4methylcytosine or 5-methylcytosine with MspI, HpaII, SmaI and Cfr9I restriction endonucleases." *Nucl. Acids Res* 15, 7091–7102, 1987.
Bytebier et al., *Proc. Natl Acad Sci.* USA, 84:5345, 1987.
Callis et al., *Genes and Development*, 1: 1183, 1987.
Campbell, "Monoclonal Antibody Technology, Laboratory Techniques in Biochemistry and Molecular Biology," Vol. 13, Burden and Von Knippenberg, Eds. pp. 75–83, Elsevier, Amsterdam, 1984.
Cao, X. et al., Proc Natl Acad Sci USA 97, 4979 (2000).
Capecchi, "High efficiency transformation by direct microinjection of DNA into cultured mammalian cells," *Cell* 22(2):479–488, 1980.
Chandler et al., *The Plant Cell*, 1: 1175–1183, 1989.
Choi S., Creelman R A, Mullet J E, Wing R A: Construction and characterization of a bacterial' artificial chromosome library of *Arabidopsis thaliana*." *Plant Mol. Biol*. Rep. 13: 124–129 (1995).
Choo, K. H., *Trends Cell Biol* 10, 182 (2000).
Chu et al., "Separation of large DNA molecules by contour-clamped homogeneous electric fields" *Science*, 234, 1582–1585, 1985.
Clapp, "Somatic gene therapy into hematopoietic cells. Current-status and future implications," *Clin. Perinatol.* 20(1):155–168, 1993.
Cohen et al., *Proc. Nat'l Acad. Sci. USA*, 70:3 240, 1973,
Conkling et al., *Plant Physiol.*, 93:1203–1211, 1990.
Copenhaver and Pikaard, "RFLP and physical mapping with an rDNA-specific endonuclease reveals that nucleolus organizer regions of *Arabidopsis thaliana* adjoin the telomeres on chromosomes 2 and 4, "*Plant J, 9*:259–276, 1996.
Copenhaver and Preuss, *Plant Biology*, 2:104–108, 1999
Copenhaver et al., "Use of RFLPs larger than 100 kbp to map position and internal organization of the nucleolus organizer region on chromosome 2 in *Arabidopsis thaliana*," *Plant J.* 7, 273–286, 1995.
Copenhaver et al., *Science*. 286:2468–2474, 1999.
Copenhaver, G. P., and Pikaard, C. S. "Two-dimensional RFLP analyses reveal megabase sized clusters of rRNA gene variants in *Arabidopsis thaliana*, suggesting local spreading of variants as the mode for gene homogenization during concerted evolution." *Plant J.* 9, 273–282, 1996.
Cristou et al., *Plant Physiol*, 87:671–674, 1988.
Curiel et al., "Adenovirus enhancement of transferrin-polylysine-mediated gene delivery," *Proc. Nat'l Acad. Sci. USA* 88(19):8850–8854, 199L
Curiel et al., high-efficiency gene transfer mediated by adenovirus coupled to DNA-polylysine complexes," *Hum. Gen. Ther.* 3(2):147–154, 1992.
Dedon P C, Soults J A, Allis C D, Gorovsky M A, "A simplified formaldehyde fixation and immunoprecipitation technique for studying protein-DNA interactions." *Anal. Biochem* 197(1): 83–90, 1991
Dellaporta et al., In: *Chromosome Structure and Function: Impact of New Concepts*, 18th Stadler Genetics Symposium, 11:263–282, 1988.
Depicker et al., *Plant Cell Reports*, 7:63–66, 1988.
DiLaurenzio et al., *Cell*, 86:423–33, 1996
Donahue et al., "The nucleotide sequence of the HIS4 region of yeast," *Gene Apr;* 18(1):47–59, 1982.
Earnshaw, "When is a centromere not a kinetochore?," *J Cell Sci.*, 99:1–4, 1991.
Ebert et al., 84:5745–5749, *Proc. Nat'l Acad. Sci.* USA, 1987
Eglitis et al., "Retroviral vectors for introduction of genes into mammalian cells," *Biolechniques* 6(7):608–614, 1988.
Eglitis et al., "Retroviral-mediated gene transfer into hemopoietic cells," *Avd. Exp. Med.*
Ferrin et al., "Selective cleavage of human DNA: RecA-Assited Restriction Endonuclease (RARE) cleavage," *Science*, 254:1494–1497, 1991.
Finnegan, E. J. and E. S. Dennis, *Nucleic Acids Res.* 21, 2383 (1993).
Fraley et al., *Biotechnology*, 3:629, 1985.

Fransz, P. F. et al., *Cell* 100, 367 (2000).

Frohman, In: *PCR PROTOCOLS: A GUIDE TO METHODS AND APPLICATIONS*, Academic Press, N.Y., 1990.

Fromm et al., "Expression of genes transferred into monocot and dicot plant cells by electroporation," *Proc. Nat'l Acad. Sci. USA* 82(17):5824–5828, 1985.

Fromm et al., *Nature,* 312:791–793, 1986.

Frommer, M. et al., *Proc Natl Acad Sci*, USA 89, 1827 (1992).

Fujimura et al., *Plant Tissue Culture Letters,* 2:74, 1985.

Fynan et al., "DNA vaccines: protective immunizations by parenteral, mucosal, and gene gun inoculations," *Proc. Nat'l Acad. Sci. USA* 90(24):11478–11482, 1993.

Gefter et al., *Somatic Cell Genet.* 3:231–236, 1977.

Goding, "Monoclonal Antibodies: Principles and Practice," pp. 60–74. 2nd Edition, Academic Press, Orlando, Fla., 1986.

Graham et al., "Transformation of rat cells by DNA of human adenovirus 5," *Virology* 54(2):536–539, 1973.

Gruenbaum, Y. R, Stein, H. Cedar, A. Razin, *FEBS Lett* 124, 67 (1981).

Hamilton et al., "Stable transfer of intact high molecular weight DNA into plant chromosomes," *Proc Nat'l Acad Sci USA* 93(18):9975–9, 1996

Hamilton, "A binary-BAC system for plant transformation with high-molecular-weight DNA," *Gene,* 4;200(1–2):107–16,1997.

Hamilton, C M, Frary A, Xu Y, Tanksley S D, Zhang H-B: Construction of tomato genomic DNA libraries in a binary-BAC (BIBAC) vector. *Plant J* 18:223–229 (1999).

Hansen, R. S. et al., *Proc Natl Acad Sci USA* 96, 14412 (1999).

Haseloff et al., *Proc. Nat'l Acad. Sci. USA* 94(6):2122–2127, 1997.

Hinchee et al., *Bio/technol.,* 6:915–922, 1988.

Hudspeth and Grula, *Plant Mol. Biol.,* 12:579–589, 1989.

Ikuta et al., *Bio/technol.,* 8:241–242, 1990.

Innis et al., "DNA sequencing—with *Thermus aquaticus* DNA polymerase and direct sequencing of polymerase chain reaction-amplified DNA," *Proc Nat'l Acad Sci*

Jacobsen, S. E. and E. M. Meyerowitz, *Science* 277, 1100 (1997).

Jeddeloh, J A and Richards, E J, "$^m$CCG Methylation in Angiosperms," *The Plant Journal,* 9(5): 579–586, 1996.

Johnston et al., "Gene gun transfection of animal cells and genetic immunization," *Methods Cell. Biol.* 43(A):353–365, 1994.

Jones, P. L. and A. P. Wolffe, *Semin Cancer Biol* 9, 339 (1999).

Jorgensen et al., *Mol. Gen. Genet.,* 207:471, 1987.

Jouanin et al., *Mol Gene Genet,* 201:370–4, 1985

Katz et al., *J Gen. Microbiol.,* 129:2703–2714, 1983.

Klee et al., *Bio/Technology* 3:637–642, 1985.

Klein et al., *Nature,* 327:70–73, 1987.

Klein et al., *Proc. Nat'l Acad. Sci. USA,* 85:8502–8505, 1988.

Kohler et al., *Eur. J Immunol.* 6:511–519, 1976.

Kohler et al., *Nature* 256:495–497, 1975.

Konieczny et al., "A procedure for mapping *Arabidopsis* mutations using codominant ecotype-specific PCR-based markers," *The Plant Journal,* 4:403–410, 1993.

Koorneef et al., *Genetica,* 61:41–46, 1983.

Koorneef, "The use of telotrisomics for centromere mapping in *Arabidopsis thaliana* (L.) Heynh, *Genetica,* 62:33–40, 1983.

Kuo, M. H. and Allis, C. D., "Roles of histone acetyltransferases and deacetylases in gene regulation." *Bioessays* 20:615–626, 1998.

Kwoh et al. "Transcription-based amplification system and detection of amplified human immunodeficiency virus type I with a bead-based sandwich hybridization format, *Proc Nat'l Acad Sci USA.* 86(4):1173–1177,1989.

Lawton et al., *Plant Mol. Biol.* 9:315–324, 1987.

Lechner et al., "A 240 kd multisubunit protein complex, CBF3 is a major component of the budding yeast centromere," *Cell,* 64:717–725, 1991.

Lin, X. et al., *Nature* 402, 761 (1999).

Lindroth, A. M. et al., *Science* 292, in press (2001).

Liu, Y G., Shirano, Y., Fukaki, H., Yanai, Y., Tasaka, M., Tabata, S., Shibata, D, *Proc. Nat'l Acad Sci USA* 96:6535–40, 1999.

Lorz et al., *Mol. Gen. Genet.,* 199:178, 1985.

Louis, E J, "Corrected sequence for the right telomere of *Saccharomyces cerevisiae* chromosome III," *Yeast,* 10(2): 271–4, 1994.

Lu et al. "High efficiency retroviral mediated gene transduction into single isolated immature and replatable CD34(3+) hematopoietic stem/progenitor cells from human umbilical cord blood," *J Exp. Med.* 178(6):2089–2096, 1993.

Luff, B., L. Pawlowski, J. Bender, *Mol Cell* 3, 505 (1999).

Maluszynska, J. and Heslop-Harrison, J. S. 1991 "Localization of tandemly repeated DNA sequences in *Arabidopsis thaliana.*" *Plant J* 1: 159–66.

Maniatis et al., "Molecular Cloning: a Laboratory Manual," Cold Spring Harbor Laboratory, Cold Spring Harbor, N.Y., 1982.

Marcotte et al., *Nature,* 335:454, 1988.

Marra et al., *Mature Genet.* 22:265, 1999.

Martinez-Zapater, J. M., Estelle, M. A. and Somerville, C. R. 1986 "A highly repeated DNA sequence in *Arabidopsis thaliana.*" *Mol. Gen. Genet.* 204: 417–23

McCabe et al., *Biotechnology,* 6:923, 1988.

McClelland, M., Nelson, M. and Raschke, E. "Effect of site-specific modification on restriction endonuclease and DNA modification methyltransferases." *Nucl. Acids Res.* 22,3640–3659, 1994.

Meksem K, Ruben E. Zobrist K, Hyten D, Tao Q, Zhang H-B, Lightfoot A D: "Two plant transformation-ready bacterial artificial chromosome libraries for soybean: Application in chromosome walking and genome-wide physical mapping." *Theor. Appl. Genet* 99:1131–1142 (1999).

Mortimer et al., "Genetic mapping in *Saccharomyces cerevisiae,*" Life Cycle and Inheritance, In: *The Molecular Biology of the Yeast Saccharomyces,* 11–26, 1981.

Moullet O, Zhang H-B, Lagudah E S: Construction and characterization of a large DNA insert library from the D genome of wheat. Theor Appl Genet 1999, 99: 305–313.

Mozo et al., *Mol Getz Genet,* 258:562–70, 1998

Mozo et al., *Nature Genet.* 22:271, 1999.

Murakami et al., *Mol. Gen. Genet.,* 205:42–50, 1986.

Mysore et al., "An arabidopsis histone 142A mutant is deficient in agrobacterium T-DNA integration," *Proc Nat'l Acad Sci USA* 18;97(2):948–53, 2000a.

Mysore et al., "*Arabidopsis* ecotypes and mutants that are recalcitrant to *Agrobacterium* root transformation are susceptible to germ-line transformation. *Plant J* 21(1): 916, 2000b.

Nagane, Y., K. Utsugisawa, H. Tohgi, *Brain Res Brain Res Protoc* 5, 167 (2000).

Negrutiu, I., Hinnisdaels, S., Cammaerts, D., Cherdshewasart, W., Gharti-Chhetfi, G., and Jacobs, M. "Plant protoplasts as genetic tool: selectable markers for developmental studies," *Int. J Dev. Biol.* 36: 73–84, 1992.

Ng, H and Bird, A, "DNA methylation and chromation modification" *Current Opinion in Genetics & Development, pp* 158–163, 1999.

Nicklas, "The forces that move chromosomes in mitosis," *Annu. Rev. Biophys. Biophys. Chem.,* 17:431–39, 1988.

Nussbaum et al., *Proc. Nat'l Acad. Sci USA,* 73:1068, 1976.

Odell et al., Nature, 313:810–812, 1985.

Ohara et al., "One-sided polymerase chain reaction: the amplification of cDN&"

Ohmori and Tomizawa, "Nucleotide sequence of the region required for maintenance of colicin E I plasmid," *Mol Gen Genet*, October 3—176(2):161–70, 1979.

Omirulleh et al., *Plant Molecular Biology,* 21:415–428, 1993.

Ow et al., Science, 234:856–859, 1986.

Potrykus et al., *Mol. Gen. Genet.,* 199:183–188, 1985.

Prasher et al., *Biochem. Biophys. Res. Commun.,* 126(3): 1259–1268, 1985.

Preuss et al., "Tetrad analysis possible in *Arabidopsis* with mutation of the QUARTET (QRT) genes," *Science,* 264: 1458, 1994.

Rathore et al., *Plant Mol Biol,* 21:871–84, 1993

Rattner, "The structure of the mammalian centromere," *Bioassays,* 13(2):51–56, 1991

Reichel et al., *Proc. Nat'l Acad. Sci. USA,* 93 (12) p. 5888–5893. 1996

Richards and Ausubel, "Isolation of a higher eukaryotic telomere from *Arabidopsis thaliana,*" *Cell,* 8:53(1):127–36, 1988.

Richards et al., "The centromere region of *Arabidopsis thaliana* chromosome 1 contains telomere-similar sequences," *Nucleic Acids Research,* 19(12):3351–3357, 1991.

Robertson, K. D. and P. A. Jones, *Carcinogenesis* 21, 461 (2000).

Rogers et al., *Meth. in Enzymol.,* 153:253–277, 1987.

Round, E. K., Flowers, S. K., and Richards, E. J. "*Arabidopsis thaliana* centromere regions: genetic map positions and repetitive DNA structure." Genome Res. 7 1045–1053, 1997.

Sambrook et al., In: *Molecular Cloning: A Laboratory Manual*, Vol. 1, Cold Spring Harbor Laboratory Press, Cold Spring Harbor, N.Y., Ch. 7,7.19–17.29, 1989.

Schwartz et al., Cold Spring Harbor Symp. *Quant. Biol.,* 47, 195–198, 1982.

Sheen et al., *Plant Journal,* 8(5):777–784, 1995.

Shure et al., *Cell,* 3 5:225–23 3 (1983).

Singer, T., C. Yordan, R. A. Martienssen, *Genes Dev* 15, 591 (2001).

Smythe, "Pollen clusters," *Current Biology,* 4:851–853, 1994.

Somerville, C. and Somerville, S., *Science* 285:380, 1999.

Spielmann et al., Mol. Gen. Genet., 205:34, 1986.

Stalker et al., *Science,* 242:419–422, 1988.

Stougaard, *The Plant Journal,* 3:755–761, 1993.

Streeck, R. E., *Gene* 12, 267 (1980).

Sullivan, Christensen, Quail, *Mol. Gen. Genet.,* 215(3): 431–440, 1989

Sutcliffe, *Proc. Nat'l Acad. Sci. USA,* 75:3737–3741, 1978.

The *Arabidopsis* Genome Initiative, Nature 408, 796 (2000).

Thillet et al., *J Biol. Chem.,* 263:12500–12508, 1988.

Thomas et al., *Proc. Nat'l Acad. Sci. USA,* 71:4579, 1974.

Tian, Sequin, Charest, *Plant Cell Rep.,* 16:267–271, 1997.

Toriyama et al., *Theor Appl. Genet.,* 73:16, 1986.

Twell et al., *Genes Dev* 5:496–507, 1991

Twell et al., *Plant Physiol* 91:1270–1274, 1989.

Tyler-Smith et al., "Mammalian chromosome structure," *Current Biology,* 3:390–397, 1993.

Uchimiya et al., *Mol. Getz. Genet.,* 204:204, 1986.

USA. 85(24):9436–9440, 1988.

Van't Hof, Kuniyuki, Bjerkens, "The size and number of replicon families of chromosomal DNA of *Arabidopsis thaliana,*" *Chromosoma,* 68: 269–285, 1978.

Vasil et al., "Herbicide-resistant fertile transgenic wheat plants obtained by microprojectile bombardment of regenerable embryogenic callus," *Biotechnology,* 10:667–674, 1992.

Vasil, *Biotechnology,* 6:397, 1988.

Vinatzer B A, Zhang H-B, Sanasavini S: Construction and characterization of a BAC library of apple (*Malus* x *domestica* Borkh.) Theor. Appl. Genet. 97: 1183–1190 (1998).

Vongs, A., Kakutani, T., Martienssen, R. A. and Richards, E. J. 1993 "*Arabidopsis thaliana* DNA Methylation Mutants." *Science* 260:1926–28

Wagner et al., "Coupling of adenovirus to transferrin-polylysine/DNA complexes greatly enhances receptor-mediated gene delivery and expression of transfected genes," *Proc. Nat'l Acad. Sci. USA* 89 (13):6099–6103, 1992, Walker et al., "Strand displacement amplification—an isothermal, in vitro DNA amplification technique," *Nucleic Acids Res.* 20(7): 1691–1696, 1992

Walker et al., *Proc. Nat'l Acad. Sci. USA,* 84:6624–6628, 1987.

Wang et al., *Molecular and Cellular Biology,* 12(8):3399–3406, 1992.

Willard, H. F., *Proc. Natl. Acad. Sci.* USA, 98, 5374 (2001).

Willard, H., *Nature Genetics* 15:345–354, 1997

Willard, H., "Centromeres of mammalian chromosomes" *Trends Genet.,* 6:410–416, 1990.

Wong et al., "Electric field mediated gene transfer," *Biochim. Biophys. Res. Commun.* 107(2):584–587, 1982.

Woo, J Jiang, B S Gill, A H Paterson, and R A Wing, Construction and characterization of a bacterial artificial chromosome library of Sorghum bicolor, Nucl. Acids. Res. (1994) 22: 4922–4931.

Woodcock, D. M., C. B. Lawler, M. E. Linsenmeyer, J. P. Doherty, W. D. Warren, *J. Biol. Chem.* 272, 7810 (1997).

Yamada et al., *Plant Cell Rep.,* 4:85, 1986,

Yang and Russell, *Proc. Nat'l Acad. Sci. USA,* 87:4144–4148, 1990.

Yoder, J. A., C. P. Walsh, T. H. Bestor, *Trends Genet* 13, 335 (1997).

Young et al., In: *Eukaryotic Genetic Systems ICN-UCLA Symposia on Molecular and Cellular Biology,* VII, 315–331, 1977.

Zhou, Y., C. W. Magill, J. M. Magill, R. J. Newton, *Genome* 41, 23 (1998).

Zukowskyetal., *Proc. Nat'l Acad. Sci. USA,* 80:1101–1105, 1983.

Zwick, M. S., et al. "A rapid procedure for the isolation of $C_0t$-1 DNA from plants" Genome 40(1) 138–142 (1997).

What is claimed is:

1. A method of obtaining a centromere nucleic acid sequence from a selected organism comprising the steps of:
   a) preparing a first sample of genomic DNA from a selected organism;
   b) contacting said genomic DNA with a strand-specific methylation sensitive restriction endonuclease;
   c) nick-translating the genomic DNA to form nick-translated products;
   d) hybridizing the nick-translated products from step (c) to candidate centromere nucleic acids, and
   e) detecting a centromere nucleic acid sequence that hybridizes to the nick-translated genomic DNA.

2. The method of claim 1, wherein the strand-specific methylation sensitive restriction endonuclease is selected from the group consisting of HpaI, KpnI, MaeII, or Sau3A I.

3. The method of claim 1, wherein detecting comprises screening an array.

4. The method of claim 3, wherein said screening comprises the steps of
   a) obtaining an array comprising cloned genomic DNA from said selected organism; and
   b) detecting a centromere nucleic acid sequence from said cloned genomic DNA of said array by hybridizing the nick translated genomic DNA to said array.

5. The method of claim 4, wherein a plurality of centromere nucleic acid sequences are detected from said array.

6. The method of claim 4, wherein said array comprises said cloned genomic DNA attached to a solid support.

7. The method of claim 6, wherein said array is further defined as comprising cloned genomic DNA attached to said solid support in a selected pattern.

8. The method of claim 7, wherein said selected pattern comprises a grid.

9. The method of claim 6, wherein said cloned genomic DNA comprises DNA cloned in a bacterial artificial chromosome.

10. The method of claim 6, wherein said cloned genomic DNA comprises DNA cloned in a yeast artificial chromosome.

11. The method of claim 6, wherein the solid support comprises a microscope slide.

12. The method of claim 6, wherein said solid support comprises a hybridization filter.

13. The method of claim 4, wherein said array comprises a plurality of DNA pools, said pools comprising the nucleic acid sequences of at least a first and a second clone comprising genonmic DNA from said selected organism.

14. The mcmhod of claim 1, wherein said contacting is further dclined as comprising:
   a) obtaining a second sample of genomic DNA from said selected organism;
   b) contacting said second sample of genomic DNA with an isoschizomer of said strand-specific methylation sensitive restriction endonuclease, wherein said isoschizomer is not a strand-specific methylation sensitive restriction endonuclease;
   c) resolving separately said first and said second samples of genomic DNA following said contacting; and d) selecting a plurality of hemimethylated nucleic acid segments from at least a first nucleic acid fraction present in said first sample of genomic DNA and not present in said second sample of genomic DNA.

15. The method of claim 1, wherein said nick-translating comprises radioactively labeling the genomic DNA.

16. The method of claim 1, wherein said nick-translating comprises labeling the genomic DNA with an antigen.

17. The method of claim 1, wherein said nick-translating comprises labeling the genomic DNA with a fluorophore.

18. The method of claim 1, wherein said selected organism is a plant.

19. The method of claim 18, wherein said plant is a dicotyledonous plant.

20. The method of claim 19, wherein said dicotyledonous plant is selected from the group consisting of tobacco, tomato, potato, sugar beet, pea, carrot, cauliflower, broccoli, soybean, canola, sunflower, alfalfa, cotton and *Arabidopsis*.

21. The method of claim 20, wherein said dicotyledonous plant is *Arabidopsis thaliana*.

22. The method of claim 18, wherein said plant is a monocotyledonous plant.

23. The method of claim 22, wherein said monocotyledonous plant is selected from the group consisting of wheat, maize, rye, rice, turfgrass, oat, barley, sorghum, millet, and sugarcane.

24. The method of claim 23, wherein said monocotyledonous plant is maize.

25. The method of claim 1, wherein said selected organism is a mammal.

26. The method of claim 1, wherein said selected organism is a human.

27. The method of claim 1, further defined as comprising fluorescent in situ hybridization of the centromere nucleic acid sequence.

28. The method of claim 1, further defined as comprising determining the nucleic acid sequence of the centromere nucleic acid sequence.

29. The method of claim 28, further defined as comprising comparing the nucleic acid sequence of the centromere nucleic acid sequence to a known centromere sequence.

30. The method of claim 1, further defined as comprising transforming a cell with the centromere nucleic acid sequence.

31. The method of claim 30, wherein said cell is further defined as integratively transformed with said centromere nucleic acid sequence.

32. The method of claim 30, wherein said cell is further defined as non-integratively transformed with said centromere nucleic acid sequence.

33. The method of claim 31, further comprising screening for a phenotypic effect present in the integratively transformed cells or an organism comprising the cells, wherein said phenotypic effect is absent in a control cell not integratively transformed with said centromere nucleic acid sequence or an organism comprising said control cell.

34. The method of claim 33, wherein said phenotypic effect is selected from the group consisting of reduced viability, reduced efficiency of said transforming, genetic instability in the integratively transformed nucleic acid, aberrant tissue sectors, increased ploidy, ancuploidy, and increased integrative transformation in distal or centromeric chromosome regions.

35. The method of claim 30, wherein said centromere nucleic acid sequence is further defined as comprising a recombinant construct.

36. The method of claim 30, wherein said centromere nucleic acid sequence is further defined as comprising cloned DNA.

37. The method of claim 36, wherein the cloned DNA is not methylated.

38. The method of claim 36, wherein the cloned DNA is remethylated prior to said transforming.

39. The method of claim 38, wherein the remethylated DNA is hemimethylated.

40. The method of claim 35, wherein said recombinant construct comprises a telomere.

41. The method of clam 35, wherein said recombinant construct comprises an autonomous replicating sequence (ARS).

42. The method of claim 35, wherein said recombinant construct comprises a structural gene.

43. The method of claim 42, wherein said structural gene comprises a selectable or screenable marker gene.

* * * * *

UNITED STATES PATENT AND TRADEMARK OFFICE
CERTIFICATE OF CORRECTION

PATENT NO. : 7,132,240 B2 Page 1 of 1
APPLICATION NO. : 10/620924
DATED : November 7, 2006
INVENTOR(S) : Song Luo et al.

It is certified that error appears in the above-identified patent and that said Letters Patent is hereby corrected as shown below:

In the Claims:

At Column 71, line 60, "Kpnl" should be -- KpnI --.

At Column 73, line 4, "dclined" should be -- defined --.

At Column 74, line 24, "ancuploidy" should be -- aneuploidy --.

Signed and Sealed this

Tenth Day of April, 2007

JON W. DUDAS
*Director of the United States Patent and Trademark Office*